United States Patent
Benyunes et al.

(10) Patent No.: US 12,128,103 B2
(45) Date of Patent: *Oct. 29, 2024

(54) ADJUVANT TREATMENT OF HER2-POSITIVE BREAST CANCER

(71) Applicants: Genentech, Inc., South San Francisco, CA (US); Hoffmann-La Roche Inc., Little Falls, NJ (US)

(72) Inventors: Mark C. Benyunes, San Francisco, CA (US); Graham Alexander Ross, Hertfordshire (GB)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/637,283

(22) Filed: Apr. 16, 2024

(65) Prior Publication Data

US 2024/0252634 A1 Aug. 1, 2024

Related U.S. Application Data

(62) Division of application No. 17/305,556, filed on Jul. 9, 2021, now Pat. No. 11,992,529, which is a division of application No. 15/907,718, filed on Feb. 28, 2018, now Pat. No. 11,077,189.

(60) Provisional application No. 62/486,876, filed on Apr. 18, 2017, provisional application No. 62/469,317, filed on Mar. 9, 2017, provisional application No. 62/466,239, filed on Mar. 2, 2017.

(51) Int. Cl.
| | | |
|---|---|---|
| *A61K 39/395* | (2006.01) | |
| *A61K 9/00* | (2006.01) | |
| *A61K 31/337* | (2006.01) | |
| *A61K 45/06* | (2006.01) | |
| *A61P 35/00* | (2006.01) | |
| *C07K 16/32* | (2006.01) | |
| *A61K 39/00* | (2006.01) | |

(52) U.S. Cl.
CPC ...... *A61K 39/39558* (2013.01); *A61K 9/0019* (2013.01); *A61K 45/06* (2013.01); *A61P 35/00* (2018.01); *C07K 16/32* (2013.01); *A61K 31/337* (2013.01); *A61K 2039/507* (2013.01); *A61K 2039/545* (2013.01); *A61K 2300/00* (2013.01)

(58) Field of Classification Search
CPC .......... A61K 39/3955; A61K 39/39558; A61K 2039/507; A61K 2039/545; A61K 2039/55; A61K 31/337; A61K 31/704; A61K 9/009; C07K 16/32; A61P 35/00
See application file for complete search history.

(56) References Cited

U.S. PATENT DOCUMENTS

| | | |
|---|---|---|
| 4,968,603 A | 11/1990 | Slamon et al. |
| 5,183,884 A | 2/1993 | Kraus et al. |
| 5,470,954 A | 11/1995 | Neslund et al. |
| 5,480,968 A | 1/1996 | Kraus et al. |
| 5,641,869 A | 6/1997 | Vandlen et al. |
| 5,648,237 A | 7/1997 | Carter et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,821,337 A | 10/1998 | Carter et al. |
| 5,824,311 A | 10/1998 | Greene et al. |
| 6,015,567 A | 1/2000 | Hudziak et al. |
| 6,054,297 A | 4/2000 | Carter et al. |
| 6,127,526 A | 10/2000 | Blank et al. |
| 6,165,464 A | 12/2000 | Hudziak et al. |
| 6,267,958 B1 | 7/2001 | Andya et al. |
| 6,333,169 B1 | 12/2001 | Hudziak et al. |
| 6,333,398 B1 | 12/2001 | Blank et al. |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,417,335 B1 | 7/2002 | Basey et al. |
| 6,489,447 B1 | 12/2002 | Basey et al. |
| 6,573,043 B1 | 6/2003 | Cohen et al. |

(Continued)

FOREIGN PATENT DOCUMENTS

| | | |
|---|---|---|
| EP | 1187632 B1 | 12/2008 |
| EP | 1846030 B1 | 11/2018 |

(Continued)

OTHER PUBLICATIONS

Clinical trial NCT01358877 (version 111), A Study of Pertuzumab in Addition to Chemotherapy and Trastuzumab as Adjuvant Therapy in Participants With Human Epidermal Growth Receptor 2 (HER2)-Positive Primary Breast Cancer, posted on Sep. 1, 2016.*

(Continued)

*Primary Examiner* — Hong Sang
(74) *Attorney, Agent, or Firm* — Wendy M. Lee

(57) ABSTRACT

Methods are provided for the adjuvant treatment of operable HER2-positive primary breast cancer in human patients by administration of pertuzumab in addition to chemotherapy and trastuzumab. The methods reduce the risk of recurrence of invasive breast cancer or death for a patient diagnosed with HER2-positive early breast cancer (eBC) compared to administration of trastuzumab and chemotherapy, without pertuzumab.

25 Claims, 17 Drawing Sheets

Specification includes a Sequence Listing.

(56) References Cited

U.S. PATENT DOCUMENTS

| | | |
|---|---|---|
| 6,627,196 B1 | 9/2003 | Baughman et al. |
| 6,632,979 B2 | 10/2003 | Erickson et al. |
| 6,639,055 B1 | 10/2003 | Carter et al. |
| 6,685,940 B2 | 2/2004 | Andya et al. |
| 6,695,940 B2 | 2/2004 | Devoe et al. |
| 6,719,971 B1 | 4/2004 | Carter et al. |
| 6,797,814 B2 | 9/2004 | Blank et al. |
| 6,800,738 B1 | 10/2004 | Carter et al. |
| 6,821,515 B1 | 11/2004 | Cleland et al. |
| 6,905,830 B2 | 6/2005 | Cohen et al. |
| 6,949,245 B1 | 9/2005 | Sliwkowski |
| 6,984,494 B2 | 1/2006 | Ralph |
| 7,018,809 B1 | 3/2006 | Carter et al. |
| 7,041,292 B1 | 5/2006 | Sliwkowski et al. |
| 7,060,268 B2 | 6/2006 | Andya et al. |
| 7,074,404 B2 | 7/2006 | Basey et al. |
| 7,097,840 B2 | 8/2006 | Erickson et al. |
| 7,129,051 B2 | 10/2006 | Cohen et al. |
| 7,129,840 B2 | 10/2006 | Hull et al. |
| 7,279,287 B2 | 10/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 2/2009 | Adams et al. |
| 7,485,704 B2 | 2/2009 | Fahrner et al. |
| 7,498,030 B2 | 3/2009 | Adams et al. |
| 7,501,122 B2 | 3/2009 | Adams et al. |
| 7,531,645 B2 | 5/2009 | Basey et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,618,631 B2 | 11/2009 | Sliwkowski |
| 7,674,589 B2 | 3/2010 | Cohen et al. |
| 7,682,609 B2 | 3/2010 | Andya et al. |
| 7,700,299 B2 | 4/2010 | Moecks et al. |
| 7,807,799 B2 | 10/2010 | Fahrner et al. |
| 7,811,773 B2 | 10/2010 | Ralph |
| 7,846,441 B1 | 12/2010 | Hellmann |
| 7,850,966 B2 | 12/2010 | Lowman et al. |
| 7,862,817 B2 | 1/2011 | Adams et al. |
| 7,879,325 B2 | 2/2011 | Kao et al. |
| 7,892,549 B2 | 2/2011 | Paton et al. |
| 7,919,254 B2 | 4/2011 | Cohen et al. |
| 7,981,418 B2 | 7/2011 | Amler et al. |
| 7,993,834 B2 | 8/2011 | Mass |
| 8,044,017 B2 | 10/2011 | Emery et al. |
| 8,075,890 B2 | 12/2011 | Carter et al. |
| 8,075,892 B2 | 12/2011 | Hellmann et al. |
| 8,076,066 B2 | 12/2011 | Mass |
| 8,142,784 B2 | 3/2012 | Ebens, Jr. et al. |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,333,964 B2 | 12/2012 | Agus et al. |
| 8,337,856 B2 | 12/2012 | Blattler et al. |
| 8,343,955 B2 | 1/2013 | Blaquiere et al. |
| 8,404,234 B2 | 3/2013 | Allison et al. |
| 8,425,908 B2 | 4/2013 | Hellman |
| 8,440,402 B2 | 5/2013 | Mass |
| 8,529,901 B2 | 9/2013 | Hasmann et al. |
| 8,591,897 B2 | 11/2013 | Bryant |
| 8,592,152 B2 | 11/2013 | Mass |
| 8,372,396 B2 | 12/2013 | Andya et al. |
| 8,597,654 B2 | 12/2013 | Bryant |
| 8,604,014 B2 | 12/2013 | Belvin et al. |
| 8,642,036 B2 | 2/2014 | Hellmann |
| 8,652,474 B2 | 2/2014 | Harris et al. |
| 8,652,479 B2 | 2/2014 | Ebens, Jr. et al. |
| 8,663,643 B2 | 3/2014 | Berry et al. |
| 8,691,232 B2 | 4/2014 | Derynck et al. |
| 8,710,196 B2 | 4/2014 | Emery et al. |
| 8,758,747 B2 | 6/2014 | Kallmeyer et al. |
| 8,840,896 B2 | 9/2014 | Lowman et al. |
| 8,940,302 B2 | 1/2015 | Amler et al. |
| 9,017,671 B2 | 4/2015 | Andya et al. |
| 9,090,700 B2 | 7/2015 | Friess et al. |
| 9,107,926 B2 | 8/2015 | Belvin et al. |
| 9,180,185 B2 | 11/2015 | Bauss et al. |
| 9,180,189 B2 | 11/2015 | Andya et al. |
| 9,181,346 B2 | 11/2015 | Harris et al. |
| 9,249,218 B2 | 2/2016 | Basey et al. |
| 9,283,273 B2 | 3/2016 | Andya et al. |
| 9,345,661 B2 | 5/2016 | Adler et al. |
| 9,376,715 B2 | 6/2016 | Brophy et al. |
| 9,551,033 B2 | 1/2017 | Lee-Hoeflich et al. |
| 9,687,568 B2 | 6/2017 | Hasmann et al. |
| 9,815,904 B2 | 11/2017 | Gennaro et al. |
| 9,868,760 B2 | 1/2018 | Emery et al. |
| 9,896,478 B2 | 2/2018 | Lebreton et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 5/2019 | Baughman et al. |
| 10,385,405 B2 | 8/2019 | Lee-Hoeflich et al. |
| 10,501,491 B2 | 12/2019 | Emery et al. |
| 10,689,457 B2 | 6/2020 | Paton et al. |
| 10,849,849 B2 | 12/2020 | Eng-Wong et al. |
| 10,898,570 B2 | 1/2021 | Phillips et al. |
| 11,077,189 B2 * | 8/2021 | Benyunes ............ A61K 9/0019 |
| 11,414,498 B2 | 8/2022 | Harris et al. |
| 11,597,776 B2 | 3/2023 | Harris et al. |
| 11,638,756 B2 * | 5/2023 | Benyunes ............ A61K 9/0019 424/133.1 |
| 11,654,105 B2 | 5/2023 | Eng-Wong et al. |
| 11,655,305 B2 | 5/2023 | Paton et al. |
| 11,992,529 B2 * | 5/2024 | Benyunes ............ A61P 35/00 |
| 2001/0014326 A1 | 8/2001 | Andya et al. |
| 2002/0001587 A1 | 1/2002 | Erickson et al. |
| 2002/0035736 A1 | 3/2002 | Erickson et al. |
| 2002/0064785 A1 | 5/2002 | Mass |
| 2002/0090662 A1 | 7/2002 | Ralph |
| 2003/0040509 A1 | 2/2003 | Moskowitz |
| 2003/0078388 A1 | 4/2003 | Basey et al. |
| 2003/0086924 A1 | 5/2003 | Sliwkowski |
| 2003/0134344 A1 | 7/2003 | Mass |
| 2003/0147884 A1 | 8/2003 | Paton et al. |
| 2003/0152987 A1 | 8/2003 | Cohen et al. |
| 2003/0162796 A1 | 8/2003 | Hilberg et al. |
| 2003/0170234 A1 | 9/2003 | Hellmann |
| 2003/0170235 A1 | 9/2003 | Cohen et al. |
| 2003/0202972 A1 | 10/2003 | Andya et al. |
| 2003/0232399 A1 | 12/2003 | Robertson et al. |
| 2004/0013667 A1 | 1/2004 | Kelsey et al. |
| 2004/0014694 A1 | 1/2004 | Chakroun |
| 2004/0037823 A9 | 2/2004 | Paton et al. |
| 2004/0048525 A1 | 3/2004 | Sagucio |
| 2004/0082047 A1 | 4/2004 | Emery et al. |
| 2004/0106161 A1 | 6/2004 | Bossenmaier et al. |
| 2004/0106180 A1 | 6/2004 | Blank et al. |
| 2004/0258685 A1 | 12/2004 | Brunetta et al. |
| 2005/0002928 A1 | 1/2005 | Hellmann |
| 2005/0025753 A1 | 2/2005 | Han et al. |
| 2005/0063972 A1 | 3/2005 | Basey et al. |
| 2005/0100944 A1 | 5/2005 | Cohen et al. |
| 2005/0158303 A1 | 7/2005 | Liu et al. |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2005/0244929 A1 | 11/2005 | Carter |
| 2005/0260204 A1 | 11/2005 | Allan |
| 2005/0276812 A1 | 12/2005 | Ebens et al. |
| 2006/0013819 A1 | 1/2006 | Kelsey et al. |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 3/2006 | Ralph |
| 2006/0067930 A1 | 3/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |

(56) References Cited

U.S. PATENT DOCUMENTS

| | | |
|---|---|---|
| 2006/0099201 A1 | 5/2006 | Andya et al. |
| 2006/0100168 A1 | 5/2006 | Ravid et al. |
| 2006/0121044 A1 | 6/2006 | Amler et al. |
| 2006/0165702 A1 | 7/2006 | Allison et al. |
| 2006/0182739 A1 | 8/2006 | Basey et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0216285 A1 | 9/2006 | Adams et al. |
| 2006/0228745 A1 | 10/2006 | Mass |
| 2006/0263434 A1 | 11/2006 | Desai et al. |
| 2006/0275305 A1 | 12/2006 | Bryant |
| 2006/0275306 A1 | 12/2006 | Andya et al. |
| 2007/0009976 A1 | 1/2007 | Lenz et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0166753 A1 | 7/2007 | Mass et al. |
| 2007/0184055 A1 | 8/2007 | Sliwkowski |
| 2007/0202516 A1 | 8/2007 | Mass et al. |
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0050748 A1 | 2/2008 | Cohen et al. |
| 2008/0102069 A1 | 5/2008 | Friess et al. |
| 2008/0108096 A1 | 5/2008 | Ralph |
| 2008/0112957 A1 | 5/2008 | Fendly et al. |
| 2008/0112958 A1 | 5/2008 | Mass |
| 2008/0160026 A1 | 7/2008 | Ashkenazi et al. |
| 2008/0171040 A1 | 7/2008 | Ebens, et al. |
| 2008/0187533 A1 | 8/2008 | Hellmann |
| 2008/0226659 A1 | 9/2008 | Erickson et al. |
| 2008/0241146 A1 | 10/2008 | Ashkenazi et al. |
| 2008/0286280 A1 | 11/2008 | Kallmeyer et al. |
| 2008/0317753 A1 | 12/2008 | Amler et al. |
| 2009/0081223 A1 | 3/2009 | Allison et al. |
| 2009/0087432 A1 | 4/2009 | Sliwkowski |
| 2009/0098135 A1 | 4/2009 | Belvin et al. |
| 2009/0099344 A1 | 4/2009 | Fahrner et al. |
| 2009/0131529 A1 | 5/2009 | Sherman et al. |
| 2009/0148401 A1 | 6/2009 | Mrsny |
| 2009/0148402 A1 | 6/2009 | Brunetta et al. |
| 2009/0148435 A1 | 6/2009 | Lebreton et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens et al. |
| 2009/0202546 A1 | 8/2009 | Harris et al. |
| 2009/0203015 A1 | 8/2009 | Chang et al. |
| 2009/0220492 A1 | 9/2009 | Basey et al. |
| 2009/0226455 A1 | 9/2009 | Filvaroff |
| 2009/0239236 A1 | 9/2009 | Mass |
| 2009/0285837 A1 | 11/2009 | Kao et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0112603 A1 | 5/2010 | Moecks et al. |
| 2010/0120053 A1 | 5/2010 | Cohen et al. |
| 2010/0158899 A1 | 6/2010 | Andya et al. |
| 2010/0196363 A1 | 8/2010 | Vanhauwere et al. |
| 2010/0285010 A1 | 11/2010 | Friess et al. |
| 2010/0298156 A1 | 11/2010 | Lee-Hoeflich et al. |
| 2011/0027190 A1 | 2/2011 | Hasmann et al. |
| 2011/0033460 A1 | 2/2011 | Fendly et al. |
| 2011/0044977 A1 | 2/2011 | Adler et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0129464 A1 | 6/2011 | Adams et al. |
| 2011/0151454 A1 | 6/2011 | Lee-Hoeflich et al. |
| 2011/0159014 A1 | 6/2011 | Lowman et al. |
| 2011/0165157 A1 | 7/2011 | Derynck et al. |
| 2011/0223159 A1 | 9/2011 | Friess et al. |
| 2011/0223619 A1 | 9/2011 | Belvin et al. |
| 2011/0236383 A1 | 9/2011 | Andya et al. |
| 2011/0245103 A1 | 10/2011 | Amler et al. |
| 2011/0246399 A1 | 10/2011 | Amler et al. |
| 2011/0250194 A1 | 10/2011 | Hellmann |
| 2012/0003217 A1 | 1/2012 | Bryant |
| 2012/0034213 A1 | 2/2012 | Hellmann |
| 2012/0034609 A1 | 2/2012 | Mass |
| 2012/0065381 A1 | 3/2012 | Emery et al. |
| 2012/0093838 A1 | 4/2012 | Mass |
| 2012/0107302 A1 | 5/2012 | Berry et al. |
| 2012/0107391 A1 | 5/2012 | Kelsey |
| 2012/0121586 A1 | 5/2012 | Kiermaier et al. |
| 2012/0251530 A1 | 10/2012 | Sliwkowski et al. |
| 2013/0039909 A1 | 2/2013 | Amler et al. |
| 2013/0071384 A1 | 3/2013 | Andya et al. |
| 2013/0095172 A1 | 4/2013 | Alavattam et al. |
| 2013/0108620 A1 | 5/2013 | Blattler et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0195845 A1 | 8/2013 | Fendly et al. |
| 2013/0195851 A1 | 8/2013 | Alavattam et al. |
| 2013/0209459 A1 | 8/2013 | Hellmann |
| 2013/0216532 A1 | 8/2013 | Adler et al. |
| 2013/0224185 A1 | 8/2013 | Andya et al. |
| 2013/0323180 A1 | 12/2013 | Hasmann et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin et al. |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 4/2014 | Dobosz et al. |
| 2014/0128580 A1 | 5/2014 | Ebens, Jr. et al. |
| 2014/0140993 A1 | 5/2014 | Ross et al. |
| 2014/0186343 A1 | 7/2014 | Harris et al. |
| 2014/0186347 A1 | 7/2014 | Derynck et al. |
| 2014/0186867 A1 | 7/2014 | Harris et al. |
| 2014/0212411 A1 | 7/2014 | Blattler et al. |
| 2014/0227255 A1 | 8/2014 | Bauss et al. |
| 2014/0248274 A1 | 9/2014 | Kallmeyer et al. |
| 2014/0248609 A1 | 9/2014 | Mass |
| 2014/0308277 A1 | 10/2014 | Gennaro et al. |
| 2014/0322202 A1 | 10/2014 | Cohen |
| 2014/0341886 A1 | 11/2014 | Hellmann |
| 2015/0037332 A1 | 2/2015 | Paton et al. |
| 2015/0056196 A1 | 2/2015 | Lebreton et al. |
| 2015/0072918 A1 | 3/2015 | Emery et al. |
| 2015/0079076 A1 | 3/2015 | Brophy et al. |
| 2015/0086545 A1 | 3/2015 | Sliwkowski et al. |
| 2015/0093381 A1 | 4/2015 | Allison et al. |
| 2015/0110816 A1 | 4/2015 | Blattler et al. |
| 2015/0111211 A1 | 4/2015 | Amler et al. |
| 2015/0150970 A1 | 6/2015 | Mass |
| 2015/0196642 A1 | 7/2015 | Andya et al. |
| 2015/0239969 A1 | 8/2015 | Friess et al. |
| 2015/0252113 A1 | 9/2015 | Fendly et al. |
| 2015/0273059 A1 | 10/2015 | Derynck et al. |
| 2015/0283238 A1 | 10/2015 | Friess et al. |
| 2016/0045515 A1 | 2/2016 | Belvin et al. |
| 2016/0060353 A1 | 3/2016 | Lowman et al. |
| 2016/0159912 A1 | 6/2016 | Bauss et al. |
| 2016/0166689 A1 | 6/2016 | Adler et al. |
| 2016/0175438 A1 | 6/2016 | Alavattam et al. |
| 2016/0376377 A1 | 12/2016 | Basey et al. |
| 2017/0008971 A1 | 1/2017 | Dennis et al. |
| 2017/0029527 A1 | 2/2017 | Paton et al. |
| 2017/0035907 A1 | 2/2017 | Green et al. |
| 2017/0037147 A1 | 2/2017 | Allison et al. |
| 2017/0073777 A1 | 3/2017 | Lee-Hoeflich et al. |

(56) References Cited

U.S. PATENT DOCUMENTS

| | | |
|---|---|---|
| 2017/0106097 A1 | 4/2017 | Blattler et al. |
| 2017/0136026 A1 | 5/2017 | Sliwkowski et al. |
| 2017/0166656 A1 | 6/2017 | Lowman et al. |
| 2017/0174785 A1 | 6/2017 | Harris et al. |
| 2017/0190786 A1 | 7/2017 | Fendly et al. |
| 2017/0226224 A1 | 8/2017 | Basey et al. |
| 2017/0360928 A1 | 12/2017 | Mass |
| 2018/0037660 A1 | 2/2018 | Gennaro et al. |
| 2018/0037661 A1 | 2/2018 | Gennaro et al. |
| 2018/0037662 A1 | 2/2018 | Gennaro et al. |
| 2018/0118781 A1 | 5/2018 | Lebreton et al. |
| 2018/0134803 A1* | 5/2018 | Douthwaite ........... C07K 16/32 |
| 2018/0162951 A1 | 6/2018 | Cohen |
| 2018/0251557 A1 | 6/2018 | Chui et al. |
| 2018/0201692 A1 | 7/2018 | Lowman et al. |
| 2018/0221481 A1 | 8/2018 | Beattie et al. |
| 2018/0221488 A1 | 8/2018 | Andya et al. |
| 2018/0228895 A1 | 8/2018 | Adler et al. |
| 2018/0236072 A1 | 8/2018 | Derynck et al. |
| 2018/0236093 A1 | 8/2018 | Bryant |
| 2018/0244715 A1 | 8/2018 | Emery et al. |
| 2018/0250397 A1 | 9/2018 | Benyunes et al. |
| 2018/0251536 A1 | 9/2018 | Friess et al. |
| 2018/0274038 A1 | 9/2018 | Belousov et al. |
| 2018/0280408 A1 | 10/2018 | Belvin et al. |
| 2018/0282428 A1 | 10/2018 | Fendly et al. |
| 2018/0296470 A1 | 10/2018 | Eng-Wong et al. |
| 2018/0327510 A1 | 11/2018 | Allison et al. |
| 2019/0055317 A1 | 2/2019 | Baughman et al. |
| 2019/0070291 A1 | 3/2019 | Mass |
| 2019/0117769 A1 | 4/2019 | Benyunes et al. |
| 2019/0240185 A1 | 8/2019 | Desmond-Hellmann et al. |
| 2019/0298861 A1 | 10/2019 | Dobosz et al. |
| 2019/0322761 A1 | 10/2019 | Harris et al. |
| 2019/0323089 A1 | 10/2019 | Lee-Hoeflich et al. |
| 2019/0345258 A1 | 11/2019 | Gennaro et al. |
| 2019/0352331 A1 | 11/2019 | Emery et al. |
| 2019/0352332 A1 | 11/2019 | Emery et al. |
| 2019/0352333 A1 | 11/2019 | Emery et al. |
| 2019/0374547 A1 | 12/2019 | Sliwkowski et al. |
| 2020/0048362 A1 | 2/2020 | Blattler et al. |
| 2020/0155701 A1 | 5/2020 | Bryant |
| 2020/0157238 A1 | 5/2020 | Gennaro et al. |
| 2020/0179515 A1 | 6/2020 | Andya et al. |
| 2020/0199690 A1 | 6/2020 | Belousov et al. |
| 2020/0206348 A1 | 7/2020 | Benyunes et al. |
| 2020/0237910 A1 | 7/2020 | Beattie et al. |
| 2020/0239574 A1 | 7/2020 | Allison et al. |
| 2020/0246267 A1 | 8/2020 | Haas et al. |
| 2020/0376120 A1 | 12/2020 | Benyunes et al. |
| 2021/0015919 A1 | 1/2021 | Benyunes et al. |
| 2021/0040216 A1 | 2/2021 | Chui et al. |
| 2021/0047429 A1 | 2/2021 | Paton et al. |
| 2021/0085597 A1 | 3/2021 | Eng-Wong et al. |
| 2021/0130398 A1 | 5/2021 | Emery et al. |
| 2021/0130399 A1 | 5/2021 | Emery et al. |
| 2021/0171571 A1 | 6/2021 | Emery et al. |
| 2021/0213130 A1 | 7/2021 | Phillips et al. |
| 2021/0330789 A1 | 10/2021 | Benyunes et al. |
| 2021/0353753 A1 | 11/2021 | Adler et al. |
| 2021/0403599 A1 | 12/2021 | Badovinac-Crnjevic et al. |
| 2022/0090212 A1 | 3/2022 | Belousov et al. |
| 2022/0170115 A1 | 6/2022 | Belousov et al. |
| 2022/0282337 A1 | 9/2022 | Belousov et al. |
| 2022/0363780 A1 | 11/2022 | Harris et al. |
| 2023/0000977 A1 | 1/2023 | Benyunes et al. |
| 2023/0047103 A1 | 2/2023 | Gennaro et al. |
| 2023/0092354 A1 | 3/2023 | Eng-Wong et al. |
| 2023/0212311 A1 | 7/2023 | Allison et al. |
| 2023/0250187 A1 | 8/2023 | Paton et al. |
| 2023/0263895 A1 | 8/2023 | Andya et al. |
| 2023/0277664 A1 | 9/2023 | Ross et al. |
| 2023/0310455 A1 | 10/2023 | Schutzman et al. |
| 2023/0314420 A1 | 10/2023 | Avenal et al. |
| 2023/0416401 A1 | 12/2023 | Harris et al. |
| 2024/0269064 A1 | 8/2024 | Eng-Wong et al. |

FOREIGN PATENT DOCUMENTS

| | | |
|---|---|---|
| EP | 2766040 B1 | 5/2019 |
| WO | 99/31140 A1 | 6/1999 |
| WO | 2001/00245 A3 | 1/2001 |
| WO | 01/89566 A1 | 11/2001 |
| WO | 2006/048749 A1 | 5/2006 |
| WO | 2006/078307 A1 | 7/2006 |
| WO | 2006/096861 A2 | 9/2006 |
| WO | 2007/143004 A2 | 12/2007 |
| WO | 2009/051815 A1 | 4/2009 |
| WO | 2009/154651 A1 | 12/2009 |
| WO | 2010/042705 A1 | 4/2010 |
| WO | 2010/059969 A2 | 5/2010 |
| WO | 2010/102276 A2 | 9/2010 |
| WO | 2010/136569 A1 | 12/2010 |
| WO | 2011/069074 A2 | 6/2011 |
| WO | 2011/146568 A1 | 11/2011 |
| WO | 2011/146568 A8 | 11/2011 |
| WO | 2012/120004 A1 | 9/2012 |
| WO | 2013/055874 A2 | 4/2013 |
| WO | 2013/083810 A1 | 6/2013 |
| WO | 2014/027056 A1 | 2/2014 |
| WO | 2014/083178 A1 | 6/2014 |
| WO | 2015/095418 A1 | 6/2015 |
| WO | 2022/013189 A1 | 1/2022 |
| WO | 2022/125483 A1 | 6/2022 |
| WO | 2023/178019 A1 | 9/2023 |

OTHER PUBLICATIONS

Clinical trail NCT10966471 (version 78), A Study of Trastuzumab Emtansine Plus Pertuzumab Following Anthracyclines in Comparison With Trastuzumab Plus Perjeta and a Taxane Following Anthracyclines as Adjuvant Therapy in Patients With Operable HER2-Positive Primary Breast Cancer, posted on Feb. 24, 2017.*

Clinical trial NCT10966471 (version 77), A Study of Trastuzumab Emtansine Plus Pertuzumab Following Anthracyclines in Comparison With Trastuzumab Plus Perjeta and a Taxane Following Anthracyclines as Adjuvant Therapy in Patients With Operable HER2-Positive Primary Breast Cancer, posted on Nov. 19, 2015.*

Schneeweiss et al., Annals of Oncology, 2013, 24: 2278-2284.*

NCT01358877 version105, A study of pertuzumab in addition to chemotherapy and trastuzumab as adjuvant therapy in patients with HER2 positive primary breast cancer, posted on Feb. 2, 2016.*

Agus et al., "Clinical activity in a phase I trial of HER-2-targeted rhuMAb 2C4 (pertuzumab) in patients with advanced solid malignancies (AST)" Pro Am Soc Clin Oncol 22:192 ( 2003).

Agus et al., "Targeting ligand-activated ErbB2 signaling inhibits breast and prostate tumor growth" Cancer Cell 2(2):127-37 (Aug. 2002).

Agus, D., et al., "Targeting ligand-activated ErbB2 signaling inhibits breast and prostate tumor growth" Cancer Cell 2(2):127-137 (Aug. 1, 2002).

Ahn, E. et al., "Dual HER2-targeted approaches in HER2-positive breast cancer" Breast Cancer Research and Treatment 131(2):371-383 (Sep. 29, 2011).

Ahn, E., et al., "Dual HER2-targeted approaches in HER2-positive breast cancer" Breast Cancer Res Treat 131(2):371-383 (Jan. 1, 2012).

Ajani, J., "Evolving chemotherapy for advanced gastric cancer" Oncologist 10(53):49-58 (Oct. 1, 2005).

Albain et al., "Adjuvant chemohormonal therapy for primary breast cancer should be sequential instead of concurrent: initial results from intergroup trial 0100 (SWOG-8814). [Abstract]" Proceedings of the American Society of Clinical Oncology Thirty-Eighth Annual Meeting, May 18-21, 2002, Orlando, Fla., Abstract 143, (2002).

(56) References Cited

OTHER PUBLICATIONS

Allison, D., et al., "Pharmacokinetics of HER2-Targeted rhuMAb 2C4 (OMNITARG) in Patients with Advanced Solid Malignancies: Phase IA Results" Poster (No. 790) 2003 ASCO Annual Meeting, Chicago, ILL-USA, pp. 1 ( Spring May 31-Jun. 3, 2003).
Allison, D., et al., "Pharmacokinetics of HER2-targeted rhuMAb 2C4 (pertuzumab) in patients with advanced solid malignancies: Phase Ia results" Pro Am Soc Clin Oncol 22:197 (Jun. 3, 2003).
American Cancer Society et al., "Breast Cancer Hormone Receptor Status" :24-26 (Sep. 20, 2019).
American Cancer Society et al., "Breast Cancer: Treatment Guide for Patients" NCCN 8:1-92 (Sep. 1, 2006).
American Joint Comm Cancer et al. AJCC Cancer Staging Manual (Entire Manual), Greene, F., eds, Sixth edition, New York, NY-US:Springer,:1-388 ( 2002).
American Joint Comm Cancer et al. AJCC Cancer Staging Manual "Part VII: Breast" Edge, S., eds., 7th edition, New York, NY-US:Springer,:1-29 ( 2010).
Amiri-Kordestani, et al., "First FDA Approval of Neoadjuvant Therapy for Breast Cancer: Pertuzumab for the Treatment of Patients with HER2-Positive Breast Cancer" Clinical Cancer Research 20(21):5359-5364 (Nov. 1, 2014).
Amler et al., "HER pathway gene expression analysis in a phase II study of pertuzumab + gemcitabine vs. gemcitabine + placebo in patients with platinum-resistant epithelial ovarian cancer" J Clin Oncol (Abstract 5552), 26( Suppl May 20):1-4 ( 2008).
Amler, L.C., et al., "Identification of a predictive expression pattern for phosphorylated HER2 and clinical activity of pertuzumab (OmnitargTM), a HER dimerization inhibitor in tumors from ovarian cancer patients" Proc Amer Assoc Cancer Res, AACR Meeting Abstracts (Abstract 4497, Retrieved May 31, 2013), 47:1-2 (Apr. 1, 2006) http://www.aacrmeetingabstracts.org/cgi/content/abstract/2006/1/1055-b.
Anderson et al., "Predicting and preventing the cardiotoxicity of cancer therapy" Expert Rev. Cardiovasc. Ther. 6(7):1023-1033 ( 2008,).
Andersson, M., et al., "Phase III Randomized Study Comparing Docetaxel Plus Trastuzumab With Vinorelbine Plus Trastuzumab as First-Line Therapy of Metastatic or Locally Advanced Human Epidermal Growth Factor Receptor 2-Positive Breast Cancer: The HERNATA Study" J Clin Oncol 29(3):284-271 (Jan. 20, 2011).
ANZCTR [Australian New Zealand Clinical Trials Registry] et al., "A Study of Pertuzumab in Combination With Herceptin and Chemotherapy in Participants With HER2-Positive Breast Cancer, 2009-012019-17" (ANZCTR—A Study of Pertuzumab in Combination With Herceptin and Chemotherapy in Participants With HER2-Positive Breast Cancer; NCT00976989; ID No. 2009-012019-17; Date Submitted: Sep. 14, 2009; Date Registered: Sep. 15, 2009 and Last Update Posted: Jun. 6, 2017: Printed: Feb. 12, 2020).
Archive History for NCT01358877, A Study of Pertuzumab in Addition to Chemotherapy and Trastuzumab as Adjuvant Therapy in Participants with Human Epidermal Growth Receptor 2 (HER2)-Positive Primary Breast Cancer, pp. 1-10 (May 8, 2018) http://clinicaltrials.gov/ct2/history/NCT01358877?V_112=View#StudyPageTop.
Archive History for NCT01358877, A Study of Pertuzumab in Addition to Chemotherapy and Trastuzumab as Adjuvant Therapy in Participants with Human Epidermal Growth Receptor 2 (HER2)-Positive Primary Breast Cancer, pp. 1-46 (Feb. 1, 2021) http://clinicaltrials.gov/ct2/history/NCT01358877?V_112=View#StudyPageTop.
Attard, G., et al., "A phase Ib study of pertuzumab, a recombinant humanised antibody to HER2, and docetaxel in patients with advanced solid tumours" Brit J Cancer 97(10):1338-1343 (Nov. 19, 2007).
Au, H., et al., "BCIRG 006: Quality of life (QoL) of patients (pts) treated with docetaxel and trastuzumab-based regimens in node positive and high risk node negative HER2 positive early breast cancer" San Antonio Breast Cancer Symposium, pp. 1 (2007).

Au, H., et al., "BCIRG 006: Quality of life (QoL) of patients (pts) treated with docetaxel and trastuzumab-based regimens in node positive and high risk node negative HER2 positive early breast cancer" (Abstract 3064; Conference: SABCS (San Antonio Breast Cancer Symposium)),:p. 1 ( 2006).
Au, H., et al., "BCIRG 006: Quality of life of patients treated with docetaxel and trastuzumab-based regimens in node positive and high risk node negative HER2 positive early breast cancer" (Poster Presented by: Dr. Au from the Cross Cancer Institute in Edmonton Alberta (Canada) at SABCS (San Antonio Breast Cancer Symposium)),:1-3 ( 2006).
Bang, Y., et al., "Trastuzumab in combination with chemotherapy versus chemotherapy alone for treatment of HER2-positive advanced gastric or gastro-oesophageal junction cancer (ToGA): a phase 3, open-label, randomised controlled trial" LANCET 376(9742):687-697 (Aug. 28, 2010).
Baselga, J., et al., "CLEOPATRA: a phase III evaluation of pertuzumab and trastuzumab for HER2-positive metastatic breast cancer" Clinical Breast Cancer 10(6):489-491 (Dec. 1, 2010).
Baselga, J., et al., "Efficacy, safety, and tolerability of dual monoclonal antibody therapy with Pertuzumab + Trastuzumab in HER2+ metastatic breast cancer patients previously treated with Trastuzumab" (Poster 3138) 2008 San Antonio Breast Cancer Symposium (SABCS), San Antonio, TX, pp. 1 ( Dec. 10-14, 2008).
Baselga, J., et al., "Objective response rate in a phase II multicenter trial of pertuzumab (P), a HER2 dimerization inhibiting monoclonal antibody, in combination with trastuzumab (T) in patients (pts) with HER2-positive metastatic breast cancer (MBC) which has progressed during treatment with T" J Clin Oncol (Abstract 1004; 2007 ASCO Annual Meeting), 25(18S):1-2 (Jun. 20, 2007).
Baselga, J., et al., "Pertuzumab plus trastuzumab plus docetaxel for metastatic breast cancer" N Engl J Med 366(2):109-119 (Jan. 12, 2012).
Baselga, J., et al., "Phase II study of weekly intravenous recombinant humanized anti-p185HER2 monoclonal antibody in patients with HER2/neu-overexpressing metastatic breast cancer" J Clin Oncol 14(3):737-744 (Mar. 1, 1996).
Baselga, J., et al., "Phase II Trial of Pertuzumab and Trastuzumab in Patients With Human Epidermal Growth Factor Receptor 2-Positive Metastatic Breast Cancer That Progressed During Prior Trastuzumab Therapy" J Clin Oncol 28(7):1138-1144 (Mar. 1, 2010).
Bayraktar, S., et al., "Efficacy of Neoadjuvant Therapy with Trastuzumab Concurrent with Anthracycline- and Non-anthracycline-based Regimens for HER2-Positive Breast Cancer" Cancer 118(9):2385-2393 (May 1, 2012).
Bear et al., "Sequential preoperative or postoperative docetaxel added to preoperative doxorubicin plus cyclophosphamide for operable breast cancer:National Surgical Adjuvant Breast and Bowel Project Protocol B-27" J Clin Oncol. 24(13):2019-27 ( 2006).
Bellenger et al., "Comparison of left ventricular ejection fraction and vols. in heart failure by echocardiography, radionuclide ventriculography and cardiovascular magnetic resonance; are they interchangeable?" European Heart Journal 21:1387-1396 ( 2000).
Bendig, M. M., "Humanization of Rodent Monoclonal Antibodies by CDR Grafting" Methods 8:83-93 (1995).
Bhargava, R., et al., "Semiquantitative hormone receptor level influences response to trastuzumab-containing neoadjuvant chemotherapy in HER2-positive breast cancer" Modern Pathol 24(3):367-374 (Mar. 1, 2011).
Biosimilar and Interchangeable Products, U.S. Food and Drug Administration, dated Oct. 23, 2017. Aviaible on the web at <https://www.fda.gov/drugs/biosimilars/biosimilar-and-interchangeable-products> printed Nov. 12, 2020, pp. 1-5.
Bitzan, M., et al., "Safety and pharmacokinetics of chimeric anti-Shiga toxin 1 and anti-Shiga toxin 2 monoclonal antibodies in healthy volunteers" Antimicrob Agents Chemother 53(7):3081-3087 (Jul. 1, 2009).
Bray, F., et al., "Ovarian cancer in Europe: Cross-sectional trends in incidence and mortality in 28 countries, 1953-2000" Int J Cancer 113(6):977-990 (Mar. 1, 2005).
Breast Cancer Facts & Figures 2006-2008 published by Korean Breast Cancer Association (2008), pp. 1-28. Concise explanation in English attached.

(56) References Cited

OTHER PUBLICATIONS

Breast Cancer Stages <https://www.breastcancer.org/symptoms/diagnosis/staging>, last updated May 4, 2020, pp. 1-8.
Breast Cancer.org et al., "Early-Stage Breast Cancer More Deadly in Men Than Women" breastcancer.org:1 (May 9, 2007) https://www.breastcancer.org/research-news/20070509.
Burris et al., "Abstract A6: Pazopanib combination with paclitaxel and carboplatin in patients with advanced solid tumors and gynecological cancers: Results of two phase I studies" Mol Cancer Ther 8( Suppl 12):A6 ( 2009).
Calvo et al., "Phase I study of PM00104 in combination with carboplatin (C) in patients (pts) with advanced solid tumors." J Clin Oncol 29(15):1-5 ( 2011).
Cameron, D. et al., "Adjuvant bevacizumab-containing therapy in triple-negative breast cancer (BEATRICE): primary results of a randomised, phase 3 trial" Lancet Oncol (http://dx.doi.org/10.1016/S1470-2045(13)70335-8), 14:933942 (Aug. 7, 2013).
Campiglio, M., et al., "Characteristics of EGFR family-mediated HRG signals in human ovarian cancer" J Cell Biochem 73(4):522-532 (Jun. 15, 1999).
Carlson, R.W., et al., "HER2 testing in breast cancer: NCCN Task Force report and recommendations" J National Comprehensive Cancer Network 4( Suppl 3):S1-S24 (Jul. 1, 2006).
Catalano, V. et al., "Gastric cancer" Crit Rev Oncol/Hematol 54(3):209-241 (Jun. 1, 2005).
Center for Drug Evaluation and Research Approval Package for "Perjeta," Application No. 125409Orig1s0051, pp. 1-104 ( Sep. 25, 2013).
Chan et al., "Phase II study of gemcitabine and carboplatin in metastatic breast cancers with prior exposure to anthracyclines and taxanes" Invest New Drugs 28:859-865 ( 2010).
Chang, H., et al., "110: Clinical Advantages of Neoadjuvant Docetaxel (T) and Carboplatin (C) ± Trastuzumab (H) in Locally Advanced Breast Cancer (LABC)" Cancer Res 69( Suppl 24):571s (Dec. 15, 2009).
Chang, H., et al., "Differential response of triple-negative breast cancer to a docetaxel and carboplatin-based neoadjuvant treatment" Cancer 116(18):4227-4237 (Sep. 15, 2010).
Charfare, H., et al., "Neoadjuvant chemotherapy in breast cancer: Review" Br J Surg 92(1):14-23 (Jan. 1, 2005).
Chen, T.W., et al., "Should pertuzumab be used as part of neoadjuvant treatment prior to the release of the APHINITY trial results?" Transl Cancer Res 5( Suppl 4):S907-S912 (Oct. 1, 2016).
Chlebowski et al., "A Decade of Breast Cancer Clinical Investigation: Results as Reported in the Program/Proceedings of the American Society of Clinical Oncology" J Clin Oncol 12(9):1789-1795 (1994).
Cho, H.S., et al., "Structure of the extracellular region of HER2 alone and in complex with the Herceptin Fab" Nature 421(6924):756-760 (Feb. 13, 2003).
Chu, E., et al. Cancer Principles and Practices of Oncology "Chapter 7: Principles of Cancer Management: Chemotherapy" De Vita, V., eds, 6th edition, Philadelphia, PA:Lippincott Williams & Wilkins,:289-306 (2001).
"Clinical trail NCT10966471 (version 78), A Study of Trastuzumab Emtansine Plus Pertuzumab Following Anthracyclines in Comparison With Trastuzumab Plus Perjeta and a Taxane Following Anthracyclines as Adjuvant Therapy in Patients With Operable HER2-Positive Primary Breast Cancer":1-47 (Feb. 24, 2017).
"Clinical trial NCT01358877 (version 111), A Study of Pertuzumab in Addition to Chemotherapy and Trastuzumab as Adjuvant Therapy in Participants With Human Epidermal Growth Receptor 2 (HER2)-Positive Primary Breast Cancer":1-8 (Sep. 1, 2016).
"Clinical trial NCT01358877—V111, A Study of Pertuzumab in Addition to Chemotherapy and Trastuzumab as Adjuvant Therapy in Participants With Human Epidermal Growth Receptor 2 (HER2)-Positive Primary Breast Cancer" posted Sep. 1, 2016, last updated Dec. 21, 2023:1-48 (Dec. 21, 2023).
"Clinical trial NCT10966471 (version 77), A Study of Trastuzumab Emtansine Plus Pertuzumab Following Anthracyclines in Comparison With Trastuzumab Plus Perjeta and a Taxane Following Anthracyclines as Adjuvant Therapy in Patients With Operable HER2-Positive Primary Breast Cancer":1-34 (Nov. 19, 2015).
Clinical Trials.gov et al., "A Study of Pertuzumab in Addition to Chemotherapy and Herceptin (Trastuzumab) as Adjuvant Therapy in Patients With HER2-Positive Primary Breast Cancer" (Chemotherapy and Herceptin (Trastuzumab); NCT01358877; Protocol ID: BO25126; Submitted Date: Feb. 1, 2016 (v105); Last Updated Posted: Feb. 2, 2016; Printed: May 21, 2020),:1-22 (Feb. 2, 2016).
Clinical Trials.gov et al., "A Study of Pertuzumab in Combination With Herceptin and Chemotherapy in Participants With HER2-Positive Breast Cancer" (Pertuzumab in Combination With Herceptin and Chemotherapy; NCT 00976989; Key Record Dates; First Submitted: Sep. 14, 2009; First Posted: Sep. 15, 2009; Results First Submitted: Mar. 28, 2016; Results First Posted: Jun. 20, 2016; Last Updated Posted: Feb. 6, 2017; Date Printed: unknown),:1.
Clinical Trials.gov et al., "A Study of Pertuzumab in Combination With Herceptin in Patients With HER2 Positive Breast Cancer" (Pertuzumab in Combination With Herceptin—NCT00545688; Study Protocol ID: WO20697 ; Date Submitted: Oct. 16, 2007; Date First Posted: Oct. 17, 2007; Last Updated: Jul. 5, 2017; Printed: Feb. 12, 2020),:1-12 https://clinicaltrials.gov/ct2/show/study/NCT00545688?id=00545688&draw=2&rank=1.
Clinical Trials.gov, A Study of Neo ALTTO (Neoadjuvant Lapatinib and/or Trastuzumab Treatment Optimization) (Neo Altto) NCT0055358; Protocol ID: EGF106903 ; First Submitted: May 20, 2011, Last Updated Posted: Oct. 12, 2011 Printed: Aug. 24, 2021 ),:1-24 (Oct. 12, 2011).
Clinical Trials.gov, "A Study of Pertuzumab in Addition to Chemotherapy and Herceptin (Trastuzumab) as Adjuvant Therapy in Patients With HER2-Positive Primary Breast Cancer" (Chemotherapy and Herceptin (Trastuzumab); NCT01358877; Protocol ID: BO25126; Other IDs: TOC4939G, 2010-022902-41 [EudraCT Number], BIG 04-11 [Breast International Group]; Submitted Date: Nov. 1, 2016 (v112); First Submitted: May 20, 2011; First Posted: May 24, 2011; Last Updated Posted: Nov. 2, 2016),:1-20 (Nov. 1, 2016).
Clinical Trials.gov, "A Study of Pertuzumab in Addition to Chemotherapy and Herceptin (Trastuzumab) as Adjuvant Therapy in Patients With HER2-Positive Primary Breast Cancer" (Chemotherapy and Herceptin (Trastuzumab); NCT01358877; Protocol ID: BO25126; First Submitted: May 20, 2011, Last Updated Posted: Nov. 2, 2016 [Est.]; Printed: Feb. 1, 2021),:1-46 (Nov. 1, 2016).
Clinical Trials.gov, "A Study of Pertuzumab in Addition to Chemotherapy and Herceptin (Trastuzumab) as Adjuvant Therapy in Patients With HER2-Positive Primary Breast Cancer":1-10 (Feb. 6, 2017).
Clinical Trials.gov, "A Study of Pertuzumab in Combination With Herceptin and Chemotherapy in Participants With HER2-Positive Breast Cancer" (Pertuzumab in Combination With Herceptin and Chemotherapy; NCT0976989; History of Changes of Study; First Submitted: Sep. 14, 2009; First Posted: Sep. 15, 2009; Last Updated Posted: Sep. 21, 2011; Printed: unknown),:1-10 https://clinicaltrials.gov/ct2/history/NCT00976989.
Clinical Trials.gov, "A Study of Pertuzumab in Combination With Herceptin and Chemotherapy in Participants With HER2-Positive Breast Cancer" (Pertuzumab in Combination With Herceptin and Chemotherapy; NCT 00976989; First Submitted: Sep. 14, 2009; First Posted; Sep. 15, 2009; Last Updated Posted: Sep. 18, 2009 (v2); Date Printed: unknown),:1-9 https://clinicaltrials.gov/ct2/history/NCT00976989.
Clinical Trials.gov, "A Study of Pertuzumab in Combination With Herceptin in Patients With HER2 Positive Breast Cancer" (Pertuzumab in Combination With Herceptin, NCT00545688—History of Changes for Study—Last Updated Posted: Jul. 5, 2017; Print Dated: Dec. 16, 2019),:1-14 https://clinicaltrials.gov/ct2/show/study/NCT00545688?id=00545688&draw=2&rank=1.
Clinical Trials.gov, "A Study of Pertuzumab in Combination With Herceptin and Chemotherapy in Participants With HER2-Positive Breast Cancer" (Pertuzumab in Combination With Herceptin and Chemotherapy; NCT 00976989; History of Changes for Study; Protocol ID: BO22280; First Submitted: Sep. 14, 2009; First

(56) References Cited

OTHER PUBLICATIONS

Postefd: Sep. 15, 2009; Last Updated Posted: Nov. 16, 2011 (v29); Date Printed: unknown),:1-10 https://clinicaltrials.gov/ct2/history/NCT00976989.
ClinicalTrials.gov, "A Study of Pertuzumab in Combination With Herceptin and Chemotherapy in Participants With HER2-Positive Breast Cancer" NCT00976989, History of changes comparison between V2 and V3, last version submitted Dec. 12, 2016, printed on Mar. 26, 2024:1-12.
ClinicalTrials.gov, "A Study of Pertuzumab in Combination With Herceptin and Chemotherapy in Patients With HER2-Positive Breast Cancer" History of changes NCT00976989 V68; First submitted Sep. 14, 2009; Last updated Jan. 1, 2016 [Est]; Submitted Dec. 12, 2016, printed on Mar. 26, 2024:1-12.
ClinicalTrials.gov, "A Study of Pertuzumab in Combination With Herceptin and Chemotherapy in Participants With HER2-Positive Breast Cancer" (Pertuzumab; NCT00976989; First Posted: Sep. 15, 2009; Last Update Posted: Feb. 6, 2017; Printed Nov. 29, 2019),:1-10.
ClinicalTrials.gov, "A Study of Pertuzumab in Combination With Herceptin and Chemotherapy in Participants With HER2-Positive Breast Cancer" NCT00976989, History of changes comparison between V1 and V2, last version submitted Dec. 12, 2016, printed on Mar. 26, 2024:1-12.
ClinicalTrials.gov, "A Study of Pertuzumab in Combination With Herceptin and Chemotherapy in Participants With HER2-Positive Breast Cancer (Tryphaena)" (Pertuzumab and Herceptin; NCT00976989; First Posted: Sep. 15, 2009: Last Update Posted: Feb. 6, 2017: Printed Jan. 21, 2020),:1-10 https://clinicaltrials.gov/ct2/show/NCT00976989.
Clinicaltrials.gov, "A Study of Pertuzumab in Combination With Herceptin and Chemotherapy in Patients With HER2-Positive Breast Cancer" History of changes NCT00976989 V69; First submitted Sep. 14, 2009; Results first posted Jun. 20, 2016 [Est]; Submitted Dec. 12, 2016, printed on Mar. 26, 2024:1-29.
ClinicalTrials.gov, "A Study of Pertuzumab in Combination With Herceptin and Chemotherapy in Participants With HER2-Positive Breast Cancer (History of Changes for Study as of Dec. 12, 2016)" (Pertuzumab; NCT00976989; First posted Sep. 15, 2009; Last Posted: Feb. 6, 2017; Printed:Dec. 9, 2019),:1-17 https://clinicaltrials.gov/ct2/show/NCT00976989?term=NCT00976989&draw=2&rank=1.
ClinicalTrials.gov, "A Study of Pertuzumab in Combination With Herceptin and Chemotherapy in Patients With HER2Positive Breast Cancer (History of Study as of Nov. 16, 2009)" (Pertuzumab; NCT00976989; BO22280; Printed: Apr. 26, 2017),:1-3.
ClinicalTrials.gov, "A Study of Pertuzumab in Combination With Herceptin and Chemotherapy in Participants With HER2-Positive Breast Cancer" NCT00976989, History of changes comparison between V68 and V69, last version submitted Dec. 12, 2016, printed on Mar. 26, 2024:1-31.
ClinicalTrials.gov, "A Study of Pertuzumab in Combination With Trastuzumab Plus an Aromatase Inhibitor in Participants With Metastatic Human Epidermal Growth Factor Receptor 2 (HER2)-Positive and Hormone Receptor-Positive Advanced Breast Cancer (Pertain)" (Pertuzumab and Trastuzumab Plus an Aromatase Inhibitor; NCT01491737; First Posted: Dec. 14, 2011; Last Update Posted: Dec. 18, 2019; Printed: Jan. 21, 2020),:1-10 https://clinicaltrials.gov/ct2/show/NCT01491737.
ClinicalTrials.gov, "A Study of Pertuzumab in Combination With Trastuzumab and Chemotherapy in Patients With HER2-Positive Advanced Gastric Cancer (Joshua)" (Pertuzumab and Trastuzumab; NCT01461057; First Posted: Oct. 27, 2011; Last Update Posted: Aug. 9, 2018; Printed: Jan. 21, 2020),:1-7 https://clinicaltrials.gov/ct2/show/study/NCT01461057.
ClinicalTrials.gov, "A Study of Pertuzumab in Combination With Trastuzumab and Chemotherapy in Participants With Human Epidermal Growth Factor Receptor 2 (HER2)-Positive Metastatic Gastroesophageal Junction or Gastric Cancer (Jacob)" (Pertuzumab and Trastuzumab; NCT01774786; First Posted: Jan. 24, 2013: Last Update Posted: Jan. 2020; Printed: Jan. 21, 2020),:1-12 https://clinicaltrials.gov/ct2/show/NCT01774786.
ClinicalTrials.gov, "A Study of Pertuzumab in Combination With Trastuzumab (Herceptin) and a Taxane in First-Line Treatment in Participants With Human Epidermal Growth Factor 2 (HER2)-Positive Advanced Breast Cancer (Peruse)" (Pertuzumab, Trastuzumab and Taxane; NCT01572038; First Posted: Apr. 5, 2012; Last Update Posted: Jan. 13, 2020; Printed: Jan. 21, 2020),:1-8 https://clinicaltrials.gov/ct2/show/NCT01572038?cond=NCT01572038.
ClinicalTrials.gov, "A Study to Assess Efficacy and Safety of Pertuzumab Given in Combination With Trastuzumab and Vinorelbine in Participants With Metastatic or Locally Advanced Human Epidermal Growth Factor Receptor (HER) 2-Positive Breast Cancer (Velvet)" (Pertuzumab, Trastuzumab and Vinorelbine; NCT01565083; First Posted: Mar. 28, 2012; Last Update Posted: Nov. 22, 2016; Printed: Jan. 21, 2020),:1-11 https://clinicaltrials.gov/ct2/show/NCT01565083.
ClinicalTrials.gov, "A Study to Evaluate Pertuzumab + Trastuzumab + Docetaxel vs. Placebo + Trastuzumab + Docetaxel in Previously Untreated HER2-Positive Metastatic Breast Cancer (Cleopatra)" (Pertuzumab + Trastuzumab + Docetaxel vs. Placebo + Trastuzumab + Docetaxel; NCT00567190; First Posted: Dec. 4, 2007; Last Update Posted: Dec. 13, 2019; Printed: Aug. 25, 2021 ),:1-10 https://clinicaltrials.gov/ct2/show/NCT00567190.
ClinicalTrials.gov, "A Study to Evaluate Pertuzumab + Trastuzumab + Docetaxel vs. Placebo + Trastuzumab + Docetaxel in Previously Untreated HER2-Positive Metastatic Breast Cancer (Cleopatra)" (Pertuzumab + Trastuzumab + Docetaxel vs. Placebo + Trastuzumab + Docetaxel; NCT00567190; First Posted: Dec. 4, 2007; Last Update Posted: Dec. 13, 2019; Printed: Jan. 21, 2020),:1-20 https://clinicaltrials.gov/ct2/show/NCT00567190.
ClinicalTrials.gov, "History of Changes for Study: NCT00545688 A Study of Pertuzumab in Combination With Herceptin in Patients With HER2 Positive Breast Cancer, Last Updated Jul. 18, 2023":1-66 (Dec. 16, 2015).
ClinicalTrials.gov, "History of Changes for Study: NCT01358877 A Study of Pertuzumab in Addition to Chemotherapy and Trastuzumab as Adjuvant Therapy in Participants With Human Epidermal Growth Receptor 2 (HER2)-Positive Primary Breast Cancer, Last Updated Jul. 18, 2023":1-44 (Sep. 1, 2016).
ClinicalTrials.gov, "History of Changes for Study: NCT02132949 A Study Evaluating Pertuzumab (Perjeta) Combined With Trastuzumab (Herceptin) and Standard Anthracycline-based Chemotherapy in Participants With Human Epidermal Growth Factor Receptor 2 (HER2)-Positive Locally Advanced, Inflammatory, or Early-stage Breast Cancer, Last Updated Jul. 18, 2023":1-53 (Mar. 1, 2017).
ClinicalTrials.gov, "Pertuzumab in Platinum-Resistant Low Human Epidermal Growth Factor Receptor 3 (HER3) Messenger Ribonucleic Acid (mRNA) Epithelial Ovarian Cancer (Penelope)" (Pertuzumab; NCT01684878; First Posted: Sep. 13, 2012; Last Update Posted: May 23, 2017; Printed: Jan. 21, 2020),:1-12 https://clinicaltrials.gov/ct2/show/NCT01684878.
ClinicalTrials.gov et al., "A Study of Pertuzumab in Combination With Herceptin and Chemotherapy in Participants With HER2-Positive Breast Cancer (Tryphaena)" (Pertuzumab and Herceptin; NCT00976989; First Posted: Sep. 15, 2009: Last Update Posted: Feb. 6, 2017: Printed Apr. 11, 2022),:1-19 https://clinicaltrials.gov/ct2/show/NCT00976989.
Coiffier et al., "CHOP Chemotherapy Plus Rituximab Compared with CHOP Alone in Elderly Patients With Diffuse Large-B-Cell Lymphoma" New Engl J Med 346(4):235-242 ( 2012).
"Common Terminology Criteria for Adverse Events v3.0 (CTCAE)" Cancer Therapy Evaluation Program:1-72 (Aug. 9, 2006).
Communication of the Board of Appeal Pursuant to Article 15(1) for European Patent Application No. 15160406.3 dated Oct. 19, 2020, pp. 1-9.
Constantini et al., "Trastuzumab-Resistant Breast Cancer Cells Remain Sensitive to the Auger Electron-Emitting Radiotherapeutic Agent 111 In-NLS-Trastuzumab and Are Radiosensitized by Methotrexate" The Journal of Nuclear Medicine 49(9):1498-1505 (Sep. 2008).
Cortazar et al., "Implications of the CTNeoBC Meta-analysis" AACR ASCO Workshop:1-50 (Mar. 22, 2013).

(56) References Cited

OTHER PUBLICATIONS

Cortazar et al., "Pathological complete response and long-term clinical benefit in breast cancer: the CTNeoBC pooled analysis" Lancet 384:164-172 ( 2014).
Cortazar, "S1-11. Meta-analysis Results from the Collaborative Trials in Neoadjuvant Breast Cancer (CTNeoBC)" CTRC-AACR San Antonion Breast Cancer Symposium:1-32 ( 2012).
Cortes, J., et al., "Docetaxel combined with targeted therapies in metastatic breast cancer" Cancer Treat Rev 38(5):387-396 (Aug. 1, 2012).
Coudert et al., "Pre-Operative Systemic (Neo-Adjuvant) Therapy with Trastuzumab and Docetaxel for HER2-Overexpressing Stage II or III Breast Cancer: Results of a Multicenter Phase II Trial" Ann Oncol 17:409-414 ( 2006).
Coudert, B., et al., "Multicenter phase II trial of neoadjuvant therapy with trastuzumab, docetaxel, and carboplatin for human epidermal growth factor receptor-2-overexpressing stage II or III breast cancer: results of the GETN(A)-1 trial" J Clin Oncol 25(19):2678-2684 (Jul. 1, 2007).
Cristofanilli et al., "Circulating tumor cells: a novel prognostic factor for newly diagnosed metastatic breast cancer" J Clin Oncol. 23(7):1420-1430 (Mar. 1, 2005).
Crown, J., et al., "Platinum-taxane combinations in metastatic breast cancer: an evolving" Breast Cancer Res Treat 79( Suppl 1):S11-S18 (Mar. 1, 2003).
CSCO—Chinese Society Clinical Oncology et al., "Guidelines of the Chinese Society of Clinical Oncology [CSCO]—Breast Cancer" People's Medical Publishing House-Beijing (Excerpt pp. 12, 14—Chinese w/Eng. Translation),:12, 14 (Jan. 1, 2022).
Cunningham, D., et al., "ESMO minimum clinical recommendations for diagnosis, treatment and follow-up of gastric cancer" Ann Oncol 16( Suppl 1):122-123 ( 2005).
Cuzick, J. et al., "Overview of the main outcomes in breast-cancer prevention trials" The Lancet 361(9354):296-300 (Jan. 25, 2003).
De Boer, R.H., et al., "Use of non-anthracycline regimens in early stage breast cancer in Australia" Asia Pac J Clin Oncol 7(1):4-10 (Mar. 1, 2011).
Declaration of Graham Ross regarding U.S. Appl. No. 16/796,163, signed Nov. 20, 2020, pp. 1-8.
Declaration of Graham Ross, dated Nov. 16, 2020, pp. 1-10.
Dickstein, K. et al., "ESC Guidelines for the diagnosis and treatment of acute and chronic heart failure 2008" European Heart Journal 29:2388-2442 (Aug. 30, 2008).
"DOCETAXEL Prescribing Information" (Nov. 2022).
Doisneau-Sixou et al., "Estrogen and antiestrogen regulation of cell cycle progression in breast cancer cells" Endocrine-Related Cancer 10:179-186 ( 2003).
Doxorubicin Hydrochloride United States Prescribing Information (USPI),:pp. 1-26 (Oct. 2013).
Du Bois, A., et al., "Role of surgical outcome as prognostic factor in advanced epithelial ovarian cancer: A combined exploratory analysis of 3 prospectively randomized phase 3 multicenter trials" Cancer 115(6):1234-1244 (Mar. 15, 2009).
Eisenhauer et al., "New response evaluation criteria in solid tumours: Revised RECIST guideline" Eur J Cancer 45:228-247 ( 2009).
"Epirubicin United States Prescribing Information USPI" (Jul. 2011).
"Epirubicin United States Prescribing Information USPI":1-19 (Dec. 2014).
Eschenhagen et al., "Cardiovascular side effects of cancer therapies: a position statement from the Heart Failure Association of the European Society of Cardiology" European Journal of Heart Failure 13:1-10 ( 2011).
Esserman et al., "Accelerated Approval for Pertuzumab in the Neoadjuvant Setting: Winds of Change?" Clinical Cancer Research 20(14):3632-3636 ( 2014).
European Medicines Agency [EMA] et al., "Assessment Report—Perjeta : International non-proprietary name: pertuzumab" (Procedure No. EMEA/H/C/002547/II/0010),( Suppl EMA/CHMP/285991/2015):1-95 (Jun. 25, 2015).

European Medicines Agency [EMA], "Guideline on the evaluation of anticancer medicinal products in man" ( Suppl EMA/CHMP/205/95 Rev.5):1-43 (Sep. 22, 2017).
European Medicines Agency, "Assessment Report for Herceptin (Trastuzumab), Procedure No. EMEA/H/C/000278/II/57" Committee for Medicinal Products for Human Use EMA/36190/2012:1-58 (Nov. 17, 2011).
European Medicines Agency, "Introduction to the Summary of Product Characteristics (SmPC)":1-7 (Aug. 31, 2017).
European Medicines Agency, Science Medicines Health: Guideline on the Investigation of Drug Interactions, Committee for Human Medicinal Products (CHMP), pp. 1-59 ( Jun. 21, 2012).
Evans et al., "Vaccine therapy for cancer—fact or fiction?" QJ Med—Intl J Medicine—UK 92(6):299-307 (Jun. 1999).
Ewer et al., "Cardiotoxicity Profile of Trastuzumab" Drug Safety 31(8):459-467 ( 2008).
"Excerpt from Section 1.1.1 within Section 2.7.4 (Summary of Clinical Safety) of Perjeta neoadjuvant sBLA submitted to FDA":1-3 (Apr. 30, 2013).
"Excerpt of Roche Clinical Study Report—WO20698C/TOC4129g—A Phase III, Randomized, Double-Blind, Placebo-Controlled Clinical Trial to Evaluate the Efficacy and Safety of Pertuzumab + Trastuzumab + Docetaxel vs. Placebo + Trastuzumab + Docetaxel in Previously Untreated HER2-Positive Metastatic Breast Cancer—Report No. 1046288": pp. 1, 41, 116-118, 140, 1116, 1117 (8 pages) (Oct. 2011).
Expert Declaration of Alison Stopeck with CV dated Sep. 20, 2021 pp. 1-43.
F. Hoffmann La-Roche Ltd., Pertuzumab combined with Herceptin and chemotherapy significantly extended the time people with HER2-positive metastatic breast cancer lived without their disease getting worse, pp. 1-3 (Media Release Jul. 15, 2011) http://www.roche.com/media/media_releases/med-cor-2011-07-15.htm.
F. Hoffmann-La Roche Ltd et al., Clinical Study Protocol, Protocol No. WO20698/TOC4129G, RO4368451 Pertuzumab, IND No. BB-IND 9900, Eudract No. 2007-002997-72, Protocol approved Sep. 14, 2007, A Phase III, Randomized, Double-Blind, Placebo-Controlled Clinical Trial to Evaluate the Efficacy and Safety of Pertuzumab + Trastuzumab + Docetaxel vs. Placebo + Trastuzumab + Docetaxel in Previously Untreated HER2-Positive Metastatic Breast Cancer, pp. 1-19 ( Dec. 8, 2011).
F. Hoffmann-La Roche Ltd, "Pertuzumab and Herceptin plus chemotherapy significantly improved the rate of complete tumour disappearance in study of women with newly diagnosed, early-stage HER2-positive breast cancer" (Roche Media Release),:1-4 (Dec. 10, 2010).
Fang, L. et al., "Targeted Therapy in breast cancer: what's new?" Swiss Med Wkly 141( Suppl w13231):1-9 (Jun. 27, 2011).
Fasano et al., "Phase II Evaluation of Liposomal Doxorubicin with Docetaxel in Patients with Metastatic Breast Cancer" Breast Care 5:17-21 ( 2010).
FDA Label for Carboplatin , Jul. 2010, pp. 1-21.
FDA, "FDA Approves TCH Combination for HER2-Positive Early Breast Cancer" 22(5):pp. 1-2 (Jun. 1, 2008).
Fisher et al., "Effect of Preoperative Chemotherapy on the Outcome of Women With Operable Breast Cancer" J Clin Oncol 16(8):2672-2685 ( 1998).
Forbes, J.F., et al., "BCIRG 007: randomized phase III trial of trastuzumab plus docetaxel with or without carboplatin first line in HER2 positive metastatic breast cancer (MBC)" J Clin Oncol (Abstract No. LBA516), 24(18S):1-2 (Jun. 20, 2006).
Franklin, M., et al., "Insights into ErbB Signaling from the Structure of the ErbB2-pertuzumab Complex." Cancer Cell 5(4):317-328 (Apr. 1, 2004).
Fuentes, G., et al., "Synergy between trastuzumab and pertuzumab for human epidermal growth factor 2 (Her2) from colocalization: an in silico based mechanism" Breast Cancer Res 13(3 Suppl R54):1-9 (May 22, 2011).
Galun, E., et al., "Clinical evaluation (phase I) of a combination of two human monoclonal antibodies to HBV: safety and antiviral properties" Hepatology 35(3):673-679 (Mar. 1, 2002).
"Genentech Inc., "Pertuzumab combined with Herceptin and chemotherapy significantly extended the time people with HER2-

(56) References Cited

OTHER PUBLICATIONS positive metastatic breast cancer lived without their disease getting worse"" Press Release:1-7 (Jul. 14, 2011).
Genentech Inc., "Pertuzumab combined with Herceptin and chemotherapy significantly extended the time people with HER2-positive metastatic breast cancer lived without their disease getting worse" (press release retrieved from the Internet Jan. 17, 2013),:1-4 (Jul. 14, 2011) http://www.gene.com/media/press-releases/13547/2011-07-14/pertuzumab-combined-with-herceptin-and-c/.
Genentech, Inc. et al., "Pertuzumab and Herceptin Plus Chemotherapy Significantly Improved the Rate of Complete Tumor Disappearance in Study of Wom" (retrieved from fiercebiotech date redacted),:1-4 (Dec. 10, 2010) https://www.fiercebiotech.com/biotech/pertuzumab-and-herceptin-plus-chemotherapy-significantly-improved-rate-of-complete-tumor.
Genentech, Inc. et al., "Phase III APHINITY Study Shows Genentech's Perjeta® Regimen Helped People with an Aggressive Type of Early Breast Cancer Live Longer without their Disease Returning Compared to Herceptin® and Chemotherapy":1-2 (Mar. 1, 2017) http://www.gene.com/media/press-release/14655/2017-03-01/phase-iii-aphinity-study-shows-genentech.
Genentech, Inc., "A Phase III, Randomized, Double-Blind, Placebo-Controlled Clinical Trial to Evaluate the Efficacy and Safety of Pertuzumab + Trastuzumab + Docetaxel vs. Placebo + Trastuzumab + Docetaxel in Previously Untreated Her2-Positive Metastatic Breast Cancer" (ClinicalTrials Identifier: NCT00567190; view of NCT00567190 on Jan. 1, 2008; retrieved Feb. 7, 2015),:1-4 (Jan. 1, 2008) https://clinicaltrials.gov/archive/NCT00567190/2008_01_01.
Genentech, Inc., "A study to evaluate pertuzumab + trastuzumab + docetaxel vs. placebo + trastuzumab + docetaxel in previously untreated HER2-positive metastatic breast cancer (Cleopatra)" (ClinicalTrials.gov Identifier NCT00567190; First received: Dec. 3, 2007; Last updated: Oct. 24, 2012; Last verified Oct. 2012; Retrieved from internet May 8, 2013),:1-4 http://clinicaltrials.gov/ct2/show/NCT00567190.
Genentech, Inc., et al., "Herceptin® (trastuzumab) Prescribing Information -2008" (U.S. BL 103792/5175 Amendment),:1-11 (Jan. 18, 2008).
Genentech, Inc., "FDA Approves Herceptin for the Adjuvant Treatment of HER2-Positive Node-Positive Breast Cancer" Press Release (Nov. 16, 2006).
Genentech, Inc., 'Genentech reports additional data from biooncology pipeline at ASCO' (press release), pp. 1-2 ( Jun. 1, 2003).
Genentech, Inc., "Perjeta® (pertuzumab)—Annex I: Summary of Product Characteristics" (Marketing Authorisation—EU/1/13/813/001),:1-40 (Mar. 4, 2013).
Geyer et al., "Cardiac Safety analysis of the first stage of NSABP B-31" 26th Annual San Antonio Breast Cancer Symposium (SABCS), Dec. 2003, Abstract 12.
Geyer, C.E., et al., "Lapatinib plus capecitabine for HER2-positive advanced breast cancer" N Eng J Med 355(26):2733-2743 (Dec. 28, 2006).
Gianni et al., "Efficacy and safety of neoadjuvant pertuzumab and trastuzumab in women with locally advanced, inflammatory, or early HER2-positive breast cancer (NeoSphere): a randomised multicentre, open-label, phase 2 trial" Lancet Oncol. 13(1):25-32 (Jan. 2012).
Gianni et al., "Follow-up results of NOAH, a randomized phase III trial evaluating neoadjuvant chemotherapy with Trastuzumab (CT ☐ H) followed by adjuvant H versus CT alone, in patients with HER2-positive locally advanced breast cancer" J Clin Oncol 31( Suppl 15 abstr 503) ( 2013).
Gianni, L., et al., "5-year analysis of neoadjuvant pertuzumab and trastuzumab in patients with locally advanced, inflammatory, or early-stage HER2-positive breast cancer (NeoSphere): a multicentre, open-label, phase 2 randomised trial" Lancet Oncol 17(6):791-800 (Jun. 1, 2016).
Gianni, L., et al., "Neoadjuvant pertuzumab (P) and trastuzumab (H): antitumor and safety analysis of a randomized phase II study ('NeoSphere')" Cancer Res (Abstract S3-2, CTRC-AACR San Antonio Breast Cancer Symposium), 70( Suppl 24):82s (Dec. 15, 2010).
Gianni, L., et al., "P301: Addition of pertuzumab (P) to trastuzumab (H)-based" Breast 70( Suppl S73):1 (Mar. 18, 2011).
Giordano et al., "Clinical progress and the main problems that must be addressed" Breast Cancer Res 5(6):284-288 ( 2003).
Glover, Z.W., et al., "Compatibility and stability of pertuzumab and trastuzumab admixtures in I.V. infusion bags for coadministration" J Pharma Sci 102(3):794-812 (Mar. 1, 2013).
Gnant, M. et al., "Adjuvant endocrine therapy plus zoledronic acid in premenopausal women with early-stage breast cancer: 62-month follow-up from the ABCSG-12 randomised trial, epublished Jun. 4, 2011" Lancet Oncol 12:631-641 (Jun. 4, 2011).
Gnant, M., et al., "Adjuvant endocrine therapy plus zoledronic acid in premenopausal women with early-stage breast cancer: 62-month follow-up from the ABCSG-12 randomised trial" Lancet Oncol 12(7):631-641 (Jul. 1, 2011).
Goldhirsch, A., et al., "Strategies for subtypes-dealing with the diversity of breast cancer: highlights of the St Gallen International Expert Consensus on the Primary Therapy of Early Breast Cancer 2011" Ann Oncol 22(8):1736-1747 (Aug. 1, 2011).
Grignolo, A., et al., "Phase III Trial Failures: Costly, But Preventable" Applied Clin Trials 25(8):1-10 (Aug. 1, 2016).
Grounds for the Decision Opposition for European Patent No. EP2361085B1 dated Oct. 2, 2017, pp. 1-15.
Grounds for the Decision Opposition for European Patent No. EP2752189B1 dated Jan. 7, 2019, pp. 1-68.
"Guidance for Industry—Pathological Complete Response in Neoadjuvant Treatment of High-Risk Early-Stage Breast Cancer: Use as an Endpoint to Support Accelerated Approval" Center for Drug Evaluation and Research:1-16 (May 2012).
Guiu, S., et al., "Long-term follow-up of HER2-overexpressing stage II or III breast cancer treated by anthracycline-free neoadjuvant chemotherapy" Ann Oncol 22(2):321-328 (Feb. 1, 2011).
Hammond et al., ""American Society of Clinical Oncology/College of American Pathologists guideline recommendations for immunohistochemical testing of estrogen and progesterone receptors in breast cancer."" Journal of Clinical Oncology 134:48-72 (Jul. 2010).
Hammond et al., "American Society of Clinical Oncology/College Of American Pathologists guideline recommendations for immunohistochemical testing of estrogen and progesterone receptors in breast cancer." J Clin Oncol. 28(16):2784-95 (Jun. 2010).
Han, H., et al., "5060: Dose-dense docetaxel, carboplatinum and trastuzumab as" Breast Cancer Res TR 106( Suppl S226):1 (Dec. 1, 2007).
Harari, D., et al., "Molecular mechanisms underlying ErbB2/HER2 action in breast cancer" Oncogene 19(53):6102-6114 (Dec. 11, 2000).
Harbeck et al., "Adjuvant chemotherapy for breast cancer" Drug Therapy:1-23 ( 2010).
Harbeck, N., et al., "Primary analysis of KAITLIN: A phase III study of trastuzumab emtansine (T-DM1) + pertuzumab versus rastuzumab + pertuzumab + taxane, after anthracyclines as adjuvant therapy for high-risk HER2-positive early breast cancer (EBC)" J Clin Oncol 38(15):500-500 (May 20, 2020).
Harnett et al., "Diagnosis and treatment of early breast cancer, including locally advanced disease—summary of NICE guidance." BMJ 338:598-600 ( 2009).
Healey Bird, B. et al., "Cardiac Toxicity in Breast Cancer Survivors: Review of Potential Cardiac Problems" Clin Cancer Res:14-24 (Jan. 1, 2008).
Heinzlef et al., "Severe neuropathy after high dose carboplatin in three patients receiving multidrug chemotherapy" J Neurol Neurosurg Psychiatry 64:667-669 ( 1998).
Helwick, "ALTTO Trial Finds Dual Anti-HER2 Therapy No Better Than Trastuzumab Alone" ASCO (Printed Jan. 7, 2022 <https://ascopost.com/issue5/june-10-2014/altto-trial-finds-dual-anti-her2-therapy-no-better-than-trastuzumab-alone>), ( 2014).
Hernández-Ledesma, B. et al., "Lunasin, a novel seed peptide for cancer prevention" Peptides 30(2):426-430 (Feb. 1, 2009).
"Herzuma Leaflet":1-29 (Dec. 21, 2021).

(56) References Cited

OTHER PUBLICATIONS

Hoffmann-La Roche, "A Study of Pertuzumab in Combination With Herceptin (Trastuzumab) and Vinorelbine in First Line in Patients With Metastatic or Locally Advanced HER2-Positive Breast Cancer" (ClinicalTrials.gov identifier NCT01565083, Study ID MO27782, First received Mar. 26, 2012, Last updated May 12, 2014, Last verified May 2014, retrieved May 15, 2014),:1-3 (May 2014) http://clinicaltrials.gov/ct2/show/NCT01565083?term=MO27782&rank=1.

Hoffmann-La Roche, "A Study of Pertuzumab in Combination With Herceptin and Chemotherapy in Patients With HER2-Positive Breast Cancer" (Clinical Trials Identifier: NCT00976989: view of NCT00976989 on Nov. 16, 2009; retrieved on May 31, 2015); 1-3 (Nov. 16, 2009) https://clinicaltrials.gov/archive/NCT00976989/2009_11_16.

"How Do I Use Prescription Diug Labeling" US Food and Drug Adminstration (FDA) https://www.fda.gov/about-fda/oncology-center-excellence/how-do-i-use-prescription-drug-labeling, last updated:1-3 (Mar. 29, 2023).

Humphreys et al., "Gemcitabine-associated thrombotic microangiopathy" Cancer 100(12):2664-2670 ( 2004).

Huober et al., "Higher efficacy of letrozole in combination with trastuzumab compared to letrozole monotherapy as first-line treatment in patients with HER2-positive, hormone-receptor-positive metastatic breast cancer—Results of the eLEcTRA trial" The Breast 21:27-33 ( 2012).

Hurvitz, S. et al., "Neoadjuvant Trastuzumab Emtansine and Pertuzumab in Human Epidermal Growth Factor Receptor 2-Positive Breast Cancer: Three-Year Outcomes From the Phase III Kristine Study" Journal of Clinical Oncology 37(25):1-17 (Jun. 3, 2019).

Hurvitz, S., et al., "Neoadjuvant trastuzumab, pertuzumab, and chemotherapy versus trastuzumab emtansine plus pertuzumab in patients with HER2-positive breast cancer (Kristine): a randomised, open-label, multicentre, phase 3 trial" Lancet Oncol 19(1):115-126 (Jan. 1 , 2018).

Inoue, M., et al., "Epidemiology of Gastric Cancer in Japan" Postgrad Med J 81(957):419-424 (Jul. 1, 2005).

Jahanzeb, M, "Adjuvant Trastuzumab Therapy for HER2-Positive Breast Cancer" Clinical Breast Cancer 8(4):324-333 (Aug. 2008).

Jayaram, A., et al., "Neoadjuvant Trastuzumab, Docetaxel, and Carboplatin (TCH) for human epidermal growth factor receptor-2 (Her-2) positive breast cancer: pathological tumour response rates in an Irish teaching hospital" Ann Oncol 21( Suppl 8):1 (Oct. 1, 2010).

Joensuu, H. et al., "Fluorouracil, Epirubicin, and Cyclophosphamide With Either Docetaxel or Vinorelbine, With or Without Trastuzumab, as Adjuvant Treatments of Breast Cancer: Final Results of the FinHer Trial" Journal of Clinical Oncology 27(34):5685-5692 (Dec. 1, 2009).

Joensuu, H., et al., "Adjuvant docetaxel or Vinorelbine with or without trastuzumab for breast cancer" N Eng J Med 354(8):809-820 (Feb. 23, 2006).

Kaufmann et al., "Recommendations From an International Expert Panel on the Use of Neoadjuvant (Primary) Systemic Treatment of Operable Breast Cancer: An Update" J Clin Oncol 24:1940-1949 (2006).

Ekaye, S.B., et al., "A randomised Phase II study evaluating the combination of carboplatin-based chemotherapy with pertuzumab (P) versus carboplatin-based therapy alone in patients with relapsed, platinum sensitive ovarian cancer" Slides (American Society of Clinical Oncology (ASCO) 44th Annual Meeting, May 30-Jun. 3, 2008) American Society of Clinical Oncology (ASCO), Chicago, IL, pp. 1-16 ( May 30, 2008).

Kaye, S.B., et al., "A randomised phase II study evaluating the combination of carboplatin-based chemotherapy with pertuzumab (P) versus carboplatin-based therapy alone in patients with relapsed, platinum sensitive ovarian cancer" J Clin Oncl (Abstract 5520, Retrieved Mar. 31, 2013), 26( Suppl 15S):1-2 (May 20, 2008) http://meeting.ascopubs.org/cgi/content/abstract/26/15_suppl/5520?sid=482d7d8a-4bfd-49.

Kaye, S.B., et al., "A randomised Phase II study evaluating the combination of carboplatin-based chemotherapy with pertuzumab (P) versus carboplatin-based therapy alone in patients with relapsed, platinum sensitive ovarian cancer" Poster ASCO, Chicago, IL, USA, pp. 1 ( Spring May 30-Jun. 3, 2008).

Kaye, S.B., et al., "A randomized phase II study evaluating the combination of carboplatin-based chemotherapy with pertuzumab versus carboplatin-based therapy alone in patients with relapsed, platinum-sensitive ovarian cancer" Ann Oncol 24(1):145-152 ( 2013).

Kelley, J.R., et al., "Gastric cancer epidemiology and risk factors" J Clin Epidemiol 56(1):1-9 (Jan. 1, 2003).

Koh, J., et al., "Introduction of a New Staging System of Breast Cancer for Radiologists: An Emphasis on the Prognostic Stage" Korean J Radiol 20(1):69-82 (Jan. 1, 2019).

Kola et al., "Can the pharmaceutical industry reduce attrition rates?" Nat Rev Drug Discov 3(8):711-715 (Aug. 2004).

Kolberg, H.C., et al., "Neoadjuvant Chemotherapy with Docetaxel, Carboplatin and Weekly Trastuzumab Is Active in HER2-Positive Early Breast Cancer: Results after a Median Follow-Up of over 4 Years" Breast Care (Basel) 11(5):323-327 (Oct. 11, 2016).

Kolberg, H.C., et al., "P304 Docetaxel, carboplatin and weekly trastuzumab are active as neoadjuvant therapy in operable HER2-positive breast cancer" Breast 20(6 Suppl 1, S74 Poster):1 (Mar, 18, 2011).

Komenaka, I., et al., "Immunotherapy for melanoma" Clin Dermatol 22(3):251-265 (May 31, 2004).

Konecny et al., "Docetaxel and trastuzumab: A Combination With Clinical Relevance" Onkologie 23(Suppl 6):7-9 ( 2000).

Korean Pharmacology Association Pharmacology "Chapter 57: Drug Resistance" (Concise explanation in English attached.), Seoul, KR:Korean Pharmacology Association,:1-39 ( 2009).

Kurosumi, "Significance of Histopathological Evaluation in Primary Therapy for Breast Cancer—Recent Trends in Primary Modality with Pathological Complete Response (pCR) as Endpoint" Breast Cancer 11(2):139-147 ( 2004).

Lee-Hoeflich, S., et al., "A central role for HER3 in HER2-amplified breast cancer: implications for targeted therapy" Cancer Res 68(14):5878-5887 (Jul. 15, 2008).

Lemieux, J., et al., "The role of neoadjuvant her2-targeted therapies in her2-overexpressing breast cancers" Curr Oncol 16(5):48-57 (Sep. 1, 2009).

Lenihan, D. et al., "Pooled analysis of cardiac safety in patients with cancer treated with Pertuzumab, e-published Jun. 10, 2011" Annals of Oncology 23(3):791-800 (Jun. 10, 2011).

Lenihan, D., et al., "Pooled analysis of cardiac safety in patients with cancer treated with pertuzumab" Ann Oncol 23(3):791-800 (Mar. 1, 2012).

Leonessa, et al., "The Biology of Breast Tumor Progression: Acquisition of hormone independence and resistance to cytotoxic drugs" Acta Oncologica 31(2):115-123 ( 1992).

Loi, S., "Fine-tuning chemotherapy in the era of dual HER2 targeting" Lancet Oncl 19(12):1551-1554 (Dec. 1, 2018).

Macagno, A., et al., "Isolation of Human Monoclonal Antibodies that Potently Neutralize Human Cytomegalovirus Infection by Targeting Different Epitopes on the gH/gL/UL128-131A Complex" J Virol 84(2):1005-1013 (Jan. 1, 2010).

Mackey et al., "Cardiac management during adjuvant trastuzumab therapy: recommendations of the Canadian Trastuzumab Working Group" Curr Onc 15(1):24-35 ( 2008).

Malik, M.A., et al., "Dose-Response Studies of Recombinant Humanized Monoclonal Antibody 2C4 (Pertuzumab) in Tumor Xenograft Models" Poster (No. 773) American Association for Cancer Research, Washington, D.C.—USA, pp. 1 ( Jul. 11-14, 2003).

Malik, M.A., et al., "Dose-Response Studies of Recombinant Humanized Monoclonal Antibody 2C4 in Tumor Xenograft Models" P Am Assoc Canc Res (Abstract No. 773), 44:150 (Jul. 2003).

Mamounas, E., et al., "Preoperative (neoadjuvant) chemotherapy in patients with breast cancer" Semin Oncol 28(4):389-399 (Aug. 1, 2001).

Mancini et al., "Chemotherapy Administration Sequence: A Review of the Literature and Creation of a Sequencing Chart" J Hematol Oncol Pharm 1(1):17-25 (2011).

(56) References Cited

OTHER PUBLICATIONS

Martin, M., et al., "Adjuvant docetaxel for node-positive breast cancer" N Eng J Med 352(22):2302-2313 (Jun. 2, 2005).
Marty, M., et al., "Randomized phase II trial of the efficacy and safety of trastuzumab combined with docetaxel in patients with human epidermal growth factor receptor 2-positive metastatic breast cancer administered as first-line treatment: the M77001 study group" J Clin Oncol 23(19):4265-4274 (Jul. 1, 2005).
McWhinney et al., "Platinum neurotoxicity pharmacogenetics" Mol Cancer Ther 8(1):10-16 ( 2009).
Meetings of the Oral Proceedings for European Patent Application No. 12778010.4 dated Feb. 28, 2022, 9 Pages.
Meric-Bernstam, F., et al., "Advances in targeting human epidermal growth factor receptor-2 signaling for cancer therapy" Clin Cancer Res 12(21):6326-6330 (Nov. 1, 2006).
Merriam Webster Thesaurus Entry for Concomitant (Printed Oct. 7, 2011) pp. 1.
Metivier et al., "Pathophysiology of Anemia: Focus on the Heart and Blood Vessles" Nephrol Dial Transplant 15( Suppl 3):14-18 ( 2000).
MFDS Regulatory Provision for examining Drug Approval Applications. Concise explanation in English attached., pp. 1-61 (2011).
Moy et al., "Bosutinib and exemestane (EXE) versus EXE alone in postmenopausal (postm) women with hormone receptor-positive (HR+) HER2-negative (HER2-) advanced breast cancer (ABC)." J Clin Oncol 29(15):631 (2011).
Muss, H., et al., "Adjuvant Chemotherapy in Older Women with Early-Stage Breast Cancer" N Engl J Med 360(20):2055-2065 (May 14, 2009).
Nabholtz, J., et al., "Results of two open label Multicentre phase II pilot studies with Herceptln in combination with docetaxel and platinum" Eur J Cancer 37( Suppl S6):S190 (Apr. 1, 2001).
Nahta, R. et al., "The HER-2-targeting antibodies trastuzumab and pertuzumab synergistically inhibit the survival of breast cancer cells" Cancer Res 64(7):2343-2346 (Apr. 1, 2004).
Nahta, R., et al., "Growth factor receptors in breast cancer: potential for therapeutic intervention" Oncologist 8(1):5-17 (Jan. 1, 2003).
Narod et al., "Are two-centimeter breast cancers large or small?" Current Oncology 20(4):205-211(Aug. 2013).
Naruki, Y., et al., "Radioimmunodetection of cancer of gastrointestinal tract and liver metastasis with I-131 anti-CEA and I-131 anti-CA19-9 monoclonal antibody cocktail (IMACIS-1)" Ann Nucl Med 8(3):163-169 (Aug. 1, 1994).
National Cancer Institute (NCI), "Hazard Ratio" The Wayback Machine (Definition of hazard ratio printed on Apr. 13, 2023),:p. 1 http://web.archive.org/web/20110727141129/http://www.cancer.gov/dictionary?CdrID=618612.
NCBI Database, X03363, (Genebank accession No. X03363 https://www.ncbi.nlm.nih.gov/nuccore/X03363; retrieved from the internet on Dec. 12, 2023), pp. 1-3, Mar. 30, 1995.
NCCN—National Comprehensive Cancer Network, "Clinical Practice Guidelines in Oncology: Breast Cancer" NCCN—National Comprehensive Cancer Network (National Comprehensive Cancer Network, NCCN Clinical Practice Guidelines in Oncology, Breast Cancer, version 2.2011), 2011(2):1-148 (Mar. 25, 2011).
NCCN—National Comprehensive Cancer Network, "Clinical Practice Guidelines in Oncology: Gastric Cancer" NCCN—National Comprehensive Cancer Network 1(2006):1-26 (Mar. 3, 2006).
NCI Thesaurus Results for "Multigated Acquisition Scan" Released Jun. 30, 2022 pp. 1.
NCI Thesaurus Results for "Radionuclide Ventriculography" Released Aug. 30, 2021 pp. 1.
Neoadjuvant Trastuzumab in Patients with HER-2 Positive Locally Advanced Breast Cancer, ISRCT Registry, pp. 1-7 (Last Edited Mar. 15, 2010).
"Neoadjuvant Treatment of Early Breast Cancer, A Conversation With FDA's Office of Hematology and Oncology Products" The ASCO Post Staff:1-5 (Nov. 15, 2013).
NIH—National Cancer Institute et al., "NCI Dictionary of Cancer Terms—Early Breast Cancer":1 https://www.cancer.gov/publications/dictionaries/cancer-terms/def/early-stage-breast-cancer, Printed on Oct. 20, 2020.
NIH—National Cancer Institute, "NCI Dictionary of Cancer Terms—Visceral" https://www.cancer.gov/publications/dictionaries/cancer-terms/def/visceral, Printed on Aug. 22, 2022.
Ogston et al., "A new histological grading system to assess response of breast cancers to primary chemotherapy: prognostic significance and survival" The Breast 12( Suppl 320-327) ( 2003).
Oken et al., "Toxicity and response criteria of the Eastern Cooperative Oncology Group" Am J Clin Oncol 5:649-655 ( 1982).
Olayioye, M. et al., "The ErbB Signaling Network: Receptor Heterodimerization in Development and Cancer" EMBO J 19(13):3159-3167 (Jul. 3, 2000).
Outhoff, "The art of prescribing trastuzumab for HER2- positive breast cancer" Southern African Journal of Gynaecological Oncology 3(1):16-26 (2011).
Paik, S. et al., "Successful quality assurance program for HER2 testing in the NSABP Trial for Herceptin" Abstract (76(S1):S31,) San Antonio Breast Cancer Symposium, San Antonio, Texas—USA, pp. 1 ( Dec. 10-14, 2002).
Paik, S., et al., "HER2 and choice of adjuvant chemotherapy for invasive breast cancer: National Surgical Adjuvant Breast and Bowel Project Protocol B-15" J Natl Cancer Inst 92(24):1991-1998 (Dec. 20, 2000).
Paik, S., et al., "Real-World Performance of HER2 Testing—National Surgical Adjuvant Breast and Bowel Project Experience" J Natl Cancer Inst 94(11):852-854 (Jun. 5, 2002).
Paraplatin (carboplatin) United States Prescribing Information (USPI),:1-21 (Jul. 2010).
Parker et al., "Impact of Biomarkers on Clinical Trial Risk in Breast Cancer, published online" Breast Cancer Research and Treatment 136:179-185 (Sep. 25, 2012).
Parkin, D., "International Variation" Oncogene 23(38):6329-6340 (Aug. 1, 2004).
Paul et al., Fundamental Immunology, 3rd ed. Raven Press, NY, Chap. 9:292-295 (Oct. 15, 2019).
Paul, W.E. Fundamental Immunology ((under the heading of) Fv Structure and Diversity in Three Dimensions), 3rd edition,:292-295 ( 1993).
Pegram, M., "Breast cancer: review of platinum-based cooperative group trials" J Natl Compr Canc Netw( Suppl S2):S2-S9 (Sep. 1, 2004).
Pegram, M., et al., "Rational combinations of trastuzumab with chemotherapeutic drugs used in the treatment of breast cancer" J Natl Cancer Inst 96(10):739-749 (May 19, 2004).
Pegram, M., et al., "Results of Two Open-Label, Multicenter Phase II" J Natl Cancer Inst 96(10):759-769 (May 19, 2004).
Penault-Llorca et al., "Comparison of the prognostic significance of Chevallier and Sataloff's pathologic classifications after neoadjuvant chemotherapy of operable breast cancer" Hum Pathol 39:1221-1228 (2008).
Perez et al., "Interim cardiac safety analysis of NCCTG N9831 Intergroup adjuvant trastuzumab trial" Proceedings of the American Society of Clinical Oncology: Abstract 556, (2005).
Perez, E. et al., "Trastuzumab Emtansine With or Without Pertuzumab Versus From Marianne Receptor 2-Positive Advanced Breast Cancer: Final Results Trastuzumab With Taxane for Human Epidermal Growth Factor" Wiley Online Library:3974-3984 (Jul. 18, 2019).
Perez, E. et al., "Trastuzumab Emtansine With or Without Pertuzumab Versus Trastuzumab Plus Taxane for Human Epidermal Growth Factor Receptor 2-Positive, Advanced Breast Cancer: Primary Results From the Phase III Marianne Study" Journal of Clinical Oncology 35(2):141-158 (Jan. 10, 2017).
Perez, E. et al., "Trastuzumab Plus Adjuvant Chemotherapy for Human Epidermal Growth Factor Receptor 2-Positive Breast Cancer: Planned Joint Analysis of Overall Survival From NSABP B-31 and NCCTG N9831" Journal of Clinical Oncology 32(33):3744-3753 (Nov. 20, 2014).
Perez, E., et al., "A combination of pertuzumab, trastuzumab, and vinorelbine for first-line treatment of patients with HER2-positive metastatic breast cancer: An open-label, two-cohort, phase II study

(56) References Cited

OTHER PUBLICATIONS (Velvet)" J Clin Oncol (2012 ASCO Annual Meeting, suppl. abstr TPS653, Retrieved Mar. 13, 2013), 30(15 Suppl 1):1 (May 30, 2012) http://meetinglibrary.asco.org/content/93917-114.
"Perjeta (Pertuzumab) Prescribing Information, Revised":1-24 (Sep. 2013).
"Perjeta (Pertuzumab) Prescribing Information, Revised":1-36 (Feb. 2021).
Perjeta, "Pertuzumab (Perjeta) United States Prescribing Information (USPI)":1-14 (Jun. 2012) https://www.accessdata.fda.gov/drugsatfda_docs/label/2012/125409lbl.pdf.
Perjeta, "Pertuzumab (Perjeta) United States Prescribing Information (USPI),":1-36 (Jan. 2020)—Pertuzumab (Perjeta) United States Prescribing Information (USPI).
Perjeta, "Pertuzumab (Perjeta) United States Prescribing Information (USPI),":1-36 (Feb. 2021)—Pertuzumab (Perjeta) United States Prescribing Information (USPI).
Perjeta® (pertuzumab) Full Prescribing Information, pp. 1-15 (revised Jun. 2012).
Perjeta® (pertuzumab) Full Prescribing Information, pp. 1-16 (revised Apr. 2013).
"Pertuzumab Combined With Herceptin and Chemotherapy Significantly Extended the Time People With HER2-Positive Metastatic" Fiercepharma:1-4 (Jul. 15, 2011).
"Pertuzumab SmPC":1-31 ( 2013).
"Pertuzumab Summary of Product Characteristics (SmPC)":1-43 ( 2022).
Pharmacology Review et al., "BLA File No. 125409—Perjeta (Pertuzumab)" Center for Drug Evaluation & Res (Report of Dr. John K. Leighton, Acting Dir. DABT—Division of Hematology Oncology Toxicology, Office of Hematology & Oncology Products, Application No. 125409ORIG1s000; Ref. ID. 3131984),:1-51 (May 16, 2012).
Phase III Aphinity Study Shows Genentech's Perjeta® Regimen Helped People with an Aggressive Type of Early Breast Cancer Live Longer without their Disease Returning Compared to Herceptin® and Chemotherapy, pp. 1-11 ( Mar. 1, 2017) http://www.gene.com/media/press-release/14655/2017-03-01/phase-iii-aphinity-study-shows-genentech.
Piccart et al., "Adjuvant Pertuzumab and Trastuzumab in Early HER2-Positive Breast Cancer in the Aphinity Trial: 6 Years' Follow-Up" J Clin Oncol 39( Suppl 1448-1457) ( 2021).
Piccart-Gebhart, M. et al., "First results from the phase III Altto trial (BIG 2-06; NCCTG [Alliance] N063D) comparing one year of anti-HER2 therapy with lapatinib alone (L), trastuzumab alone (T), their sequence (T→L), or their combination (T+L) in the adjuvant treatment of HER2-positive early breast cancer (EBC)" Journal of Clinical Oncology (abstr LBA4; 2014 ASCO Annual Meeting II), 32( Suppl 18):1-4 (2014).
Pinkas-Kramarski, R., et al., "Diversification of neu differentiation factor and epidermal growth factor signaling by combinatorial receptor interactions" EMBO J 15(10):2452-2467 (May 15, 1996).
Pishvaian, M. et al., "A global, multicenter phase II trial of lapatinib plus capecitabine in gastric cancer" J Clin Oncol (Abstract 88), 29(4):1-2 (Feb. 1, 2011).
Plummer, M., et al. Mechanisms of carcinogenesis: contributions of molecular epidemiology "Epidemiology of gastric cancer" (IARC Scientific Publications No. 157), Buffler et al., Lyon, France:International Agency for Research on Cancer,:311-326 ( 2004).
Poole, C.J., et al., "Epirubicin and cyclophosphamide, methotrexate, and fluorouracil as adjuvant therapy for early breast cancer" N Eng J Med 355(18):1851-1862 (Nov. 2, 2006).
Portera, C.C., et al., "A report of cardiac events in a phase II clinical study using trastuzumab combined with pertuzumab in HER2-positive metastatic breast cancer (MBC)" J Clin Oncol (Abstract No. 1028 (2007 ASCO Annual Meeting)), 25(18S):1028 (Jun. 20, 2007).
Portera, C.C., et al., "Cardiac toxicity and efficacy of trastuzumab combined with pertuzumab in patients with Trastuzumab-insensitive human epidermal growth factor receptor 2-positive metastatic breast cancer" Clin Cancer Res 14(9):2710-2716 (May 1, 2008).
Portolano, S., et al., "Lack of promiscuity in autoantigen-specific H and L chain combinations as revealed by human H and L chain 'roulette'" J Immunol 150(3):880-887 (Feb. 1, 1993).
Putti et al., "Estrogen receptor-negative breast carcinomas: a review of morphology and immunophenotypical analysis" Modern Pathology 18(1):26-35 (Jan. 2005).
Qin et al., "Clinicopathologic characteristics and prognostic factors for HER2-positive patients with metastatic breast cancer in southern China" Arch Med Sci . 11(3):544-550 ( 2013).
Quartino, A., et al., "Population pharmacokinetic and exposure-response analysis for trastuzumab administered using a subcutaneous 'manual syringe' injection or intravenously in women with HER2-positive early breast cancer" Cancer Chemother Pharmacol 77:77-88 (Jan. 1, 2016).
Rastogi, P., et al., "Preoperative chemotherapy: updates of National Surgical Adjuvant Breast and Bowel Project Protocols B-18 and B-27" J Clin Oncol 26(5):778-785 (Feb. 10, 2008).
Reichert et al., "Development trends for new cancer therapeutics and vaccines" Drug Discovery Today 13(1):30-37 ( 2008).
Riese II, D.J., et al., "The cellular response to neuregulins is governed by complex interactions of the erbB receptor family" Mol Cell Biol (published erratum appears in Mol Cell Biol 16(2): 735 (1996)), 15(10):5770-5776 (Oct. 1, 1995).
Robert, N.J., et al., "BCIRG 006: Docetaxel and trastuzumab-based regimens improve DFS and OS over AC-T in node positive and high risk node negative HER2 positive early breast cancer patients: Quality of life (QOL) at 36 months follow-up" J Clin Oncl (Abstract 19647, Retrieved May 21, 2014), 25(18S Suppl Jun. 20):1 (Jun. 20, 2007) http://meeting.ascopubs.org/cgi/content/short/25/18_suppl/19647.
Robert, N.J., et al., "Randomized phase III study of trastuzumab, paclitaxel, and carboplatin compared with trastuzumab and paclitaxel in women with HER-2-overexpressing metastatic breast cancer" J Clin Oncol 24(18):2786-2792 (Jun. 20, 2006).
Roche et al., "Concordance between local and central laboratory HER2 testing in the breast intergroup trial N9831" J Natl Cancer Inst. 94(11):855-7 ( 2002).
Roche, "First Quarter-Q1 2011 Sales":1-126 (Apr. 14, 2011).
Roche, "Investor Update—2010" (Last Updated: Dec. 10, 2010; Printed: Dec. 16, 2019),:1-6 (Dec. 10, 2010) https://www.roche.com/investors/updates.
Roche, "Late-stage Pipeline Update 2010":1-98 (Dec. 9, 2010).
Roche, "Nine Months YTD 2011 Sales":1-142 (Oct. 13, 2011).
Roche, "Roche Annual Report 2018":1-160 (Jan. 2019).
Roche, "Roche Annual Report":1-220 ( 2022).
Roche, "Roche to present important new data for HER2-positive breast cancer at 2011 San":1-4 (Nov. 30, 2011) https://www.roche.com/dam/jcr:e32f53c2-251c-4432-8bf6-32fa5efc0764/en/med-cor-2011-11-30.
Romond, E.H., et al., "Trastuzumab plus adjuvant chemotherapy for operable HER2-positive breast cancer" N Eng J Med 353(16):1673-1684 (Oct. 20, 2005).
Rudikoff, S., et al., "Single amino acid substitution altering antigen-binding specificity" PNAS USA 79(6): 1979-1983 (Mar. 1, 1982).
Rugo, "Highlights in Breast Cancer from the 2016 American Society of Clinical Oncology Annual Meeting" Clinical Advances in Hematology & Oncology 14(7):494-497 (Jul. 1, 2016).
Saboo, A., "Pertuzumab and Herceptin plus chemotherapy significantly improved the rate of complete tumor disappearance in study of wom" FierceBiotech (retrieved Oct. 30, 2015),:1-5 (Dec. 10, 2010) http://www.fiercebiotech.com/node/96166/print.
Saboo, A., "Pertuzumab combined with Herceptin and chemotherapy significantly extended the time people with HER2-positive metastatic B" FierceBiotech (retrieved Oct. 30, 2015),:1-5 (Jul. 15, 2011) http://http://www.fiercebiotech.com/node/139289/print.
Saiyed et al., "Hematological Toxicities Associated with Pazopanib Use in Cancer Patients: A Meta-Analysis" Value in Health 18(7):1-4 ( 2015).

(56) References Cited

OTHER PUBLICATIONS

Saloustros et al., "Vinorelbine metronomic plus bevacizumab as salvage therapy for patients with metastatic breast cancer (MBC): A multicenter phase II study." J Clin Oncol 28(15):1133 ( 2010).
Scheuer, W., et al., "Strongly enhanced antitumor activity of trastuzumab and pertuzumab combination treatment on HER2-positive human xenograft tumor models" Cancer Res 69(24):9330-9336 (Dec. 15, 2009).
Schiffman, M., et al., "The Promise of Global Cervical-Cancer Prevention" N Engl J Med 353(20):2101-2104 (Nov. 17, 2005).
Schilsky et al., "Success and pitfalls of targeted therapy combinations" Eur J Cancer 8(7):16-17 (2010).
Schmidinger et al., "Cardiac Toxicity of Sunitinib and Sorafenib in Patients With Metastatic Renal Cell Carcinoma" J Clin Oncol 26(52):5204-5212 ( 2008).
Schneeweiss et al., "Biomarker (BM) analyses of a Phase II study of neoadjuvant pertuzumab and trastuzumab with and without anthracycline (ATC)-containing chemotherapy for treatment of HER2-positive early breast cancer (BC) (Tryphaena)" Annals of Oncology (Abstract 202P), 23( Suppl 9):1 (Sep. 2012).
Schneeweiss et al., "Neoadjuvant pertuzumab and trastuzumab concurrent or sequential with an anthracycline-containing or concurrent with an anthracycline-free standard regimen: a randomized phase II study (Tryphaena)" Cancer Research (Abstract S5-6), 71(24 Suppl 3):1-3 (Dec. 15, 2011).
Schneeweiss, A. et al., "Pertuzumab plus trastuzumab in combination with standard neoadjuvant anthracycline-containing and anthracycline-free chemotherapy regimens in patients with HER2-positive early breast cancer: a randomized phase II cardiac safety study (Tryphaena)" Ann Oncol (With Supplementary Figure S1 and Supplementary Tables S2-S7), 24(9):2278-2284 ( 2013).
Schneeweiss, A., et al., "Long-term efficacy analysis of the randomised, phase II Tryphaena cardiac safety study: Evaluating pertuzumab and trastuzumab plus standard neoadjuvant anthracycline-containing and anthracycline-free chemotherapy regimens in patients with HER2-positive early breast cancer" Eur J Cancer 89:27-35 (Jan. 1, 2018).
Schneeweiss, A., et al., "Pertuzumab plus trastuzumab in combination with standard neoadjuvant anthracycline-containing and anthracycline-free chemotherapy regimens in patients with HER2-positive early breast cancer: a randomized phase II cardiac safety study (Tryphaena)" Ann Oncol 24(9):2278-2284 (Sep. 1, 2013).
Semba et al., "A v-erbB-related protooncogene, c-erbB-2, is distinct from the c-erbB-1/epidermal growth factor-receptor gene and is amplified in a human salivary gland adenocarcinoma" P Natl Acad Sci USA 82:6497-6501 (Oct. 1985).
Shin, S.G., et al., "New Drug Application Process" J Korean Soc Clin Pharmacol Ther (Concise explanation in English attached.), 9(2):127-136 (Dec. 1, 2001).
Singh et al., "Phase II Trial of RAD001 Plus Carboplatin in Patients with Triple-Negative Metastatic Breast Cancer" J Clin Oncol 29(27 Suppl 1):293 ( 2011).
Singh, J.C., et al., "Pathologic Complete Response with Neoadjuvant Doxorubicin and Cyclophosphamide Followed by Paclitaxel with Trastuzumab and Pertuzumab in Patients with HER2-Positive Early Stage Breast Cancer: A Single Center Experience" Oncologist 22(2):139-143 (Feb. 1, 2017).
Slamon et al., "Human Breast Cancer: Correlation of Relapse and Survival with Amplification of the hHER-2/new Oncogene" Science 9:177-192 ( 1987).
Slamon, D., et al., "Adjuvant trastuzumab in HER2-positive breast cancer" N Engl J Med 365(14):1273-1283 (Oct. 6, 2011).
Slamon, D., et al., "Use of chemotherapy plus a monoclonal antibody against HER2 for metastatic breast cancer that overexpresses HER2" New Engl J Med 344(11):783-792 (Mar. 15, 2001).
Slamon, et al., "Supplementary Appendix—Adjuvant trastuzumab in HER2-positive breast cancer" N Engl J Med:1-16 (Oct. 12, 2011).
Sliwkowski, M.X., "Ready to Partner" Nat Struct Bio 10(3):158-159 (Mar. 1, 2003).

Soerjomataram et al., "An overview of prognostic factors for long-term survivors of breast cancer" Breast Cancer Research and Treatment 107:309330 ( 2008).
Sonnenblick, A. et al., "Adjuvant systemic therapy in breast cancer: quo vadis?" Annals of Oncology (Published online, Received Dec. 1, 2014; revised Feb. 9, 2015; accepted Feb. 16, 2015), 26:1629-1634 (Feb. 23, 2015).
Specifications Manual for Joint Commission of National Quality Core Measures, pp. 1-4, accessed Oct. 11, 2021 (Published 2010).
Sreedhara, A., et al., "Stability of IgG1 monoclonal antibodies in intravenous infusion bags under clinical in-use conditions" J Pharma Sci 101(1):21-30 (Jan. 1, 2012).
Steffensen, K.D., et al., "Protein levels and gene expressions of the epidermal growth factor receptors, HER1, HER2, HER3 and HER 4 in benign and malignant ovarian tumors" Int J Oncol 33(1):195-204 (Jul. 1, 2008).
Swain, S.M., et al., "Pertuzumab, trastuzumab, and docetaxel in HER2-positive metastatic breast cancer" N Engl J Med 372(8):724-734 (Feb. 19, 2015).
Tabaries, S. et al., "Chapter 10: Breast Cancer Liver Metastasis" Liver Metastasis: Biology and Clinical Management:273-303 (Jan. 1, 2011).
Tanner, B., et al., "ErbB-3 predicts survival in ovarian cancer" J Clin Oncol 24(26):4317-4323 (Sep. 10, 2006).
The ATAC Trialists' Group, "Anastrozole alone or in combination with tamoxifen versus tamoxifen alone for adjuvant treatment of postmenopausal women with early breast cancer: first results of the ATAC randomised trial" Lancet 359(9324):2131-2139 (Jun. 22, 2002).
Therasse et al., "New guidelines to evaluate the response to treatment in solid tumors" J Natl Cancer Institute 92(3):205-216 ( 2000).
Thirumaran, R., et al. Cancer Immunotherapy: Immune Suppression and Tumor Growth "Charpter 7: Cytotoxic Chemotherapy in Clinical Treatment of Cancer" George Prendergast, Elizabeth Jaffee, eds., 1st edition, New York, NY US:Academic Press—Elsevier,:102-116 (Jul. 4, 2007).
Tiersten et al., "A phase I trial of dose-dense (biweekly) carboplatin combined with paclitaxel and pegfilgrastim: A feasibility study in patients with untreated Stage III and IV ovarian, tubal or primary peritoneal cancer: A Gynecologic Oncology Group study" Gynecol Oncol 118:303-307 ( 2010).
Tiwari, S., et al., "Retrospective study of the efficacy and safety of neoadjuvant docetaxel, carboplatin, trastuzumab/pertuzumab (TCH-P) in nonmetastatic HER2-positive breast cancer" Breast Cancer Res Treat 158(1):189-193 (Jul. 1, 2016).
"Trastuzumab (Herceptin) United States Prescribing Information (USPI),":1-38 (Nov. 2018)—Trastuzumab (Herceptin) United States Prescribing Information (USPI).
"Trastuzumab (Herceptin) United States Prescribing Information (USPI),":1-33 (Oct. 2010)—Trastuzumab (Herceptin) United States Prescribing Information (USPI).
"Trastuzumab (Herceptin) United States Prescribing Information (USPI),":1-38 (Apr. 2017)—Trastuzumab (Herceptin) United States Prescribing Information (USPI).
United Kingdom—Health Research Authority [HRA] et al., "BO22280 Pertuzumab + Trastuzumab in HER2+ Early BC (NeoAdjuvant)" (BO22280 Pertuzumab + Trastuzumab in HER2+ Early BC (NeoAdjuvant); IRAS ID 27700; REC reference 09/H0504/106; First Posted: Sep. 17, 2009: Last Update Posted: Sep. 17, 2009: Printed: Feb. 12, 2020),:1-4 https://www.hra.nhs.uk/planning-and-improving-research/application-summaries/research-summaries/bo22280-pertuzumab-trastuzumab-in-her2-early-bc-neoadjuvant/.
Untch et al., "Current and future role of neoadjuvant therapy for breast cancer" The Breast 23:526-537 (2014).
Untch et al., "Nab-paclitaxel versus solvent-based paclitaxel in neoadjuvant chemotherapy for early breast cancer (GeparSepto—GBG 69): a randomised, phase 3 trial" www.thelancet/oncology 17:345-356 (Mar. 2016).
Untch, "Dose-Dense Therapy" Breast Care 3:134-138 (Apr. 25, 2008).
Untch, M., "Targeted Therapy for Early and Locally Advanced Breast Cancer" Breast Care 5(3):144-152 (Jun. 1, 2010).

(56) References Cited

OTHER PUBLICATIONS

US ClinicalTrails.gov., A Dose-Finding Study of Pertuzumab (Perjeta) in Combination With Trastuzumab (Herceptin) in Healthy Male Participants and Women With Early Breast Cancer (EBC) (ClinicalTrials.gov Identifier NCT02738970; Study ID: BO30185; First Posted Apr. 14, 2016; Last Updated Posted Jun. 12, 2018; Retrieved Feb. 7, 2020), 1-10 (Feb. 7, 2020) https://clinicaltrials.gov/ct2/show/NCT02738970.

US ClinicalTrails.gov., "A Study of Pertuzumab in Combination With Herceptin in Patients With HER2 Positive Breast Cancer (Neosphere)" (Pertuzumab and Herceptin; NCT00545688; First Posted; Oct. 17, 2007; Last Update Posted: Aug. 15, 2017; Printed: Jan. 21 , 2020),:1-13 https://clinicaltrials.gov/ct2/show/NCT00545688.

US ClinicalTrials.gov, "A Study of Pertuzumab in Combination With Herceptin and Chemotherapy in Participants With HER2-Positive Breast Cancer" (ClinicalTrials.gov Identifier: NCT00976989; History of Changes of Study; First Posted: Sep. 15, 2009; Results First Posted: Jun. 20, 2016; Last Updated Posted: Feb. 6, 2017; Retrieved: Aug. 27, 2020),:1-10 (Aug. 27, 2020) https://clinicaltrials.gov/ct2/show/study/NCT00976989.

US Department of Health and Human Services—FDA, CDER and CBER, "Guidance for Industry: FDA Approval of New Cancer Treatment Uses for Marketed Drug and Biological Products" Clin 7:1-13 (Dec. 1, 1998).

USPTO, "Public Patent Application Information Retrieval—PCT/US12/59683—Assignment Data Tab" (Last Page Update: Oct. 17, 2012; Retrieval Date: Feb. 11, 2020—Assignment Tab Information),:1-2 (Oct. 17, 2012) https://portal.uspto.gov/pair/PublicPair.

Valachis, A., et al., "Long-term follow-up of HER2-overexpressing stage II or III breast cancer treated by anthracycline-free neoadjuvant chemotherapy" Breast 20(6):485-490 (Dec. 1, 2011).

Valero, V., et al., "Future Direction of Neoadjuvant Therapy for Breast Cancer" Semin Oncol 25(2 Suppl 3):36-41 (Apr. 1, 1998).

Valero, V., et al., "Multicenter phase III randomized trial comparing docetaxel and trastuzumab with docetaxel, carboplatin, and trastuzumab as first-line chemotherapy for patients with HER2-gene-amplified metastatic breast cancer (BCIRG 007 study): two highly active therapeutic regimens" J Clin Oncol 29(2):149-156 (Jan. 10, 2011).

Van Warmerdam, L.J., et al., "The use of the Calvert formula to determine the optimal carboplatin dosage" J Cancer Res Clin Oncol 121(8):478-486 (Aug. 1, 1995).

Vaz-Luis et al., "Impact of hormone receptor status on patterns of recurrence and clinical outcomes among patients with human epidermal growth factor-2-positive breast cancer in the National Comprehensive Cancer Network: a prospective cohort study" Breast Cancer Research 14:R1 29:1-14 ( 2012).

Verma et al., "Is cardiotoxicity being adequately assessed in current trials of cytotoxic and targeted agents in breast cancer?" Ann Oncol 22:1011-1018 ( 2011).

Von Haehling et al., "Anaemia among patients with heart failure and preserved or reduced ejection fraction: results from the Seniors study" European Journal of Heart Failure 13:656-663 ( 2011).

Von Minckwitz et al., "Capecitabine vs. capecitabine + trastuzumab in patients with HER2-positive metastatic breast cancer progressing during trastuzumab treatment: The TBP phase III study (GBG 26/BIG 3-05)" Journal of Clinical Oncology 26( Suppl 158 (May 20 Supplement)):1025 ( 2008).

Von Minckwitz et al., "Correlation of various pathologic complete response (pCR) definitions with long-term outcome and the prognostic value of pCR in various breast cancer subtypes: Results from the German neoadjuvant meta-analysis." J Clin Oncol (Abstract 1028), 29( Suppl 9) ( 2011).

Von Minckwitz et al., "Supplementary Appendix—Adjuvant Pertuzumab and Trastuzumab in Early HER2-Positive Breast Cancer" N Engl J Med 377:1-46 ( 2017).

Von Minckwitz, G., et al., "Adjuvant Pertuzumab and Herceptin IN IniTial Therap Y of Breast Cancer: Aphinity (BIG 4-11/BO25126/TOC4939g)" Poster 34th Annual CTRC-AACR San Antonio Breast Cancer Symposium, San Antonio, Texas—USA, pp. 1 ( Dec. 6-10, 2011).

Von Minckwitz, G., et al., "Adjuvant Pertuzumab and Trastuzumab in Early HER2-Positive Breast Cancer" N Engl J Med 377(2):122-131 (Jul. 13, 2017).

Von Minck Witz, G., et al., "OT1-02-04: Adjuvant Pertuzumab and Herceptin IN IniTial Therap Y of Breast Cancer: Aphinity (Big 4-11/BO25126/TOC4939g)." Cancer Res (Abstracts: Thirty-Fourth Annual CTRC-AACR San Antonio Breast Cancer Symposium—Dec. 6-10, 2011; San Antonio, TX), 71(24):1 (Dec. 15, 2011).

Vose et al., "Phase II Study of Rituximab in Combination with CHOP Chemotherapy in Patients with Previously Untreated Intermediate- or High-Grade Non Hodgkin's Lymphoma (NHL)" Annals of Oncology (Abstract 195), 10( Suppl 3):58 ( 1999).

Wagner, A.D., et al., "Chemotherapy in advanced gastric cancer: A systematic review and meta-analysis based on aggregate data" J Clin Oncol 24(18):2903-2909 (Jun. 20, 2006).

Walshe, J., et al., "A Phase II Trial with Trastuzumab and Pertuzumab in Patients with HER2-Overexpressed Locally Advanced and Metastatic Breast Cancer" Clin Breast Cancer 6(6):535-539 (Feb. 1, 2006).

Wang, S., et al., "HER2 Kinase Domain Mutation Results in Constitutive Phosphorylation and Activation of HER2 and EGFR and Resistance to EGFR Tyrosine Kinase Inhibitors" Cancer Cell 10(1):25-38 (Jul. 1, 2006).

"Webster's Comprehensive Dictionary entries for concomitant and 'concurrent'":271 ( 1972).

Webster's Comprehensive Dictionary:271 ( 1992).

Witteles, et al., "Chemotherapy-Associated Cardiotoxicity: How Often Does it Really Occur and How Can it Be Prevented?" Heart Failure Clinics 7(3):333-344 ( 2011).

Wolff, A., et al., "American Society of Clinical Oncology/College of American Pathologists guideline recommendations for human epidermal growth factor receptor 2 testing in breast cancer" Arch Pathol Lab Med 131(1):18-43 (Jan. 1, 2007).

Wolmark, N., et al., "Preoperative Chemotherapy in Patients With Operable Breast Cancer: Nine-Year Results From National Surgical Adjuvant Breast and Bowel Project B-18" J Natl Cancer Inst Monogr 2001(30):96-102 (Dec. 1, 2001).

Wolmark, N., "Therapy with Abraxane and 5-Fluorouracil, Epirubicin, Cyclophosphamide (FEC) for Patients with Bresat Cancer, NCT00110695, clinical trials.gov" NSABP Foundation Inc.: 1-13 (Mar. 26, 2010).

Wong et al., "Gemcitabine and Platinum Pathway Pharmacogenetics in Asian Breast Cancer Patients" Cancer Genomics & Proteomics 8:255-260 ( 2011).

Wulfing, P., et al., "HER2-Positive Circulating Tumor Cells Indicate Poor Clinical Outcome in Stage I to III Breast Cancer Patients" Clin Cancer Res 12(6):1715-1720 (Mar. 15, 2006).

Wynne, C. et al., "Comparison of Subcutaneous and Intravenous Administration of Trastuzumab: A Phase I/Ib Trial in Healthy Male Volunteers and Patients with HER2-Positive Breast Cancer" J Clin Pharmacol 53(2):192-201 (Jan. 24, 2013).

Xu et al., "Hematologic toxicities associated with mTOR inhibitors temsirolimus and everolimus in cancer patients: a systematic review and meta-analysis" Curr Med Res Opin 30(1):67-74 ( 2014).

Yamamoto et al., "Similarity of protein encoded by the human c-erb-B-2 gene to epidermal growth factor receptor" Nature 319:230-234 (Jan. 16, 1986).

Yamashita, Y. et al., "Abstract 3477: Pertuzumab in combination with trastuzumab enhanced the anti-tumor activity in HER2-positive human gastric cancers" Cancer Res 70(8 Suppl 1):1-5 (Apr. 1, 2010).

Yamashita-Kashima, Y. et al., "Abstract 1761: Anti-tumor activity of trastuzumab-DM1 in combination with pertuzumab in a gastric cancer model" Cancer Res 71(8 Suppl 1):1-4 ( 2011).

Yamashita-Kashima, Y. et al., "Pertuzumab in combination with trastuzumab shows significantly enhanced antitumor activity in HER2-positive human gastric cancer xenograft models" Clin Cancer Res 17(15):5060-5070 (Aug. 1, 2011).

(56) References Cited

OTHER PUBLICATIONS

Yao, E. et al., "Suppression of HER2/HER3-mediated growth of breast cancer cells with combinations of GDC-0941 PI3K inhibitor, trastuzumab, and pertuzumab" Clin Cancer Res 15(12):4147-4156 (Jun. 15, 2009).

Yarden and Sliwkowski et al., "Untangling the ErbB signalling network" Nat Rev Mol Cell Biol. 2(2):127-37 (Feb. 2001).

Yardley et al., "Phase II Trial of Docetaxal Plus Imatinib Mesylate in the Treatment of Patients With Metastatic Breast Cancer" Clin Breast Cancer:237-242 ( 2009).

Yardley, et al., "A Phase II Trial of Oxaliplatin and Trastuzumab in the Treatment of HER2-Positive Metastatic Breast Cancer" Cancer Invest 28:865-871 ( 2010).

Yardley, "Visceral Disease in Patients With Metastatic Breast Cancer: Efficacy and Saftey of Treatment With Ixabepilone and Other Chemotherapeutic Agents" Clin Breast Cancer 10(1):64-73 ( 2010).

Yeboah et al., "Prognosis of Low Normal Left Ventricular Ejection Fraction in an Asymptomatic Population-based Adult Cohort. MESA" J Card Fail. 22(10):763-768 ( 2016).

Young et al., "Comparison of ECOG/WHO Performace Status and ASA Score as a Measure of Functional Status" Journal of Pain and Symptom Management 49(2):258-264 ( 2015).

Zia, M., et al., "Comparison of outcomes of phase II studies and subsequent randomized control studies using identical chemotherapeutic regimens" J Clin Oncol 23(28):6982-6991 (Oct. 1, 2005).

Carter, et al., "Relation of Tumor Size, Lymph Node Status, and Survival in 24,740 Breast Cancer Cases" Cancer (Prognostic Factors for Breast Cancer), 63:181-187 ( 1989).

Chia, S., "Neodjuvant and Adjuvant Therapy for HER2 Positive Disease" American Society of Clinical Oncology (ASCO) Educational Book:e41-e48 ( 2015).

ClinicalTrials.gov, "A Study Evaluating Pertuzumab (Perjeta) Combined with Trastuzumab (Herceptin) and Standard Anthracycline-based Chemotherapy in Participants with Human Epidermal Growth Factor Receptor 2 (HER2)-Positive Locally Advanced, Inflammatory, or Early-stage Breast Cancer (Berenice)" (NCT02132949; Protocol ID: WO29217; Version 4 (Submitted Jun. 23, 2014; Posted Jun. 24, 2014 [Estimated]; Last Update Posted to Study Record Sep. 17, 2021),:pp. 1-28.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 85 (Submitted Nov. 24, 2014; Posted Nov. 25, 2014 [Estimate]); Last Update Posted to Study Record Jun. 14, 2024; https://clinicaltrials.gov/study/NCT01358877?tab=history&a=85#version),:pp. 1-54.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 7 (Submitted Dec. 20, 2011; Posted Dec. 22, 2011 [Estimated]); Last Update Posted to Study Jun. 14, 2024; https://clinicaltrials.gov/study/NCT01358877?tab=history&a=7#version-c),:1-78.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 111 (Submitted Sep. 1, 2016; Posted Sep. 2, 2016 [Estimated]); Last Update Posted to Study Record Jun. 14, 2024; https://clinicaltrials.gov/study/NCT01358877?tab=history&a=111#version),:pp. 1-60.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 111 (Submitted Sep. 1, 2016; Posted Sep. 2, 2016 [Estimated]); Last Update Posted to Study Record Jun. 14, 2024; Webpage Printed: Jul. 20, 2024; https://clinicaltrials.gov/study/NCT01358877),:pp. 1-55.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 26 (Submitted Apr. 16, 2013; Posted Apr. 17, 2013 [Estimated]); https://clinicaltrials.gov/study/NCT01358877?tab=history&a=26#versioncontent-panel),:pp. 1-84.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 112 (Submitted Nov. 1, 2016, Posted Nov. 2, 2016 [Estimate]); Last Update Posted to Study Record Jun. 14, 2024; https://www.clinicaltrials.gov/study/NCT01358877?V_112=View#StudyPa),:pp. 1-60.

ClinicalTrials.gov, "A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (NCT01358877; Protocol ID: BO25126; Version 105 (Submitted Feb. 1, 2016; Posted Feb. 2, 2016 [Estimated]); Last Update Posted to Study Jun. 14, 2024; https://clinicaltrials.gov/study/NCT01358877?tab=history&a=105#version]),:1-54.

ClinicalTrials.gov, "History of Changes for Study NCT02738970: A Dose-Finding Study of Pertuzumab (Perjeta) in Combination with Trastuzumab (Herceptin) in Healthy Male Participants and Women with Early Breast Cancer (EBC)" https://clinicaltrials.gov/study/NCT02738970?intr=NCT02738970&rank=1&t (Version 4 (submitted Jul. 1, 2016, posted Jul. 4, 2016 [Estimated]) Last Update Posted to Study Jun. 12, 2018),: 1-20.

ClinicalTrials.gov, "History of Changes for Study: NCT00545688 a Study of Pertuzumab in Combination with Herceptin in Patients with HER2 Positive Breast Cancer" (Comparison of Version 4 (submitted Jan. 18, 2008) and Version 117 (submitted Dec. 16, 2015); Latest version of study submitted was Jul. 5, 2017 on webpage),:pp. 1-66.

ClinicalTrials.gov, "History of Changes for Study: NCT01358877; A Study of Pertuzumab in Addition to Chemotherapy and Trastuzumab as Adjuvant Therapy in Participants With Human Epidermal Growth Receptor 2 (HER2)-Positive Primary Breast Cancer" (Comparison of Version 105 (Submitted Feb. 1, 2016) and Version 111 (Submitted Sep. 1, 2016); Latest version of study submitted was Jul. 7, 2023 on webpage; Webpage printed Jul. 18, 2023),:pp. 1-44.

ClinicalTrials.gov, "History of Changes for Study: NCT01358877; A Study of Pertuzumab in Addition to Chemotherapy and Trastuzumab as Adjuvant Therapy in Participants With Human Epidermal Growth Receptor 2 (HER2)-Positive Primary Breast Cancer (Aphinity)" (Comparison of Version 105 (Submitted Feb. 1, 2016) and Version 111 (Submitted Sep. 1, 2016); Latest version of study submitted was Apr. 12, 2023 on webpage),:pp. 1-52.

ClinicalTrials.gov, "History of Changes for Study: NCT02132949; A Study Evaluating Pertuzumab (Perjeta) Combined with Trastuzumab (Herceptin) and Standard Anthracycline-based Chemotherapy in Participants with Human Epidermal Growth Factor Receptor 2 (HER2)-Positive Locally Advanced, Inflammatory, or Early-stage Breast Cancer" (Comparison of Version 4 (submitted Jun. 23, 2014) and Version 60 (submitted Mar. 1, 2017); Latest version of study submitted was Aug. 18, 2021 on webpage),:pp. 1-66.

Dang, C et al., "Berenice Final Analysis: Cardiac Safety Study of Neoadjuvant Pertuzumab, Trastuzumab, and Chemotherapy Followed by Adjuvant Pertuzumab and Trastuzumab in HER2-Positive Early Breast Cancer" Cancers 14(11):1-17 (May 24, 2022) https://doi.org/10.3390/cancers14112596.

Dang, C., "Neoadjuvant Therapy for HER2-Positive Breast Cancer: Ready for Prime Time?" https://www.medscape.org/viewarticle/844995_slide (slide presentation),:1-38 (Jun. 23, 2015).

Dang, C., "Neoadjuvant Therapy in HER2-Positive Breast Cancer: Ready for Prime Time?" https://web.archive.org/web/20150702080735/

(56) References Cited

OTHER PUBLICATIONS http://www.medscape.org:80/viewarticle/844995_transcript (Archived version of webpage containing 2 opening slides of Jun. 23, 2015 Dang slides),:1-4 (Jul. 2, 2015).
Dang, C., "Neoadjuvant Therapy in HER2-Positive Breast Cancer: Ready for Prime Time?" https://web.archive.org/web/20150701005101/http://www.medscape.org:80/viewarticle/844995 slide (Archived version of webpage where Jun. 23, 2015 Dang slides can be downloaded),:1-2 (Jul. 1, 2015).
"FDA Docket page for Mar. 22, 2013 Innovations in Breast Cancer Drug Development Neoadjuvant Breast Cancer Workshop transcript showing that the transcript was uploaded in Apr. 2014, visible by public for comment from Apr. 29, 2014, https://www.regulations.gov/document/FDA-2012-D-0432-0016":1-2.
Genentech, Inc et al., "Perjeta® (pertuzumab)—Annex I: Summary of Product Characteristics":1-44 (Jun. 28, 2018) https://www.ema.europa.eu/en/documents/product-information/perjeta-epar-product-information_en.pdf.
Genentech, Inc., "Annex I: Summary of Product Characteristics—Perjeta SMPC":1-22 (Mar. 4, 2013).
Genentech, Inc., "Annex I: Summary of Product Characteristics—Perjeta SMPC":1-45 (Dec. 8, 2017).
Genentech, Inc., "Annex I: Summary of Product Characteristics—Herceptin SMPC":1-133 ( 2015).
Gianni et al., "5-year analysis of neoadjuvant pertuzumab and trastuzumab in patients with locally advanced, inflammatory, or early-stage HER2-positive breast cancer (NeoSphere): a multicentre, open-label, phase 2 randomised trial" Lancet Oncol (ePub May 11, 2016, journal pub. date Jun. 2016), 17:791-800.
Gradishar et al., "Breast Cancer Version 3.2014 Clinical Practice Guidelines in Oncology" Journal of the National Comprehensive Cancer Network 12(4):542-590 (Apr. 2014).
Gradishar, et al., "Progress in systemic adjuvant therapy of early-stage breast cancer" Int J Clin Oncol 8:239-247 ( 2003).
Helwick, C., "Positive Results for Aphinity, but Value of Benefit of Dual HER2 Blockade Questioned" The ASCO Post (printed from website Jul. 21, 2024),:1-6 (Jun. 25, 2017).
"Innovations in Breast Cancer Drug Development Neoadjuvant Breast Cancer Workshop (Full Transcript) written record of proceedings of FDA public breast cancer workshop. Posted by the FDA Apr. 29, 2014, FDA-2012-D-0432-0016" US Food and Drug Adminstration /American Society for Clinical Oncology:1-379 (Mar. 22, 2013).
Olver, "Trastuzumab as the lead monoclonal antibody in advanced breast cancer: choosing which patient and when" Future Oncology 4(1):125-131 ( 2008).
O'Sullivan, et al., "Efficacy of Adjuvant Trastuzumab for Patients With Human Epidermal Growth Factor Receptor 2-Positive Early Breast Cancer and Tumors ≤2cm: A Meta-Analysis of the Randomized Trastuzumab Trials" Journal of Clinical Oncology (with 2 page Appendix), 33(24):2600-2608 (Aug. 20, 2015).
Perez, E. et al., "Four-Year Follow-Up of Trastuzumab Plus Adjuvant Chemotherapy for Operable Human Epidermal Growth Factor Receptor 2-Positive Breast Cancer: Joint Analysis of Dada From NCCTG N9831 and NSABP B-31" Journal of Clinical Oncology (with 1 page Appendix), 29(25):3366-3373 (Sep. 1, 2011).
Piccart-Gebhart, "Herceptin: the future in adjuvant breast cancer therapy" Anti-Cancer Drugs 12( Suppl 4):S27-S33 (2001).
Prat, A., "Pertuzumab Use in the Adjuvant Setting: Why Not?" Journal of Clinical Oncology (with correspondence page attached), 35(10):1138 (Apr. 1, 2017).
Press, et al., "HER2 Gene Amplification Testing by Fluorescent In Situ Hybridization (FISH): Comparison of the ASCO-College of American Pathologists Guidelines With FISH Scores Used for Enrollment in Breast Cancer International Research Group Clinical Trials" Journal of Clinical Oncology 34(29):3518-3528 (Oct. 10, 2016).
Richard, et al., "Pertuzumab and trastuzumab: the rationale way to synergy" Anais da Academia Brasileira de Ciencias (Annals of the Brazilian Academy of Sciences) 88( Suppl 1):565-577 ( 2016).
Shpilberg, O., et al., "Subcutaneous administration of rituximab (MabThera) and trastuzumab (Herceptin) using hyaluronidase" Br J Cancer 109(6):1556-1561 (Sep. 17, 2013).
Smyth, L. et al., "Weekly paclitaxel with trastuzumab and pertuzumab in patients with HER2-overexpressing metastatic breast cancer: overall survival and updated progression-free survival results from a phase II study" Breast Cancer Res Treat (author manuscript available in PMC Jul. 1, 2017. Published in final edited form as: Smyth et al., Breast Cancer Res Treat. 158(1):91-97 (Jul. 2016)),:1-16.
Swain, et al., "Cardiac Tolerability of Pertuzumab Plus Trastuzumab Plus Docetaxel in Patients with HER2-Positive Metastatic Breast Cancer in Cleopatra: A Randomized, Double-Blind, Placebo-Controlled Phase III Study" The Oncologist 18(3):257-264 ( 2013).
Von Minckwitz et al., (Supplementary Appendix and Protocol to Give Readers Additional Information Regarding von Minckwitz, et al., Adjuvant Pertuzumab and Trastuzumab in Early HER2-Positive Breast Cancer,N Engl J Med 377:122-131 (2017)),:1-384 ( 2017).
Von Minckwitz et al., "OT1-02-04: Adjuvant Pertuzumab and Herceptin IN IniTial Therap Y of Breast Cancer: Aphinity (BIG 4-11/BO25126/TOC4939g)" Cancer Research (Abstract OT1-02-04), 71(24 (suppl)):1-5 (Dec. 15, 2011) https://doi.org/10.1158/0008-5472.SABCS11-OT1-02-04.
Wu, Y., et al., "The Clinical Efficacy and CardiotoXicity of Fixed-Dose Monthly Trastuzumab in HER2-Positive Breast Cancer: A Single Institutional Analysis" PLoS One (pp. 1-12), 11(3):e0151112 (Mar. 8, 2016).
Carlson, R., "Long-Awaited ALTTO Results Prove Disappointing Two Anti-HER2 Therapies Not Better than One" Oncology Times 36(13):9-13 (Jul. 10, 2014).
Coates, et al., "Tailoring therapies—improving the management of early breast cancer: St Gallen International Expert Consensus on the Primary Therapy of Early Breast Cancer 2015, published online" Annals of Oncology 26(8): 1533-1546 (May 4, 2015).
Denduluri, et al., "Reply to L. Del Mastro and A. Prat" Journal of Clinical Oncology 35(10):1139-1140 (Apr. 1, 2017).
Amneal Pharmaceuticals, Inc., "Amneal Announces FDA Approval of Cyclophosphamide for Injection USP, Generic to Cytoxan®" Press Release: 1-5 (May 30, 2018).
Barrett et al., "Expert opinion on the use of anthracyclines in patients with advanced breast cancer at cardiac risk" Annals of Oncology 20:816-827 (Jan. 19, 2009).
"Carboplatin LiverTox" U.S. National Library of Medicine:1-5 (Sep. 15, 2020).
Chang et al., "Survival of Patients with Metastatic Breast Carcinoma, Importance of Prognostic Markers of the Primary Tumor" American Cancer Society. Presented in part at the 37th annual meeting of the American Society of Clinical Oncology, San Francisco, California, May 12-15, 2001.:545-553 ( 2003).
Chia et al., "Locally Advanced and Inflammatory Breast Cancer" Journal of Clinical Oncology 26(5):786-790 (Feb. 10, 2008).
"Fluorouracil Uses, Interactions, Mechanism of Action" DrugBank Online, updated May 28, 2024:1-31 (Jun. 13, 2005).
Garg, "Methodology for research I" Indian Journal of Anaesthesia 60(9):640-645 (Sep. 2016).
"Generic Docetaxel Approved" U.S. Pharmacist:1-2 (Apr. 20, 2011).
"Generic Ellence Availability" Drugs.com:103 (Apr. 10, 2024).
Guha, M., "PARP inhibitors stumble in breast cancer" Nature Biotechnology 29(5):373-374 (May 2011).
Helwig, "Iniparib Fails to Improve Outcomes in Triple-negative Breast Cancer" The Asco Post, retrieved from the internet https://ascopost.com/issues/july-1-2011/iniparib-fails-to-improve-outcomes-in-triple-negative-breast-cancer/:1-3 (Jul. 1, 2011).
Imkampe et al., "The significance of the site of recurrence to subsequent breast cancer survival" EJSO The Journal of Cancer Surgery 33:420-423 ( 2006).
Jacobsen, "Trastuzumab Biosimilars: What to Know About Ogivri and other Herceptin Alternatives" GoodRx Health:1-19 (Mar. 3, 2023).
Joerger et al., "Small HER2-positive, node-negative breast cancer: who should receive systemic adjuvant treatment?" Annals of Oncology 22(1):17-23 (Jan. 2011).

(56) References Cited

OTHER PUBLICATIONS

Li, A, "Accurate prediction of human drug toxicity: A major challenge in drug development" Chemico-Biological Interactions 150(1):3-7 (Dec. 2004).

Maughan et al., "Treatment of Breast Cancer" American Family Physician 81(11):1339-1346 (Jun. 1, 2010).

NIH—National Cancer Institute, "Inflammatory Breast Cancer":1 (Sep. 25, 2006) http://https://Web.archive.org/web/20060925081109/http://newscenter.cancer.gov/Templates/db_alpha.aspx?CdrID=45313.

Ross, "Declaration of Graham Ross re U.S. Appl. No. 18/309,452":1-3 (May 30, 2024).

Stanley, "Design of Randomized Controlled Trials" American Heart Association, Inc. 115:1164-1169 (2007).

Unicol, "Inflammatory Breast Cancer" Cancer Dictionary:1-3 ( 2004).

Voskoglou-Nomikos, T. et al., "Clinical Predictive Value of the in Vitro Cell Line, Human Xenograft, and Mouse Allograft Preclinical Cancer Models" Clin Cancer Res 9(11):4227-4239 (Sep. 15, 2003).

Xia et al., "The History and Development of HER2 Inhibitors" Pharmaceuticals 16:1-16 (Oct. 12, 2023).

Zhang et al., "Predicting Drug-Drug Interactions: An FDA Perspective" The AAPS Journal 11(2):300-306 (Jun. 2009).

\* cited by examiner

Variable Light

```
               10          20            30           40
2C4      DTVMTQSHKIMSTSVGDRVSITC  [KASQDVSIGVA]  WYQQRP
           **    ****  *              *                *
574      DIQMTQSPSSLSASVGDRVTITC  [KASQDVSIGVA]  WYQQKP
                                    *  **  ***
hum κI   DIQMTQSPSSLSASVGDRVTITC  [RASQSISNYLA]  WYQQKP 50          60          70          80
2C4      GQSPKLLIY  [SASYRYT]  GVPDRFTGSGSTDFTFTISSVQA
           **                    *   *          *    *  *
574      GKAPKLLIY  [SASYRYT]  GVPSRFSGSGSTDFTLTISSLQP
                    *  *****
hum κI   GKAPKLLIY  [AASSLES]  GVPSRFSGSGSTDFTLTISSLQP 90          100
2C4      EDLAVYYC  [QQYYIYPYT]  FGGGTKLEIK  (SEQ ID NO:5)
           *  *                  *    *
574      EDFATYYC  [QQYYIYPYT]  FGQGTKVEIK  (SEQ ID NO:7)
                    *** *
hum κI   EDFATYYC  [QQYNSLPWT]  FGQGTKVEIK  (SEQ ID NO:9)
```

*FIG. 2A*

Variable Heavy

```
                 10          20           30           40
2C4      EVQLQQSGPELVKPGTSVKISCKAS  [GFTFTQYTMQ]  WVKQS
            **   **  *   *  ***  *                    *  *
574      EVQLVESGGGLVQPGGSLRLSCAAS  [GFTFTDYTMD]  WVRQA
                                      **  *  *
hum III  EVQLVESGGGLVQPGGSLRLSCAAS  [GFTFSSYAMS]  WVRQA 50    a       60          70          80
2C4      HGKSLEWIG  [DVNPNSGGSIYNQRFKG]  KASLTVDRSSRIVYM
           *  *   **                       *** *     **** *
574      PGKGLEWVA  [DVNPNSGGSIYNQRFKG]  RFTLSVDRSKNTLYL
                     ****** *** ****       *  * *
hum III  PGKGLEWVA  [VISGDGGSTYYADSVKG]  RFTISRDNSKNTLYL abc       90       100ab          110
2C4      ELRSLTFEDTAVYYCAR  [NLGPSFYFDY]  WGQGTTLTVSS  (SEQ ID NO:6)
           ***  **                           **
574      QMNSLRAEDTAVYYCAR  [NLGPSFYFDY]  WGQGTLVTVSS  (SEQ ID NO:8)
                                ********
hum III  QMNSLRAEDTAVYYCAR  [GRVGYSLYDY]  WGQGTLVTVSS  (SEQ ID NO:10)
```

*FIG. 2B*

Amino Acid Sequence for Pertuzumab Light Chain

```
  1        10        20        30        40        50        60
  |         |         |         |         |         |         |
DIQMTQSPSSLSASVGDRVTITCKASQDVSIGVAWYQQKPGKAPKLLIYSASYRYTGVPS 70        80        90       100       110       120
          |         |         |         |         |         |
RFSGSGSGTDFTLTISSLQPEDFATYYCQQYYIYPYTFGQGTKVEIKRTVAAPSVFIFPP 130       140       150       160       170       180
          |         |         |         |         |         |
SDEQLKSGTASVVCLLNNFYPREAKVQWKVDNALQSGNSQESVTEQDSKDSTYSLSSTLT 190       200       210
          |         |         |
LSKADYEKHKVYACEVTHQGLSSPVTKSFNRGEC   (SEQ ID NO: 11)
```

FIG. 3A

Amino Acid Sequence for Pertuzumab Heavy Chain

```
  1        10        20        30        40        50        60
  |         |         |         |         |         |         |
EVQLVESGGGLVQPGGSLRLSCAASGFTFTDYTMDWVRQAPGKGLEWVADVNPNSGGSIY

70        80        90       100       110       120
          |         |         |         |         |         |
NQRFKGRFTLSVDRSKNTLYLQMNSLRAEDTAVYYCARNLGPSFYFDYWGQGTLVTVSSA 130       140       150       160       170       180
          |         |         |         |         |         |
STKGPSVFPLAPSSKSTSGGTAALGCLVKDYFPEPVTVSWNSGALTSGVHTFPAVLQSSG 190       200       210       220       230       240
          |         |         |         |         |         |
LYSLSSVVTVPSSSLGTQTYICNVNHKPSNTKVDKKVEPKSCDKTHTCPPCPAPELLGGP 250       260       270       280       290       300
          |         |         |         |         |        *|
SVFLFPPKPKDTLMISRTPEVTCVVVDVSHEDPEVKFNWYVDGVEVHNAKTKPREEQYNS 310       320       330       340       350       360
          |         |         |         |         |         |
TYRVVSVLTVLHQDWLNGKEYKCKVSNKALPAPIEKTISKAKGQPREPQVYTLPPSREEM 370       380       390       400       410       420
          |         |         |         |         |         |
TKNQVSLTCLVKGFYPSDIAVEWESNGQPENNYKTTPPVLDSDGSFFLYSKLTVDKSRWQ 430       440       448
          |         |         |
QGNVFSCSVMHEALHNHYTQKSLSLSPG   (SEQ ID NO: 12)
```

FIG. 3B

Trastuzumab Light Chain

```
1               15              30              45
DIQMTQSPSSLSASVGDRVTITCRASQDVNTAVAWYQQKPGKAPK 46              60              75              90
LLIYSASFLYSGVPSRFSGSRSGTDFTLTISSLQPEDFATYYCQQ 91              105             120             135
HYTTPPTFGQGTKVEIKRTVAAPSVFIFPPSDEQLKSGTASVVCL 136             150             165             180
LNNFYPREAKVQWKVDNALQSGNSQESVTEQDSKDSTYSLSSTLT 181             195             210     214
LSKADYEKHKVYACEVTHQGLSSPVTKSFNRGEC (SEQ ID NO: 13)
```

*FIG. 4A*

Trastuzumab Heavy Chain

```
1               15              30              45
EVQLVESGGGLVQPGGSLRLSCAASGFNIKDTYIHWVRQAPGKGL 46              60              75              90
EWVARIYPTNGYTRYADSVKGRFTISADTSKNTAYLQMNSLRAED 91              105             120             135
TAVYYCSRWGGDGFYAMDYWGQGTLVTVSSASTKGPSVFPLAPSS 136             150             165             180
KSTSGGTAALGCLVKDYFPEPVTVSWNSGALTSGVHTFPAVLQSS 181             195             210             225
GLYSLSSVVTVPSSSLGTQTYICNVNHKPSNTKVDKKVEPKSCDK 226             240             255             270
THTCPPCPAPELLGGPSVFLFPPKPKDTLMISRTPEVTCVVVDVS 271             285             300             315
HEDPEVKFNWYVDGVEVHNAKTKPREEQYNSTYRVVSVLTVLHQD 316             330             345             360
WLNGKEYKCKVSNKALPAPIEKTISKAKGQPREPQVYTLPPSREE 361             375             390             405
MTKNQVSLTCLVKGFYPSDIAVEWESNGQPENNYKTTPPVLDSDG 406             420             435     449
SFFLYSKLTVDKSRWQQGNVFSCSVMHEALHNHYTQKSLSLSPG
(SEQ ID NO: 14)
```

*FIG. 4B*

Pertuzumab Variant Light Chain

```
1               15              30              45
VHSDIQMTQSPSSLSASVGDRVTITCKASQDVSIGVAWYQQKPGK 46              60              75              90
APKLLIYSASYRTGVPSRFSGSGSGTDFTLTISSLQPEDFATYY 91              105             120             135
CQQYYIYPYTFGQGTKVEIKRTVAAPSVFIFPPSDEQLKSGTASV 136             150             165             180
VCLLNNFYPREAKVQWKVDNALQSGNSQESVTEQDSKDSTYSLSS 181             195             210     217
TLTLSKADYEKHKVYACEVTHQGLSSPVTKSFNRGEC (SEQ ID NO: 15)
```

*FIG. 5A*

Pertuzumab Variant Heavy Chain

```
1               15              30              45
EVQLVESGGGLVQPGGSLRLSCAASGFTFTDYTMDWVRQAPGKGL 46              60              75              90
EWVADVNPNSGGSIYNQRFKGRFTLSVDRSKNTLYLQMNSLRAED 91              105             120             135
TAVYYCARNLGPSFYFDYWGQGTLVTVSSASTKGPSVFPLAPSSK 136             150             165             180
STSGGTAALGCLVKDYFPEPVTVSWNSGALTSGVHTFPAVLQSSG 181             195             210             225
LYSLSSVVTVPSSSLGTQTYICNVNHKPSNTKVDKKVEPKSCDKT 226             240             255             270
HTCPPCPAPELLGGPSVFLFPPKPKDTLMISRTPEVTCVVVDVSH 271             285             300             315
EDPEVKFNWYVDGVEVHNAKTKPREEQYNSTYRVVSVLTVLHQDW 316             330             345             360
LNGKEYKCKVSNKALPAPIEKTISKAKGQPREPQVYTLPPSREEM 361             375             390             405
TKNQVSLTCLVKGFYPSDIAVEWESNGQPENNYKTTPPVLDSDGS 406             420             435             449
FFLYSKLTVDKSRWQQGNVFSCSVMHEALHNHYTQKSLSLSPGK
(SEQ ID NO: 16)
```

*FIG. 5B*

Efficacy IDFS (ITT)

|  | HR | P Value | 3 Yr IDFS | | |
| --- | --- | --- | --- | --- | --- |
|  |  |  | Ptz+Tras n=2400 | Pla+Tras n=2404 | Δ 3 Yr IDFS |
| Primary Endpoint IDFS | 0.81 (CI: 0.66, 1.00) | 0.0446* | 94.06% (CI: 93.01, 95.03) | 93.24% (CI: 92.21, 94.26) | 0.82% |
| Pts with Event |  |  | 171 Events | 210 Events |  |

*The p value shown in this table is based on stratification factor data taken from the eCRF. In a sensitivity analysis based on strat factor data from the IxRS system (FDA Analysis), the p-value from stratified log-rank rest was 0.0471.

*FIG. 7A*

Efficacy IDFS (Nodal Status)

|  | HR | P Value | 3 Yr IDFS | | |
|---|---|---|---|---|---|
|  |  |  | Ptz+Tras n=1503 | Pla+Tras n=1502 | Δ 3 Yr IDFS |
| Node Positive | 0.77 (CI: 0.62, 0.96) | 0.0188 | 91.99% (CI: 90.05, 93.29) | 90.15% (CI: 89.62, 91.69) | 1.84% |
| Pts with Event |  |  | 139 Events | 181 Events |  |

FIG. 8A

Efficacy IDFS (HR Status)

|  | HR | P Value | 3 Yr IDFS | | |
|---|---|---|---|---|---|
|  |  |  | Ptz+Tras n=864 | Pla+Tras n=858 | Δ 3 Yr IDFS |
| HR Negative | 0.76 (CI: 0.56, 1.04) | 0.0847 | 92.71% (CI: 91.01, 94.53) | 91.2% (CI: 89.24, 93.12) | 1.51% |
| Pts with Event |  |  | 71 Events | 91 Events |  |

*FIG. 9A*

ADJUVANT TREATMENT OF HER2-POSITIVE BREAST CANCER

CROSS REFERENCE TO RELATED APPLICATIONS

This application is a divisional of U.S. patent application Ser. No. 17/305,556, filed on Jul. 9, 2021, which is a divisional of U.S. patent application Ser. No. 15/907,718, filed on Feb. 28, 2018, now U.S. Pat. No. 11,077,189, issued Aug. 3, 2021, which claims the benefit of priority under 35 USC 119(e) of U.S. Provisional Patent Application Nos. 62/466,239, filed on Mar. 2, 2017, 62/469,317, filed on Mar. 9, 2017, and 62/486,876, filed on Apr. 18, 2017, the entire contents of which are incorporated herein by reference.

SEQUENCE LISTING

This application contains a Sequence Listing which has been submitted electronically in XML format and is hereby incorporated by reference in its entirety. Said XML copy, created on Apr. 8, 2024, is named P34141-US-6_Sequence_Listing.xml and is 32,768 bytes in size.

FIELD OF THE INVENTION

The present invention concerns the treatment of operable HER2-positive primary breast cancer in human patients by administration of pertuzumab in addition to chemotherapy and trastuzumab. In particular, the present invention concerns the treatment of operable HER2-positive early breast cancer (eBC) by adjuvant administration of pertuzumab, trastuzumab and chemotherapy.

It also concerns an article of manufacture comprising a vial with pertuzumab therein and a package insert providing instructions for adjuvant administration of pertuzumab in combination with trastuzumab and chemotherapy to treat HER2-positive early breast cancer and compositions for use in the methods herein.

BACKGROUND OF THE INVENTION

Members of the HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2). Members of the receptor family have been implicated in various types of human malignancy.

A recombinant humanized version of the murine anti-HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)).

Trastuzumab received marketing approval from the Food and Drug Administration Sep. 25, 1998 for the treatment of patients with metastatic breast cancer whose tumors overexpress the HER2 protein. At present, trastuzumab is approved for use as a single agent or in combination with chemotherapy or hormone therapy in the metastatic setting, and as single agent or in combination with chemotherapy as adjuvant treatment for patients with early-stage HER2-positive breast cancer. Trastuzumab-based therapy is now the recommended treatment for patients with HER2-positive early-stage breast cancer who do not have contraindications for its use (HERCEPTIN® prescribing information; NCCN Guidelines, version 2.2011). Trastuzumab plus docetaxel (or paclitaxel) is a registered standard of care in the first-line metastatic breast cancer (MBC) treatment setting (Slamon et al. N Engl J Med. 2001; 344(11):783-792; Marty et al. J Clin Oncol. 2005; 23(19):4265-4274).

Patients treated with the HER2 antibody trastuzumab are selected for therapy based on HER2 expression. See, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, U.S. Pat. Nos. 6,573,043, 6,905,830, and US2003/0152987, Cohen et al., concerning immunohistochemistry (IHC) and fluorescence in situ hybridization (FISH) for detecting HER2 overexpression and amplification. Thus, the optimal management of metastatic breast cancer now takes into account not only a patient's general condition, medical history, and receptor status, but also the HER2 status.

Pertuzumab (also known as recombinant humanized monoclonal antibody 2C4 (rhuMAb 2C4); Genentech, Inc, South San Francisco) represents the first in a new class of agents known as HER dimerization inhibitors (HDI) and functions to inhibit the ability of HER2 to form active heterodimers or homodimers with other HER receptors (such as EGFR/HER1, HER2, HER3 and HER4). See, for example, Harari and Yarden *Oncogene* 19:6102-14 (2000); Yarden and Sliwkowski. *Nat Rev Mol Cell Biol* 2:127-37 (2001); Sliwkowski *Nat Struct Biol* 10:158-9 (2003); Cho et al. *Nature* 421:756-60 (2003); and Malik et al. *Pro Am Soc Cancer Res* 44:176-7 (2003).

Pertuzumab blockade of the formation of HER2-HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)).

US 2006/0034842 describes methods for treating ErbB-expressing cancer with anti-ErbB2 antibody combinations. US 2008/0102069 describes the use of trastuzumab and pertuzumab in the treatment of HER2-positive metastatic cancer, such as breast cancer. Baselga et al., *J Clin Oncol*, 2007 *ASCO Annual Meeting* Proceedings Part I, Col. 25, No. 18S (June 20 Supplement), 2007:1004 report the treatment of patients with pre-treated HER2-positive breast cancer, which has progressed during treatment with trastuzumab, with a combination of trastuzumab and pertuzumab. Portera et al., *J Clin Oncol*, 2007 ASCO Annual Meeting Proceedings Part I. Vol. 25, No. 18S (June 20 Supplement), 2007: 1028 evaluated the efficacy and safety of trastuzumab+ pertuzumab combination therapy in HER2-positive breast cancer patients, who had progressive disease on trastuzumab-based therapy. The authors concluded that further evaluation of the efficacy of combination treatment was required to define the overall risk and benefit of this treatment regimen.

Pertuzumab has been evaluated in Phase II studies in combination with trastuzumab in patients with HER2-positive metastatic breast cancer who have previously received trastuzumab for metastatic disease. One study, conducted by the National cancer Institute (NCI), enrolled 11 patients with previously treated HER2-positive metastatic breast cancer. Two out of the 11 patients exhibited a partial response (PR) (Baselga et al., *J Clin Oncol* 2007 ASCO Annual Meeting Proceedings; 25:18S (June 20 Supplement): 1004).

The results of a Phase II neoadjuvant study evaluating the effect of a novel combination regimen of pertuzumab and trastuzumab plus chemotherapy (docetaxel) in women with early-stage HER2-positive breast cancer, presented at the CTRC-AACR San Antonio Breast Cancer Symposium (SABCS), Dec. 8-12, 2010, showed that the two HER2 antibodies plus docetaxel given in the neoadjuvant setting prior to surgery significantly improved the rate of complete tumor disappearance (pathological complete response rate, pCR, of 45.8 percent) in the breast by more than half compared to trastuzumab plus docetaxel (pCR of 29.0 percent), p=0.014.

The Clinical Evaluation of pertuzumab and trastuzumab (CLEOPATRA) Phase II clinical study assessed the efficacy and safety of pertuzumab plus trastuzumab plus docetaxel, as compared with placebo plus trastuzumab plus docetaxel, as first-line treatment for patients with locally recurrent, unresectable, or metastatic HER2-positive breast cancer. The combination of pertuzumab plus trastuzumab plus docetaxel, as compared with placebo plus trastuzumab plus docetaxel, when used as first-line treatment for HER2-positive metastatic breast cancer, significantly prolonged progression-free survival, with no increase in cardiac toxic effects. (Baselga et al., *N Eng J Med* 2012 366:2, 109-119).

The Phase II clinical study NeoSphere assessed the efficacy and safety of neoadjuvant administration of pertuzumab and trastuzumab in treatment-naïve women (patients who has not received any previous cancer therapy) with operable, locally advanced, and inflammatory breast cancer. Patients give pertuzumab and trastuzumab plus docetaxel showed a significantly improved pathological complete response rate compared with those given trastuzumab plus docetaxel, without substantial differences in tolerability (Gianni et al., *Lancet Oncol* 2012 13(1):25-32). Results of 5-year follow-up are reported by Gianni et al., *Lancet Oncol* 2016 17(6):791-800).

Adjuvant therapy, in the broadest sense, is treatment given in addition to the primary therapy to kill any cancer cells that may have spread, even if the spread cannot be detected by radiologic or laboratory tests.

Publications or seminars related to adjuvant therapy include: Paik et al., J. Natl. Cancer Inst., 92(24):1991-1998 (2000); Paik et al., J. Natl. Cancer Inst., 94:852-854 (2002); Paik et al. Successful quality assurance program for HER2 testing in the NSABP Trial for HERCEPTIN®. San Antonio Breast Cancer Symposium, 2002; Roche P C et al., J. Natl. Cancer Inst., 94(11):855-7 (2002); Albain et al., Proceedings of the American Society of Clinical Oncology Thirty-Eighth Annual Meeting, May 18-21 2002, Orlando, Fla., Abstract 143; The ATAC (Arimidex, Tamoxifen Alone or in Combination) Trialists' Group, Lancet, 359:2131-39 (2002); Geyer et al., 26th Annual San Antonio Breast Cancer Symposium (SABCS), December 2003, Abstract 12; Perez et al., Proc. ASCO, 2005, Abstract 556.

U.S. Patent Publication No. 2004/0014694 (published Jan. 22, 2004) describes a method of adjuvant therapy for the treatment of early breast cancer, comprising administration of docetaxel, doxorubicin and cyclophosphamide.

Adjuvant treatment of breast cancer by administration of HERCEPTIN® is disclosed in U.S. Pat. No. 8,591,897.

Patent Publications related to HER2 antibodies include: U.S. Pat. Nos. 5,677,171; 5,720,937; 5,720,954; 5,725,856; 5,770,195; 5,772,997; 6,165,464; 6,387,371; 6,399,063; 6,015,567; 6,333,169; 4,968,603; 5,821,337; 6,054,297; 6,407,213; 6,639,055; 6,719,971; 6,800,738; 5,648,237; 7,018,809; 6,267,958; 6,695,940; 6,821,515; 7,060,268; 7,682,609; 7,371,376; 6,127,526; 6,333,398; 6,797,814; 6,339,142; 6,417,335; 6,489,447; 7,074,404; 7,531,645; 7,846,441; 7,892,549; 6,573,043; 6,905,830; 7,129,840; 7,344,840; 7,468,252; 7,674,589; 6,949,245; 7,485,302; 7,498,030; 7,501,122; 7,537,931; 7,618,631; 7,862,817; 7,041,292; 6,627,196; 7,371,379; 6,632,979; 7,097,840; 7,575,748; 6,984,494; 7,279,287; 7,811,773; 7,993,834; 7,435,797; 7,850,966; 7,485,704; 7,807,799; 7,560,111; 7,879,325; 7,449,184; 7,700,299; 8,591,897; and US 2010/0016556; US 2005/0244929; US 2001/0014326; US 2003/0202972; US 2006/0099201; US 2010/0158899; US 2011/0236383; US 2011/0033460; US 2005/0063972; US 2006/018739; US 2009/0220492; US 2003/0147884; US 2004/0037823; US 2005/0002928; US 2007/0292419; US 2008/0187533; US 2003/0152987; US 2005/0100944; US 2006/0183150; US2008/0050748; US 2010/0120053; US 2005/0244417; US 2007/0026001; US 2008/0160026; US 2008/0241146; US 2005/0208043; US 2005/0238640; US 2006/0034842; US 2006/0073143; US 2006/0193854; US 2006/0198843; US 2011/0129464; US 2007/0184055; US 2007/0269429; US 2008/0050373; US 2006/0083739; US 2009/0087432; US 2006/0210561; US 2002/0035736; US 2002/0001587; US 2008/0226659; US 2002/0090662; US 2006/0046270; US 2008/0108096; US 007/0166753; US 2008/0112958; US 2009/0239236; US 2004/008204; US 2009/0187007; US 2004/0106161; US 2011/0117096; US 2004/048525; US 2004/0258685; US 2009/0148401; US 2011/0117097; US 2006/0034840; US 2011/0064737; US 2005/0276812; US 2008/0171040; US 2009/0202536; US 2006/0013819; US 2006/0018899; US 2009/0285837; US 2011/0117097; US 2006/0088523; US 2010/0015157; US 2006/0121044; US 2008/0317753; US2006/0165702; US 2009/0081223; US 2006/0188509; US 2009/0155259; US 2011/0165157; US 2006/0204505; US 2006/0212956; US 2006/0275305; US 2007/0009976; US 2007/0020261; US 2007/0037228; US 2010/0112603; US 2006/0067930; US 2007/0224203; US 2008/0038271; US 2008/0050385; 2010/0285010; US 2008/0102069; US 2010/0008975; US 2011/0027190; US 2010/0298156; US 2009/0098135; US 2009/0148435; US 2009/0202546; US 2009/0226455; US 2009/0317387; and US 2011/0044977.

SUMMARY OF THE INVENTION

New active treatments are required for patients with HER2-positive breast cancer, which is estimated to account for approximately 6000-8000 deaths per year in the United States, 12,000-15,000 deaths per year in Europe, and 60,000-90,000 deaths per year globally (based on mortality rates for breast cancer overall) (Levi et al., Eur J Cancer Prev 2005; 14:497-502; Estimates of worldwide burden of cancer in 2008: GLOBOCAN 2008. Int J Cancer 2010; 127:2893-

917; SEER cancer statistics review, 1975-2008 [Internet]. Bethesda, MD. National Cancer Institute; November 2010 [updated, 2011]; Malvezzi et al., Ann Oncol 2013; 24:792-800). The median age of patients presenting with HER2-positive breast cancer is in the mid-50s, approximately 5 years younger than the general breast cancer population (Breast Cancer Res Treat 2008; 110:153-9; Breast Cancer Res 2009; 11:R31). At a time when the actuarial survival for women is >80 years of age, the median loss of life years per patient is approximately two decades. Improving the results of initial therapy when the disease is still localized to the breast and regional lymph nodes offers the chance of potentially curing the disease, as well as delaying disease recurrence and death in those who are not cured.

The present invention is based, at least in part, on the analysis of the results of a randomized, double-blind, placebo-controlled two-arm Phase III clinical study (Adjuvant Pertuzumab and HERCEPTIN® IN Initial TherapY in Breast Cancer (APHINITY), NCT01358877/B025126) assessing the safety and efficacy of pertuzumab in addition to chemotherapy plus trastuzumab as adjuvant therapy in patients with operable HER2-positive primary cancer.

In a first aspect, the invention concerns a method of reducing the risk of recurrence of invasive breast cancer or death for a patient diagnosed with HER2-positive early breast cancer (eBC), comprising administering to the patient, following surgery, pertuzumab in combination with trastuzumab and chemotherapy, wherein the risk of recurrence of invasive breast cancer or death is reduced compared to administration of trastuzumab and chemotherapy, without pertuzumab.

In one embodiment, the patient remains alive without recurrence of invasive breast cancer for at least one year following said administration.

In a second aspect, the invention concerns a method of adjuvant therapy comprising administering to a human subject with HER2-positive early breast cancer (eBC), following surgery, pertuzumab in combination with trastuzumab and chemotherapy, wherein said therapy reduces the risk of recurrence of invasive breast cancer or death for said patient compared to administration of trastuzumab and chemotherapy, without pertuzumab, for at least one year following administration.

In both aspects, and in various embodiments, the patient may remain alive without recurrence of invasive breast cancer for at least 2 years, or for at least 3 years following administration.

In one embodiment, the patient is lymph node positive.

In a second embodiment, the patient is hormone receptor (HR) negative.

In a third embodiment, the risk of recurrence of invasive breast cancer or death is reduced by at least about 5%, or at least about 10%, or at least about 15%, or at least about 20%, or at least about 25% compared to administration of trastuzumab and chemotherapy, without pertuzumab, such as, for example, by at least 19% compared to administration of trastuzumab and chemotherapy, without pertuzumab.

In a fourth embodiment, the HER2 positive cancer is characterized by a HER2 expression level of IHC 2+ or 3+.

In a fifth embodiment, the cancer is HER2-amplified, where HER2 amplification may, for example, be determined by fluorescence in situ hybridization (FISH).

In a sixth embodiment, the cancer is HER2-mutated, where the HER2 mutation may, for example, be selected from the group consisting of insertions within exon 20 of HER2, deletions around amino acid residues 755-759 of HER2, G309A, G309E, S310F, D769H, D769Y, V777L, P780-Y781insGSP, V842I, R896C and other putative activating mutations found two or more unique specimens.

Pertuzumab and/or trastuzumab may be administered intravenously or subcutaneously.

In various embodiments, pertuzumab and trastuzumab are typically administered every three weeks.

According to one administration schedule, pertuzumab is administered as a 840 mg IV loading dose, followed by 420 mg, given by IV every 3 weeks.

According to one administration schedule, trastuzumab is administered as a 8 mg/kg intravenous (IV) loading dose, followed by 6 mg/kg, given by IV infusion every 3 weeks.

According to another administration schedule, pertuzumab is administered subcutaneously with a loading dose of 1200 mg followed by 600 mg every 3 weeks.

Pertuzumab and trastuzumab may be co-administered subcutaneously as two separate subcutaneous injections, or co-mixed as a single subcutaneous injection, or administered as a single co-formulation for subcutaneous administration.

In one embodiment, pertuzumab and trastuzumab are administered for at least 52 weeks.

In another embodiment, administration of pertuzumab and trastuzumab follows chemotherapy.

Chemotherapy may comprise anthracycline-based chemotherapy, or can be non-anthracycline-based chemotherapy.

In one embodiment, chemotherapy comprises administration of 5-fluorouracil+epirubicin or doxorubicin+cyclophosphamide, optionally further comprising administration of a taxane, e.g. docetaxel and/or paclitaxel.

In a second embodiment, chemotherapy comprises administration of doxorubicin or epirubicin+cyclophosphamide, optionally further comprising administration of a taxane, e.g. docetaxel and/or paclitaxel.

The non-anthracycline-based chemotherapy may, for example, comprise administration of docetaxel+carboplatin.

In another aspect, the invention concerns an article of manufacture comprising a vial with pertuzumab and a package insert wherein the package insert provides instructions to administer said pertuzumab as disclosed herein.

In yet another aspect, the invention concerns an article of manufacture comprising a vial or vials with pertuzumab and trastuzumab and a package insert wherein the package insert provides instructions to administer said pertuzumab and trastuzumab as disclosed herein.

In a further embodiment, the invention concerns a composition of pertuzumab for use, in combination with trastuzumab, for treatment of a patient with HER2-positive early breast cancer (eBC) as disclosed herein.

In a still further embodiment, the invention concerns the use of pertuzumab in the preparation of a medicament for the of a patient with HER2-positive early breast cancer (eBC), in combination with trastuzumab, as disclosed herein.

These and further aspects and embodiments will be apparent to those skilled in the art based on the disclosure and general knowledge in the pertinent art.

BRIEF DESCRIPTION OF THE DRAWINGS

FIG. 2A and FIG. 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 5 and 6, respectively); $V_L$ and $V_H$ domains of variant 574/pertuzumab (SEQ ID NOs. 7 and 8, respectively), and human $V_L$ and $V_H$ consensus frameworks (hum κ1, light kappa subgroup I; humIII, heavy subgroup III) (SEQ ID Nos. 9 and 10, respectively). Asterisks identify differences between variable domains of pertuzumab and murine monoclonal antibody 2C4 or between variable domains of pertuzumab and the human framework. Complementarity Determining Regions (CDRs) are in brackets.

FIG. 3A and FIG. 3B show the amino acid sequences of pertuzumab light chain (FIG. 3A; SEQ ID NO. 11) and heavy chain (FIG. 3B; SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIG. 4A and FIG. 4B show the amino acid sequences of trastuzumab light chain (FIG. 4A; SEQ ID NO. 13) and heavy chain (FIG. 4B; SEQ ID NO. 14), respectively. Boundaries of the variable light and variable heavy domains are indicated by arrows.

FIG. 5A and FIG. 5B depict a variant pertuzumab light chain sequence (FIG. 5A; SEQ ID NO. 15) and a variant pertuzumab heavy chain sequence (FIG. 5B; SEQ ID NO. 16), respectively.

FIG. 7A shows the efficacy results, using invasive Disease Free Survival (IDFS) as primary clinical endpoint, in patients treated with pertuzumab+trastuzumab (n=2400) and placebo+trastuzumab (n=2404), respectively, as described in Example 1.

FIG. 8A shows the efficacy results (IDFS) in node positive breast cancer patients treated with pertuzumab+trastuzumab (n=1503) and placebo+trastuzumab (n=1502), respectively, as described in Example 1.

FIG. 9A shows the efficacy results (IDFS) in central hormone receptor negative breast cancer patients treated with pertuzumab+trastuzumab (n=864) and placebo+trastuzumab (n=858), respectively, as described in Example 1.

DETAILED DESCRIPTION OF THE PREFERRED EMBODIMENTS

I. Definitions

Figure 1:
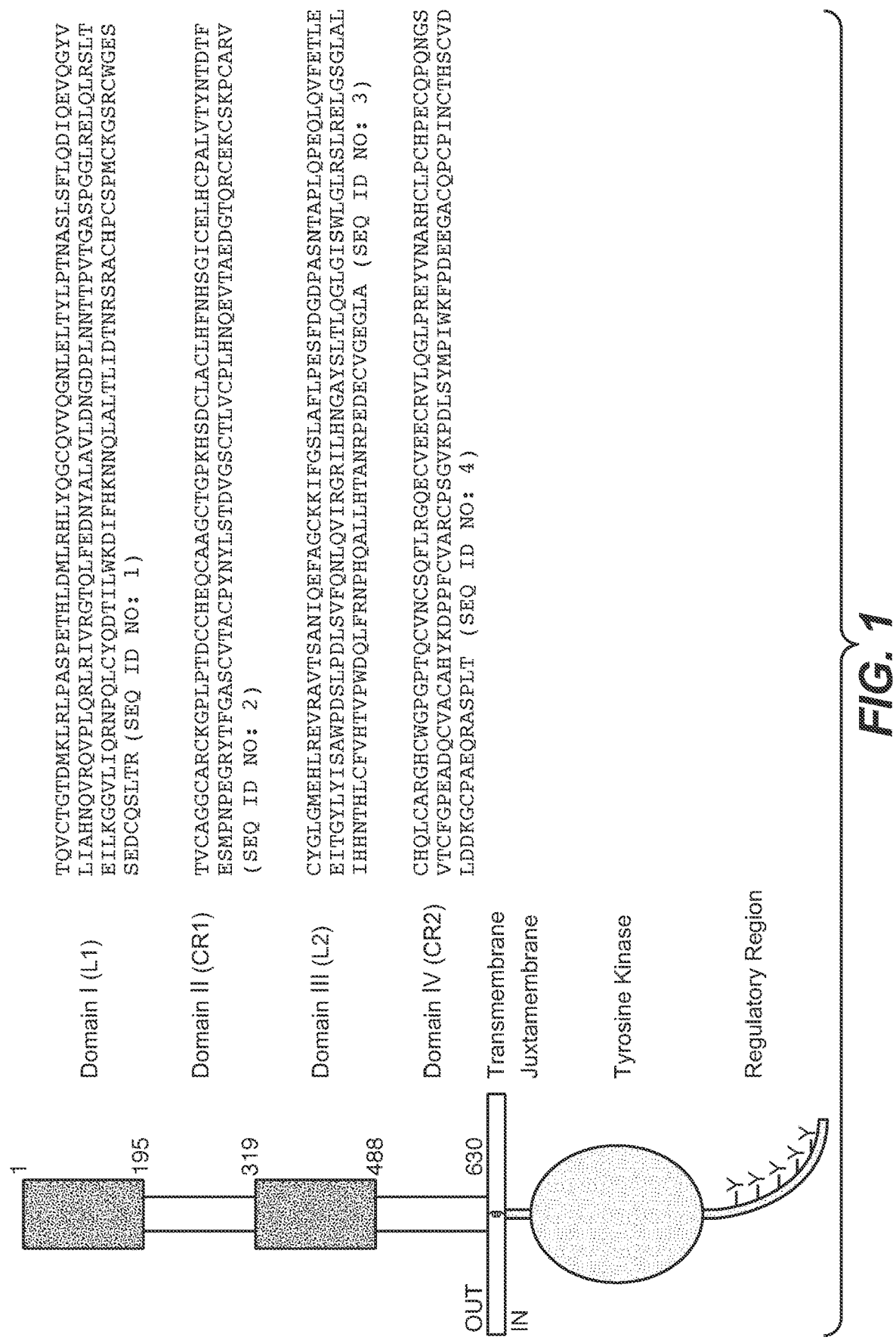
FIG. 1 provides a schematic of the HER2 protein structure, and amino acid sequences for Domains I-IV (SEQ ID Nos.1-4, respectively) of the extracellular domain thereof.

The term "chemotherapy" as used herein refers to treatment comprising the administration of a chemotherapy, as defined hereinbelow.

"Survival" refers to the patient remaining alive, and includes overall survival as well as progression free survival.

"Overall survival" or "OS" refers to the patient remaining alive for a defined period of time, such as 1 year, 5 years, etc. from the time of diagnosis or treatment. For the purposes of the clinical trial described in the example, overall survival (OS) is defined as the time from the date of randomization of patient population to the date of death from any cause.

"Progression free survival" or "PFS" refers to the patient remaining alive, without the cancer progressing or getting worse. For the purpose of the clinical trial described in the example, progression free survival (PFS) is defined as the time from randomization of study population to the first documented progressive disease, or unmanageable toxicity, or death from any cause, whichever occurs first. Disease progression can be documented by any clinically accepted methods, such as, for example, radiographical progressive disease, as determined by Response Evaluation Criteria in Solid Tumors (RECIST) (Therasse et al., *J Natl Ca Inst* 2000; 92(3):205-216), carcinomatous meningitis diagnosed by cytologic evaluation of cerebral spinal fluid, and/or medical photography to monitor chest wall recurrences of subcutaneous lesions.

"Disease free survival" or "DFS" refers to the patient remaining alive, without return of the cancer, for a defined period of time such as about 1 year, about 2 years, about 3 years, about 4 years, about 5 years, about 10 years, etc., from initiation of treatment or from initial diagnosis. In the studies underlying the present invention, DFS was analyzed according to the intent-to-treat principle, ie, patients were evaluated on the basis of their assigned therapy. The events used in the analysis of DFS typically include local, regional and distant recurrence of cancer, occurrence of secondary cancer, death from any cause in patients without a prior event (breast cancer recurrence or second primary cancer).

"Invasive Disease-Free Survival" of "IDFS", as defined herein is the time a patient lives without return of invasive breast cancer at any site or death from any cause after adjuvant treatment. In other words, IDFS is defined as the patient remaining alive (surviving) without return of invasive disease after adjuvant treatment for a defined period of time, such as about 1 year, about 2 years, about 3 years, about 4 years, about 5 years, about 10 years, etc., from initiation of treatment or from initial diagnosis. In one embodiment, IDFS is at about 1 year, or about 3 years, from initiation of treatment.

By "extending survival" is meant increasing overall or progression free survival in a patient treated in accordance with the present invention relative to an untreated patient and/or relative to a patient treated with one or more approved anti-tumor agents, but not receiving treatment in accordance with the present invention. In a particular example, "extending survival" means extending progression-free survival (PFS) and/or overall survival (OS) of cancer patients receiving the combination therapy of the present invention (e.g. treatment with a combination of pertuzumab, trastuzumab and a chemotherapy) relative to patients treated with trastuzumab and the chemotherapy only. In another particular example, "extending survival" means extending progression-free survival (PFS) and/or overall survival (OS) of cancer patients receiving the combination therapy of the present invention (e.g. treatment with a combination of pertuzumab, trastuzumab and a chemotherapy) relative to patients treated with pertuzumab and the chemotherapy only.

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The expressions "ErbB2" and "HER2" are used interchangeably herein and refer to human HER2 protein described, for example, in Semba et al., *PNAS* (USA) 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

Herein, "HER2 extracellular domain" or "HER2 ECD" refers to a domain of HER2 that is outside of a cell, either anchored to a cell membrane, or in circulation, including fragments thereof. The amino acid sequence of HER2 is shown in FIG. 1. In one embodiment, the extracellular domain of HER2 may comprise four domains: "Domain I" (amino acid residues from about 1-195; SEQ ID NO:1), "Domain II" (amino acid residues from about 196-319; SEQ ID NO:2), "Domain III" (amino acid residues from about 320-488: SEQ ID NO:3), and "Domain IV" (amino acid residues from about 489-630; SEQ ID NO:4) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 1 herein.

"HER3" or "ErbB3" herein refer to the receptor as disclosed, for example, in U.S. Pat. Nos. 5,183,884 and 5,480,968 as well as Kraus et al. *PNAS* (USA) 86:9193-9197 (1989).

A "low HER3" cancer is one which expresses HER3 at a level less than the median level for HER3 expression in the cancer type. In one embodiment, the low HER3 cancer is epithelial ovarian, peritoneal, or fallopian tube cancer. HER3 DNA, protein, and/or mRNA level in the cancer can be evaluated to determine whether the cancer is a low HER3 cancer. See, for example, U.S. Pat. No. 7,981,418 for additional information about low HER3 cancer. Optionally, a HER3 mRNA expression assay is performed in order to determine that the cancer is a low HER3 cancer. In one embodiment, HER3 mRNA level in the cancer is evaluated, e.g. using polymerase chain reaction (PCR), such as quantitative reverse transcription PCR (qRT-PCR). Optionally, the cancer expresses HER3 at a concentration ratio equal or lower than about 2.81 as assessed qRT-PCR, e.g. using a COBAS z480® instrument.

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.*, 269(20): 14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER antibody" is an antibody that binds to a HER receptor. Optionally, the HER antibody further interferes with HER activation or function. Preferably, the HER antibody binds to the HER2 receptor. HER2 antibodies of interest herein are pertuzumab and trastuzumab.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer. Preferably, such an antibody binds to HER2 at the heterodimeric binding site thereof. The most preferred dimerization inhibiting antibody herein is pertuzumab or MAb 2C4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors;

and antibodies which bind to HER4 and inhibit dimerization thereof with one or more other HER receptors.

A "HER2 dimerization inhibitor" is an agent that inhibits formation of a dimer or heterodimer comprising HER2.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2 (SEQ ID NO: 15). Franklin et al. *Cancer Cell* 5:317-328 (2004).

A HER2 antibody that "binds to a heterodimeric binding site" of HER2, binds to residues in Domain II (SEQ ID NO: 2) and optionally also binds to residues in other of the domains of the HER2 extracellular domain, such as domains I and III, SEQ ID NOs: 1 and 3), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II (SEQ ID NO: 2) and optionally residues in other domain(s) of HER2, such as domains I and III (SEQ ID NOs: 1 and 3, respectively). Preferably the antibody that binds to domain II binds to the junction between domains I, II and III of HER2.

For the purposes herein, "pertuzumab" and "rhuMAb 2C4", which are used interchangeably, refer to an antibody comprising the variable light and variable heavy amino acid sequences in SEQ ID NOs: 7 and 8, respectively. Where pertuzumab is an intact antibody, it preferably comprises an IgG1 antibody; in one embodiment comprising the light chain amino acid sequence in SEQ ID NO: 11 or 15, and heavy chain amino acid sequence in SEQ ID NO: 12 or 16. The antibody is optionally produced by recombinant Chinese Hamster Ovary (CHO) cells. The terms "pertuzumab" and "rhuMAb 2C4" herein cover biosimilar versions of the drug with the United States Adopted Name (USAN) or International Nonproprietary Name (INN): pertuzumab.

For the purposes herein, "trastuzumab" and "rhuMAb4D5", which are used interchangeably, refer to an antibody comprising the variable light and variable heavy amino acid sequences from within SEQ ID Nos: 13 and 14, respectively. Where trastuzumab is an intact antibody, it preferably comprises an IgG1 antibody; in one embodiment comprising the light chain amino acid sequence of SEQ ID NO: 13 and the heavy chain amino acid sequence of SEQ ID NO: 14. The antibody is optionally produced by Chinese Hamster Ovary (CHO) cells. The terms "trastuzumab" and "rhuMAb4D5" herein cover biosimilar versions of the drug with the United States Adopted Name (USAN) or International Nonproprietary Name (INN): trastuzumab.

The term "antibody" herein is used in the broadest sense and specifically covers monoclonal antibodies, polyclonal antibodies, multispecific antibodies (e.g. bispecific antibodies), and antibody fragments, so long as they exhibit the desired biological activity.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). Humanized HER2 antibodies specifically include trastuzumab (HERCEPTIN®) as described in Table 3 of U.S. Pat. No. 5,821,337 expressly incorporated herein by reference and as defined herein; and humanized 2C4 antibodies such as pertuzumab as described and defined herein.

An "intact antibody" herein is one which comprises two antigen binding regions, and an Fc region. Preferably, the intact antibody has a functional Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, MD. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest,* 5th Ed. Public Health Service, National Institutes of Health, Bethesda, MD (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into Asubclasses® (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

A "naked antibody" is an antibody that is not conjugated to a heterologous molecule, such as a cytotoxic moiety or radiolabel.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "deamidated" antibody is one in which one or more asparagine residues thereof has been derivitized, e.g. to an aspartic acid, a succinimide, or an iso-aspartic acid.

The terms "cancer" and "cancerous" refer to or describe the physiological condition in mammals that is typically characterized by unregulated cell growth.

"Early-stage breast cancer" or "early breast cancer" or "eBC", as used herein, refers to breast cancer that has not spread beyond the breast or the axillary lymph nodes. Such cancer is generally treated with neoadjuvant or adjuvant therapy.

An "advanced" cancer is one which has spread outside the site or organ of origin, either by local invasion or metastasis. Accordingly, the term "advanced" cancer includes both locally advanced and metastatic disease, such as "advanced breast cancer".

A "refractory" cancer is one which progresses even though an anti-tumor agent, such as a chemotherapy, is being administered to the cancer patient. An example of a refractory cancer is one which is platinum refractory.

A "recurrent" cancer is one which has regrown, either at the initial site or at a distant site, after a response to initial therapy, such as surgery.

A "locally recurrent" cancer is cancer that returns after treatment in the same place as a previously treated cancer.

A "non-resectable" or "unresectable" cancer is not able to be removed (resected) by surgery.

"Adjuvant therapy" or "adjuvant treatment" or "adjuvant administration" refers to systemic therapy given after surgery. Adjuvant treatment may be given after definitive surgery, where no evidence of residual disease can be detected, so as to reduce the risk of disease recurrence. The goal of adjuvant therapy is to prevent recurrence of the cancer, and therefore to reduce the chance of cancer-related death.

"Definitive surgery" refers to complete removal of tumor and surrounding tissue as well as any involved lymph nodes. Such surgery includes lumpectomy, mastectomy, such as total mastectomy plus axillary dissection, double mastectomy etc.

"Node-positive" or "lymph node positive" breast cancer is breast cancer that has spread to the regional lymph nodes (usually those under the arm). Subjects with node-positive breast cancer herein included those with 1-3 involved nodes; 4-9 involved nodes; and 10 or more involved nodes. Subjects with 4 or more involved nodes are at higher risk of recurrence than those with less or no involved nodes.

"Estrogen receptor (ER) positive" cancer is cancer which tests positive for expression of ER. Conversely, "ER negative" cancer tests negative for such expression. Analysis of ER status can be performed by any method known in the art. For the purpose of the studies herein, ER-positive tumors are defined as ≥10 fmol/mg cytosol protein by the Dextran-coated charcoal or sucrose-density gradient method, or positive (using individual laboratory criteria) by the enzyme immunoassay (EIA) method, or by immunocytochemical assay.

"Cancer recurrence" herein refers to a return of cancer following treatment, and includes return of cancer in the breast, as well as distant recurrence, where the cancer returns outside of the breast.

A subject at "high risk of cancer recurrence" is one who has a greater chance of experiencing recurrence of cancer, for example, relatively young subjects (e.g., less than about 50 years old), those with positive lymph nodes, particularly 4 or more involved lymph nodes (including 4-9 involved lymph nodes, and 10 or more involved lymph nodes), those with tumors greater than 2 cm in diameter, those with HER2-positive breast cancer, and those with hormone receptor negative breast cancer (i.e., estrogen receptor (ER) negative and progesterone receptor (PR) negative). A subject's risk level can be determined by a skilled physician. Generally, such high risk subjects will have lymph node involvement (for example with 4 or more involved lymph nodes); however, subjects without lymph node involvement are also high risk, for example if their tumor is greater or equal to 2 cm.

"Progesterone receptor (PR) positive" cancer is cancer which tests positive for expression of PR. Conversely, "PR negative" cancer tests negative for such expression. Analysis of PR status can be performed by any method known in the art. For the purpose of the studies herein, acceptable methods include the Dextran-coated charcoal or sucrose-density gradient methods, enzyme immunoassay (EIA) techniques, and immunocytochemical assays.

"Neoadjuvant therapy" or "neoadjuvant treatment" or "neoadjuvant administration" refers to systemic therapy given prior to surgery.

Herein, "initiation of treatment" refers to the start of a treatment regimen following surgical removal of the tumor. In one embodiment, such may refer to administration of AC following surgery. Alternatively, this can refer to an initial administration of the HER2.antibody and/or chemotherapeutic agent.

By an "initial administration" of a HER2 antibody and chemotherapeutic agent is meant a first dose of the HER2 antibody or chemotherapeutic agent as part of a treatment schedule.

By "curing" cancer herein is meant the absence of cancer recurrence at about 4 or about 5 years after beginning adjuvant therapy.

"Metastatic" cancer refers to cancer which has spread from one part of the body (e.g. the breast) to another part of the body.

Herein, a "patient" or "subject" is a human patient. The patient may be a "cancer patient," i.e. one who is suffering or at risk for suffering from one or more symptoms of cancer, in particular breast cancer.

A "patient population" refers to a group of cancer patients. Such populations can be used to demonstrate statistically significant efficacy and/or safety of a drug, such as pertuzumab and/or trastuzumab.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer or biological sample which "displays HER activation" is one which, in a diagnostic test, demonstrates activation or phosphorylation of a HER receptor. Such activation can be determined directly (e.g. by measuring HER phosphorylation by ELISA) or indirectly (e.g. by gene expression profiling or by detecting HER heterodimers, as described herein).

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via in situ hybridization (ISH), including fluorescent in situ hybridization (FISH; see WO98/45479 published October, 1998) and chromogenic in situ hybridization (CISH; see, e.g. Tanner et al., *Am. J. Pathol.* 157(5): 1467-1472 (2000); Bella et al., *J. Clin. Oncol.* 26: (May 20 suppl; abstr 22147) (2008)), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

A "HER2-positive" cancer comprises cancer cells which have higher than normal levels of HER2, such as HER2-positive breast cancer. Optionally, HER2-positive cancer has an immunohistochemistry (IHC) score of 2+ or 3+ and/or an in situ hybridization (ISH) amplification ratio ≥2.0.

Herein, an "anti-tumor agent" refers to a drug used to treat cancer. Non-limiting examples of anti-tumor agents herein include chemotherapy agents, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

The "epitope 2C4" is the region in the extracellular domain of HER2 to which the antibody 2C4 binds. In order to screen for antibodies which bind essentially to the 2C4 epitope, a routine cross-blocking assay such as that described in *Antibodies. A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds essentially to the 2C4 epitope of HER2. Epitope 2C4 comprises residues from Domain II (SEQ ID NO: 2) in the extracellular domain of HER2. 2C4 and pertuzumab binds to the extracellular domain of HER2 at the junction of domains I, II and III (SEQ ID NOs: 1, 2, and 3, respectively). Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2 (SEQ ID NO: 4). To screen for antibodies which bind essentially to the 4D5 epitope, a routine cross-blocking assay such as that described in Antibodies. *A Laboratory Manual*, Cold Spring Harbor Laboratory, Ed Harlow and David Lane (1988), can be performed. Alternatively, epitope mapping can be performed to assess whether the antibody binds essentially to the 4D5 epitope of HER2 (e.g. any one or more residues in the region from about residue 529 to about residue 625, inclusive of the HER2 ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapy" is use of a chemical compound useful in the treatment of cancer. Examples of chemotherapeutic agents, used in chemotherapy, include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e. g., calicheamicin, especially calicheamicin gammaII and calicheamicin omegaII (see, e.g., Agnew, *Chem Intl. Ed. Engl.,* 33: 183-186 (1994)) and anthracyclines such as annamycin, AD 32, alcarubicin, daunorubicin, doxorubicin, dexrazoxane, DX-52-1, epirubicin, GPX-100, idarubicin, valrubicin, KRN5500, menogaril, dynemicin, including dynemicin A, an esperamicin, neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX™, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; piranibicin; losoxantrone; 2-ethylhydrazide; procarbazine; PSK7 polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine;

mitobronitol; mitolactol; pipobroman; gacytosine; arabinoside ("Ara-C"); cyclophosphamide; thiotepa; taxanes; chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "taxane" is a chemotherapy which inhibits mitosis and interferes with microtubules. Examples of taxanes include Paclitaxel (TAXOL®; Bristol-Myers Squibb Oncology, Princeton, N.J.); cremophor-free, albumin-engineered nanoparticle formulation of paclitaxel or nab-paclitaxel (ABRAXANE™; American Pharmaceutical Partners, Schaumberg, Illinois); and Docetaxel (TAXOTERE®; Rhône-Poulenc Rorer, Antony, France).

An "anthacycline" is a type of antibiotic that comes from the fungus *Streptococcus peucetius*, examples include: Daunorubicin, Doxorubicin, Epirubicin, and any other anthracycline chemotherapeutic agents, including those listed before.

"Anthracycline-based chemotherapy" refers to a chemotherapy regimen that consists of or includes one or more anthracycline. Examples include, without limitation, 5-FU, epirubicin, and cyclophosphamide (FEC); 5-FU, doxorubicin, and cyclophosphamide (FAC); doxorubicin and cyclophosphamide (AC); epirubicin and cyclophosphamide (EC); dose-dense doxorubicin and cyclophosphamide (ddAC), and the like.

For the purposes herein, "carboplatin-based chemotherapy" refers to a chemotherapy regimen that consists of or includes one or more Carboplatins. An example is TCH (Docetaxel/TAXOL®, Carboplatin, and trastuzumab/HERCEPTIN®).

An "aromatase inhibitor" inhibits the enzyme aromatase, which regulates estrogen production in the adrenal glands. Examples of aromatase inhibitors include: 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In one embodiment, the aromatase inhibitor herein is letrozole or anastrozole.

An "antimetabolite chemotherapy" is use of an agent which is structurally similar to a metabolite, but cannot be used by the body in a productive manner. Many antimetabolite chemotherapy interferes with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARA®), cladrabine, 2-deoxy-D-glucose etc.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

The term "platin" is used herein to refer to platinum based chemotherapy, including, without limitation, cisplatin, carboplatin, and oxaliplatin.

The term "fluoropyrimidine" is used herein to refer to an antimetabolite chemotherapy, including, without limitation, capecitabine, floxuridine, and fluorouracil (5-FU).

In the context of the present invention, "chemotherapy" is used to refer to any chemotherapy used for the treatment of invasive breast cancer, including standard of care anthracycline-based chemotherapy and non-anthracycline-based chemotherapy. In one embodiment, chemotherapy comprises administration of 5-fluorouracil+epirubicin or doxorubicin+cyclophosphamide, optionally further comprising administration of a taxane, e.g. docetaxel and/or paclitaxel. In another embodiment, chemotherapy comprises administration of doxorubicin or epirubicin+cyclophosphamide, optionally further comprising administration of a taxane, e.g. docetaxel and/or paclitaxel. The non-anthracycline-based chemotherapy may, for example, comprise administration of docetaxel+carboplatin.

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Intravenous" administration refers to administering a drug (e.g. trastuzumab and/or pertuzumab and/or chemotherapy) into a vein of a patient, e.g. by infusion (slow therapeutic introduction into the vein).

"Subcutaneous" administration refers to administering a drug (e.g. trastuzumab and/or pertuzumab and/or chemotherapy) beneath the skin of the patient.

"Infusion" or "infusing" refers to the introduction of a drug-containing solution into the body through a vein for therapeutic purposes. Generally, this is achieved via an intravenous (IV) bag.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinyl chloride.

By "co-administering" is meant intravenously administering two (or more) drugs during the same administration, rather than sequential infusions of the two or more drugs. Generally, this will involve combining the two (or more) drugs into the same IV bag prior to co-administration thereof.

"Cardiac toxicity" refers to any toxic side effect resulting from administration of a drug or drug combination. Cardiac toxicity can be evaluated based on any one or more of: incidence of symptomatic left ventricular systolic dysfunction (LVSD) or congestive heart failure (CHF), or decrease in left ventricular ejection fraction (LVEF).

The phrase "without increasing cardiac toxicity" for a drug combination including pertuzumab refers to an incidence of cardiac toxicity that is equal or less than that observed in patients treated with drugs other than pertuzumab in the drug combination (e.g. equal or less than that resulting from administration of trastuzumab and the chemotherapy, e.g. Docetaxel).

A "vial" is a container suitable for holding a liquid or lyophilized preparation. In one embodiment, the vial is a single-use vial, e.g. a 20-cc single-use vial with a stopper.

A "package insert" is a leaflet that, by order of the Food and Drug Administration (FDA) or other Regulatory Authority, must be placed inside the package of every prescription drug. The leaflet generally includes the trademark for the drug, its generic name, and its mechanism of action; states its indications, contraindications, warnings, precautions, adverse effects, and dosage forms; and includes instructions for the recommended dose, time, and route of administration.

The expression "safety data" concerns the data obtained in a controlled clinical trial showing the prevalence and severity of adverse events to guide the user regarding the safety of the drug, including guidance on how to monitor and prevent adverse reactions to the drug. Table 3 and Table 4 herein provide safety data for pertuzumab. The safety data comprises any one or more (e.g. two, three, four or more) of the most common adverse events (AEs) or adverse reactions (ADRs) in Tables 3 and 4. For example, the safety data comprises information about neutropenia, febrile neutropenia, diarrhea and/or cardiac toxicity as disclosed herein.

"Efficacy data" refers to the data obtained in controlled clinical trial showing that a drug effectively treats a disease, such as cancer.

By "stable mixture" when referring to a mixture of two or more drugs, such as pertuzumab and trastuzumab," means that each of the drugs in the mixture essentially retains its physical and chemical stability in the mixture as evaluated by one or more analytical assays. Exemplary analytical assays for this purpose include: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay. In one embodiment, mixture has been shown to be stable for up to 24 hours at 5° C. or 30° C.

A drug that is administered "concurrently" with one or more other drugs is administered during the same treatment cycle, on the same day of treatment as the one or more other drugs, and, optionally, at the same time as the one or more other drugs. For instance, for cancer therapies given every 3-weeks, the concurrently administered drugs are each administered on day-1 of a 3-week cycle.

II. Antibody and Chemotherapy Compositions

The HER2 antigen to be used for production of antibodies may be, e.g., a soluble form of the extracellular domain of a HER2 receptor or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. *PNAS (USA)* 88:8691-8695 (1991)) can be used to generate antibodies. Other forms of HER2 receptor useful for generating antibodies will be apparent to those skilled in the art.

Various methods for making monoclonal antibodies herein are available in the art. For example, the monoclonal antibodies may be made using the hybridoma method first described by Kohler et al., *Nature*. 256:495 (1975), by recombinant DNA methods (U.S. Pat. No. 4,816,567).

The anti-HER2 antibodies used in accordance with the present invention, trastuzumab and pertuzumab, are commercially available.

(i) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.,* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

U.S. Pat. No. 6,949,245 describes production of exemplary humanized HER2 antibodies which bind HER2 and block ligand activation of a HER receptor.

Humanized HER2 antibodies specifically include trastuzumab as described in Table 3 of U.S. Pat. No. 5,821,337 expressly incorporated herein by reference and as defined herein; and humanized 2C4 antibodies such as pertuzumab as described and defined herein.

The humanized antibodies herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, *Bethesda, MD* (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX (SEQ ID NO: 17), where X is preferably D or S; DVNPNSGGSIYNQRFKG (SEQ ID NO:18); and/or NLGPSFYFDY (SEQ ID NO:19), optionally comprising amino acid modifications of those CDR residues, e.g. where the modifications essentially maintain or improve affinity of the antibody. For example, an antibody variant for use in the methods of the present invention may have from about one to about seven or about five amino acid substitutions in the above variable heavy CDR sequences. Such antibody variants may be prepared by affinity maturation, e.g., as described below.

The humanized antibody may comprise variable light domain complementarity determining residues KASQDVSIGVA (SEQ ID NO:20); SASYX$^1$X$^2$X$^3$, where X$^1$ is preferably R or L, X$^2$ is preferably Y or E, and X$^3$ is preferably T or S (SEQ ID NO:21); and/or QQYYIYPYT (SEQ ID NO:22), e.g. in addition to those variable light domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below.

The present application also contemplates affinity matured antibodies which bind HER2. The parent antibody may be a human antibody or a humanized antibody, e.g., one comprising the variable light and/or variable heavy sequences of SEQ ID Nos. 7 and 8, respectively (i.e. comprising the VL and/or VH of pertuzumab). An affinity matured variant of pertuzumab preferably binds to HER2 receptor with an affinity superior to that of murine 2C4 or pertuzumab (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Humanization of murine 4D5 antibody to generate humanized variants thereof, including trastuzumab, is described in U.S. Pat. Nos. 5,821,337, 6,054,297, 6,407,213, 6,639,055, 6,719,971, and 6,800,738, as well as Carter et al. PNAS (USA), 89:4285-4289 (1992). HuMAb4D5-8 (trastuzumab) bound HER2 antigen 3-fold more tightly than the mouse 4D5 antibody, and had secondary immune function (ADCC) which allowed for directed cytotoxic activity of the humanized antibody in the presence of human effector cells. HuMAb4D5-8 comprised variable light ($V_L$) CDR residues incorporated in a $V_L$ κ subgroup I consensus framework, and variable heavy ($V_H$) CDR residues incorporated into a $V_H$ subgroup III consensus framework. The antibody further comprised framework region (FR) substitutions as positions: 71, 73, 78, and 93 of the $V_H$ (Kabat numbering of FR residues; and a FR substitution at position 66 of the $V_L$ (Kabat numbering of FR residues). trastuzumab comprises non-A allotype human γ 1 Fc region.

Various forms of the humanized antibody or affinity matured antibody are contemplated. For example, the humanized antibody or affinity matured antibody may be an antibody fragment. Alternatively, the humanized antibody or affinity matured antibody may be an intact antibody, such as an intact IgG1 antibody.

(ii) Pertuzumab Compositions

In one embodiment of a HER2 antibody composition, the composition comprises a mixture of a main species pertuzumab antibody and one or more variants thereof. The preferred embodiment herein of a pertuzumab main species antibody is one comprising the variable light and variable heavy amino acid sequences in SEQ ID Nos. 5 and 6, and most preferably comprising a light chain amino acid sequence of SEQ ID No. 11, and a heavy chain amino acid sequence of SEQ ID No. 12 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab=)2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialidated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

For more information regarding exemplary pertuzumab compositions, see U.S. Pat. Nos. 7,560,111 and 7,879,325 as well as US 2009/0202546A1.

(iii) Trastuzumab Compositions

The trastuzumab composition generally comprises a mixture of a main species antibody (comprising light and heavy chain sequences of SEQ ID NOS: 13 and 14, respectively), and variant forms thereof, in particular acidic variants (including deamidated variants). Preferably, the amount of such acidic variants in the composition is less than about 25%, or less than about 20%, or less than about 15%. See, U.S. Pat. No. 6,339,142. See, also, Harris et al., *J. Chromatography. B* 752:233-245 (2001) concerning forms of trastuzumab resolvable by cation-exchange chromatography, including Peak A (Asn30 deamidated to Asp in both light chains); Peak B (Asn55 deamidated to isoAsp in one heavy chain); Peak 1 (Asn30 deamidated to Asp in one light chain); Peak 2 (Asn30 deamidated to Asp in one light chain, and Asp102 isomerized to isoAsp in one heavy chain); Peak 3 (main peak form, or main species antibody); Peak 4 (Asp102 isomerized to isoAsp in one heavy chain); and Peak C (Asp102 succinimide (Asu) in one heavy chain). Such variant forms and compositions are included in the invention herein.

(iv) Chemotherapy

Standard chemotherapy for the treatment of HER2-positive early breast cancer (eBC) includes, without limitation, anthracycline-containing and non-anthracycline containing chemotherapies, such as treatment with one or more of doxorubicin, epirubicin, 5-fluorouracil+epirubicin, doxorubicin+cyclophosphamide, and taxanes (e.g. docetaxel or paclitaxel). Standard chemotherapy, as used in the methods of the present invention, specifically includes 1) 3-4 cycles (q3w) of 5-fluorouracil+epirubicin or doxorubicin+cyclophosphamide followed by either 4 cycles (q3w) of docetaxel or 12 weekly cycles of paclitaxel. 2) 4 cycles (q3w) of doxorubicin or epirubicin+cyclophosphamide followed by either 4 cycles (q3w) of docetaxel or 12 weekly cycles of paclitaxel, and 3) (non-anthracycline chemotherapy therapy) 6 cycles (q3w) of docetaxel+carboplatin, as described in Example 1. The drugs used in the various standard chemotherapy regimens are commercially available and administered in accordance with local prescribing information and as described in Example 1.

III. Selecting Patients for Therapy

Detection of HER2 can be used to select patients for treatment in accordance with the present invention. Several FDA-approved commercial assays are available to identify HER2-positive cancer patients. These methods include HERCEPTES® (Dako) and PATHWAY® HER2 (immunohistochemistry (IHC) assays) and PathVysion® and HER2 FISH pharmDx™ (FISH assays). Users should refer to the package inserts of specific assay kits for information on the validation and performance of each assay.

For example, HER2 overexpression may be analyzed by IHC, e.g. using the HERCEPTEST® (Dako). Paraffin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as HER2-negative, whereas those tumors with 2+ or 3+ scores may be characterized as HER2-positive.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA*. 84:7159-7163 (1987)), occurs in approximately 30% of breast cancers, and in these patients, relapse-ftee survival and overall survival are diminished (Slamon et al., *Science*. 244:707-712 (1989); Slamon et al., *Science*. 235:177-182 (1987)).

The presence of HER2 protein overexpression and gene amplification are highly correlated, therefore, alternatively, or additionally, the use of in situ hybridization (ISH), e.g. fluorescent in situ hybridization (FISH), assays to detect gene amplification may also be employed for selection of patients appropriate for treatment in accordance with the present invention. FISH assays such as the INFORM™ (sold by Ventana, Arizona) or PathVysion® (Vysis, Illinois) may be carried out on formalin-fixed, paraffin-embedded tumor tissue to determine the extent (if any) of HER2 amplification in the tumor.

Most commonly, HER2-positive status is confirmed using archival paraffin-embedded tumor tissue, using any of the foregoing methods.

Preferably, HER2-positive patients having a 2+ or 3+ IHC score or who are FISH or ISH positive are selected for treatment in accordance with the present invention.

See also U.S. Pat. No. 7,981,418 for alternative assays for screening patients for therapy with pertuzumab, and the Examples.

IV. Pharmaceutical Formulations

Therapeutic formulations of the HER2 antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), generally in the form of lyophilized formulations or aqueous solutions. Antibody crystals are also contemplated (see US Pat Appln 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801, expressly incorporated herein by reference.

Lyophilized antibody formulations are described in U.S. Pat. Nos. 6,267,958, 6,685,940 and 6,821,515, expressly incorporated herein by reference.

In one embodiment, the trastuzumab formulation is a sterile, white to pale yellow preservative-free lyophilized powder for intravenous (IV) administration, comprising 440 mg trastuzumab, 400 mg .alpha.,α-trehalose dihydrate, 9.9 mg L-histidine-HCl, 6.4 mg L-histidine, and 1.8 mg polysorbate 20, USP. Reconstitution of 20 mL of bacteriostatic water for injection (BWFI), containing 1.1% benzyl alcohol as a preservative, yields a multi-dose solution containing 21 mg/mL trastuzumab, at pH of approximately 6.0. For further details, see the trastuzumab prescribing information.

In another embodiment, a trastuzumab formulation e.g. suitable for subcutaneous administration, is disclosed in U.S. Pat. No. 9,345,661. This formulation comprises
   (a) about 100 to about 150 mg/ml trastuzumab;
   (b) about 1 to about 50 mM of a buffering agent providing a pH of 5.5.+−0.2.0;
   (c) about 150 to about 250 mM of α,α-trehalose dihydrate or sucrose as a first stabilizer and about 5 to about 15 mM methionine as a second stabilizer;
   (d) about 0.01 to about 0.08% of a nonionic surfactant; and
   (e) about 1'000 to 16'000 U/ml of at least one hyaluronidase enzyme.

In one embodiment, the pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

In another embodiment, the pertuzumab formulation for therapeutic use is suitable for subcutaneous administration and comprises 600 mg pertuzumab at a concentration of 60 mg/ml, 600 mg trastuzumab at a concentration of 60 mg/ml, 1,000 U/mL rHuPH20, 20 mM His-HCl pH 5.5, 105 mM trehalose, 100 mM sucrose, 0.04% polysorbate 20, 10 mM methionine, and sterile water for injection up to a total volume of 10 ml, which may be contained in a 15-ml vial.

In a further embodiment, the pertuzumab formulation for therapeutic use is suitable for subcutaneous administration and comprises 1,200 mg pertuzumab at a concentration of 80 mg/ml, 600 mg trastuzumab at a concentration of 40 mg/ml, 1,000 U/mL rHuPH20, 20 mM His-HCl pH 5.5, 70 mM trehalose, 133 mM sucrose, 0.04% polysorbate 20, 10 mM methionine, and sterile water for injection up to a total volume of 15 ml, which may be contained in a 20-ml vial.

In a still further embodiment, a co-formulation of pertuzumab and trastuzumab, e.g. suitable for subcutaneous administration comprises a single fixed dose of about 600 mg of pertuzumab and a single fixed dose of about 600 mg of trastuzumab, or a single fixed dose of about 1200 mg of pertuzumab and a single fixed dose of about 600 mg of trastuzumab, and a hyaluronidase enzyme, such as recombinant human hyaluronidase (rHuPH20), in an amount sufficient to result in an increase in the dispersion of the pertuzumab and trastuzumab contained in the same liquid formulation during subcutaneous administration, such as at a concentration of at least about 600 U/mL, or at a concentration of between about 600 U/ml and about 2,000 U/ml, e.g. at a concentration of about 1,000 U/mL.

In further embodiments, a co-formulation of pertuzumab and trastuzumab, e.g. suitable for subcutaneous administration, comprises: 600 mg pertuzumab at a concentration of 60 mg/ml, 600 mg trastuzumab at a concentration of 60 mg/ml, 1,000 U/mL rHuPH20, 20 mM His-HCl pH 5.5, 105 mM trehalose, 100 mM sucrose, 0.04% polysorbate 20, 10 mM methionine, and sterile water for injection up to a total volume of 10 ml, or 1,200 mg pertuzumab at a concentration of 80 mg/ml, 600 mg trastuzumab at a concentration of 40 mg/ml, 1,000 U/mL rHuPH20, 20 mM His-HCl pH 5.5, 70 mM trehalose, 133 mM sucrose, 0.04% polysorbate 20, 10 mM methionine, and sterile water for injection up to a total volume of 15 ml.

The formulation of the placebo used in the clinical trials described in the Examples is equivalent to pertuzumab, without the active agent.

The formulation herein may also contain more than one active compound as necessary for the particular indication being treated, preferably those with complementary activities that do not adversely affect each other. Various drugs which can be combined with the HER dimerization inhibitor are described in the Method Section below. Such molecules are suitably present in combination in amounts that are effective for the purpose intended.

The formulations to be used for in vivo administration must be sterile. This is readily accomplished by filtration through sterile filtration membranes.

V. Treatment Methods

The invention concerns a method for the treatment of HER2-positive early breast cancer comprising adjuvant administration to a patient with HER2-positive early breast cancer of an effective amount of a combination pertuzumab, trastuzumab, and standard chemotherapy, wherein such administration increases reaches a primary and/or secondary efficacy endpoint, such as increase in Disease-Free Survival (DFS), in particular invasive Disease-Free Survival (IDFS) relative to administration of trastuzumab with standard chemotherapy, without administration of pertuzumab.

In one embodiment, the patient treated in accordance with the present invention has been diagnosed with HER2-positive, node-positive early breast cancer.

In another embodiment, the patient treated in accordance with the present invention has been diagnosed with HER2-positive, hormone-receptor negative breast cancer.

In one embodiment, pertuzumab, trastuzumab and chemotherapy are administered following one of the following schedules: pertuzumab IV and trastuzumab IV q3w in combination with chemotherapy according to one of the following schedules (as per attending physician's discretion): 1) 3-4 cycles (q3w) or 5-fluorouracil+epirubicin or doxorubicin+cyclophosphamide followed by either 4 cycles (q3w) (q3w) of docetaxel or 12 weekly cycles of paclitaxel; 2) 4 cycles (q3w) of doxorubicin or epirubicin+cyclophosphamide followed by either 4 cycles (q3w) or docetaxel or 12 weekly cycles of paclitaxel; 3) (non-anthracycline therapy) 6 cycles (q3w) of docetaxel+carboplatin.

In one embodiment trastuzumab and/or pertuzumab are administered intravenously. In other embodiment, trastuzumab and/or pertuzumab are administered subcutaneously (e.g. via a co-formulation including both trastuzumab and pertuzumab which is suitable for subcutaneous administration).

In one embodiment pertuzumab iv is administered with a loading dose of 840 mg followed by 420 mg every 3 weeks.

In one embodiment trastuzumab iv is administered with a loading dose of 8 mg/mg followed by 6 mg/kg every 3 weeks.

In one embodiment pertuzumab sc is administered with a loading dose of 1200 mg followed by 600 mg every 3 weeks.

In one embodiment trastuzumab sc is administered with a loading dose of 600 mg followed by 600 mg every 3 weeks.

Additional dosages and schedules for chemotherapy used to treat HER2-positive early breast cancer are disclosed in the examples below, but other dosages and schedules are known and contemplated according to the invention herein.

VI. Articles of Manufacture

In another embodiment of the invention, an article of manufacture containing materials useful for the treatment of breast cancer is provided. The article of manufacture comprises a vial with a fixed dose of the HER2 (pertuzumab), wherein the fixed dose is approximately 420 mg, approximately 525 mg, approximately 600 mg, approximately 840 mg, or approximately 1050 mg, or approximately 1200 mg of the HER antibody.

The article of manufacture preferably further comprises a package insert. The package insert may provide instructions to administer the fixed dose to a breast cancer patient, intravenously or subcutaneously.

In one embodiment, the article of manufacture comprises two vials, wherein a first vial contains a fixed dose of approximately 840 mg of pertuzumab, and a second vial contains a fixed dose of approximately 420 mg of pertuzumab.

In another embodiment, the article of manufacture of comprises two vials, wherein a first vial contains a fixed dose of approximately 1200 mg of pertuzumab, and a second vial contains a fixed dose of approximately 600 mg of pertuzumab.

In one embodiment of an article of manufacture herein comprises an intravenous (IV) bag containing a stable mixture of pertuzumab and trastuzumab suitable for administration to a cancer patient. Optionally, the mixture is in saline solution; for example comprising about 0.9% NaCl or about 0.45% NaCl. An exemplary IV bag is a polyolefin or polyvinyl chloride infusion bag, e.g. a 250 mL IV bag. According to one embodiment of the invention, the mixture includes about 420 mg or about 840 mg of pertuzumab and from about 200 mg to about 1000 mg of trastuzumab (e.g. from about 400 mg to about 900 mg of trastuzumab).

Optionally, the mixture in the IV bag is stable for up to 24 hours at 5° C. or 30° C. Stability of the mixture can be evaluated by one or more assays selected from the group consisting of: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay.

VII. Deposit of Biological Materials

The following hybridoma cell lines have been deposited with the American Type Culture Collection, 10801 University Boulevard, Manassas, VA 20110-2209, USA (ATCC):

| Antibody Designation | ATCC No. | Deposit Date |
| --- | --- | --- |
| 4D5 | ATCC CRL 10463 | May 24, 1990 |
| 2C4 | ATCC HB-12697 | Apr. 8, 1999 |

TABLE 1

TABLE OF SEQUENCES

| description | SEQ ID NO | FIG. |
| --- | --- | --- |
| HER2 domain I | 1 | 1 |
| HER2 domain II | 2 | 1 |
| HER2 domain III | 3 | 1 |
| HER2 domain IV | 4 | 1 |
| 2C4 variable light | 5 | 2A |
| 2C4 variable heavy | 6 | 2B |
| 574/pertuzumab variable light | 7 | 2A |
| 574/pertuzumab variable heavy | 8 | 2B |
| human $V_L$ consensus framework | 9 | 2A |
| Human $V_H$ consensus framework | 10 | 2B |
| pertuzumab light chain | 11 | 3A |

TABLE 1-continued

TABLE OF SEQUENCES

| description | SEQ ID NO | FIG. |
|---|---|---|
| pertuzumab heavy chain | 12 | 3B |
| trastuzumab light chain | 13 | 4A |
| trastuzumab heavy chain | 14 | 4B |
| Variant pertuzumab light chain | 15 | 5A |
| Variant pertuzumab heavy chain | 16 | 5B |
| GFTFTDYTMX | 17 | |
| DVNPNSGGSIYNQRFKG | 18 | |
| NLGPSFYFDY | 19 | |
| KASQDVSIGVA | 20 | |
| SASYX$^1$X$^2$X$^3$ | 21 | |
| QQYYIYPYT | 22 | |

Further details of the invention are illustrated by the following non-limiting Example. The disclosures of all citations in the specification are expressly incorporated herein by reference.

A list of abbreviations and definition of terms, as used throughout the specification, including the Examples, is provided in the following Table 2.

| Abbreviation | Definition |
|---|---|
| AC | doxorubicin (Adriamycin□) plus cyclophosphamide |
| ADCC | antibody-dependent cell-mediated cytotoxicity |
| AE | adverse event |
| ARDS | acute respiratory distress syndrome |
| ATA | anti-therapeutic antibody |
| BCS | breast-conserving surgery |
| bpCR | breast pathologic complete response |
| BSA | body surface area |
| CALGB | Cancer and Leukemia Group B |
| CBE | clinical breast examination |
| CHF | congestive heart failure |
| CISH | chromogenic in situ hybridization |
| CR | complete response |
| CSR | Clinical Study Report |
| CT | computed tomography |
| CTCAE | Common Terminology Criteria for Adverse Events |
| D | Docetaxel |
| DCarbH | docetaxel, carboplatin, and trastuzumab (HERCEPTIN ®) (also known as TCH) |
| DCIS | ductal carcinoma in situ |
| dd | dose-dense |
| ddAC | dose-dense doxorubicin (ADRIAMYCIN ®) plus cyclophosphamide |
| DFS | disease-free survival |
| EBC or eBC | early breast cancer |
| EBCTCG | Early Breast Cancer Trialists' Collaborative Group |
| ECG | electrocardiogram |
| ECHO | echocardiogram |
| ECOG | Eastern Cooperative Oncology Group |
| eCRF | electronic Case Report Form |
| EDC | electronic data capture |
| EFS | event-free survival |
| EGFR | epidermal growth factor receptor |
| ER | estrogen receptor |
| ESMO | European Society for Medical Oncology |
| FFPE | formalin-fixed paraffin-embedded |
| FISH | fluorescent in situ hybridization |
| GCG | German Breast Group |
| G-CSF | granulocyte colony-stimulating factor |
| H | HERCEPTIN ® |
| HER2 | human epidermal growth factor receptor 2 |
| HR | hazard ratio |
| IB | Investigator's Brochure |
| IBC | inflammatory breast cancer |
| ICH | International Conference on Harmonisation |
| IDFS | invasive disease-free survival |
| IMP | investigational medicinal product |
| IND | investigational new drug |
| ISH | in situ hybridization |
| ITT | intent-to-treat |
| IV | Intravenous |
| IUD | intrauterine device |
| IxRS | interactive voice/web response system |
| LABC | locally advanced breast cancer |
| LCIS | lobular carcinoma in situ |
| LPLV | last patient, last visit |
| LVEF | left ventricular ejection fraction |
| LVSD | left ventricular systolic dysfunction |
| MAPK | mitogen-activated protein kinase |
| MBC | metastatic breast cancer |
| MRI | magnetic resonance imaging |
| mRNA | messenger RNA |
| MUGA | multiple-gated acquisition scan |
| NCCN | National Comprehensive Cancer Network |
| NCCTG | North Central Cancer Treatment Group |
| NCI | National Cancer Institute |
| NSABP | National Surgical Adjuvant Breast and Bowel Project |
| NYHA | New York Heart Association |
| OS | overall survival |
| P | Paclitaxel |
| pCR | pathological complete response |
| PET | positron emission tomography |
| PFS | progression-free survival |
| PgR | progesterone receptor |
| PH | PERJETA ® and HERCEPTIN ® |
| PI3K | phosphoinositol 3-kinase |
| Pla | Placebo |
| PR | partial response |
| PVC | polyvinyl chloride |
| RCB | Residual Cancer Burden |
| RCR | Roche Clinical Repository |
| RECIST | Response Evaluation Criteria in Solid Tumors |
| RT | Radiotherapy |
| SD | stable disease |
| SISH | silver in situ hybridization |
| SLN | sentinel lymph node |
| SLNB | sentinel lymph node biopsy |
| SWFI | sterile water for injection |
| T | paclitaxel (TAXOL ®) |
| TCH | docetaxel (TAXOTERER ®), cyclophosphamide, and trastuzumab (HERCEPTIN ®) (abbreviated to DCarbH in this document) |
| TH | paclitaxel plus HERCEPTIN ® |
| tpCR | total pathologic complete response |
| ULN | upper limit of normal |

Example 1

A Phase III Study of Pertuzumab in Addition to Chemotherapy and Trastuzumab as Adjuvant Therapy in Participants with HER2-Positive Primary Breast Cancer.

Purpose

This randomized, double-blind, placebo-controlled, two-arm Phase III study (Adjuvant Pertuzumab and Trastuzumab In Initial Therapy of Breast Cancer, APHINITY, NCT01358877) currently enrolling 4806 patients, to assess the safety and efficacy of pertuzumab in addition to chemotherapy plus trastuzumab as adjuvant therapy in participants with operable HER2-positive primary breast cancer. This study is carried out in collaboration with the Breast International Group (BIG).

Study Design

Figure 6A:
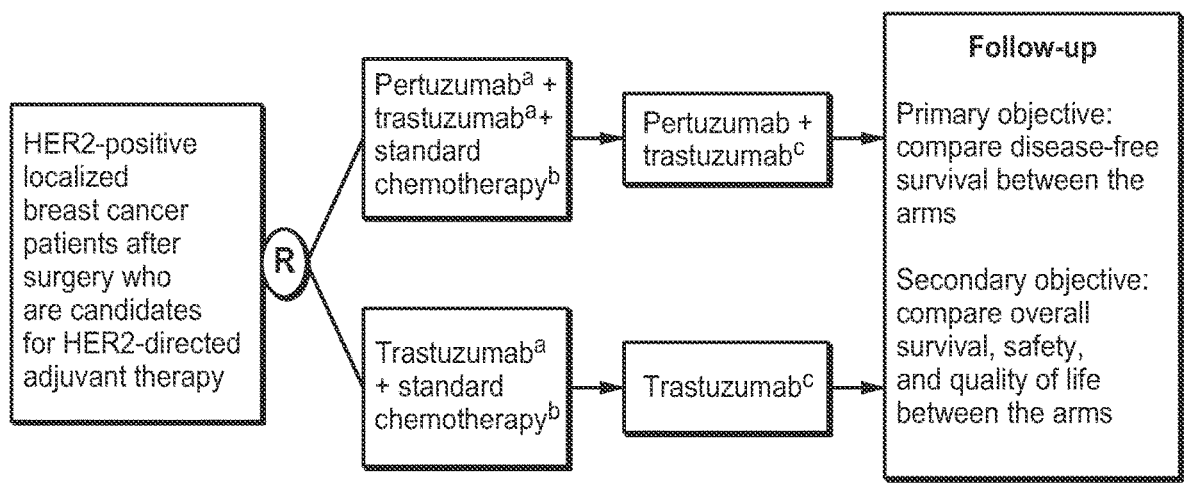
FIG. 6A is the schema of the APHINITY clinical trial evaluating efficacy of adjuvant pertuzumab based therapy in operable HER2-positive early breast cancer (eBC) as described in Example 1. Notes: [a]trastuzumab 6 mg/kg IV q3 weeks, pertuzumab 420 mg IV q3 weeks; [b]either anthracycline-based regimen with a taxane, or Taxotere with carboplatin; [c] HER2 therapy for 1 year (52 weeks). Abbreviations: HER human epidermal growth-factor receptor; IV: intravenous; q3 weeks: every 3 weeks.
Figure 6B:
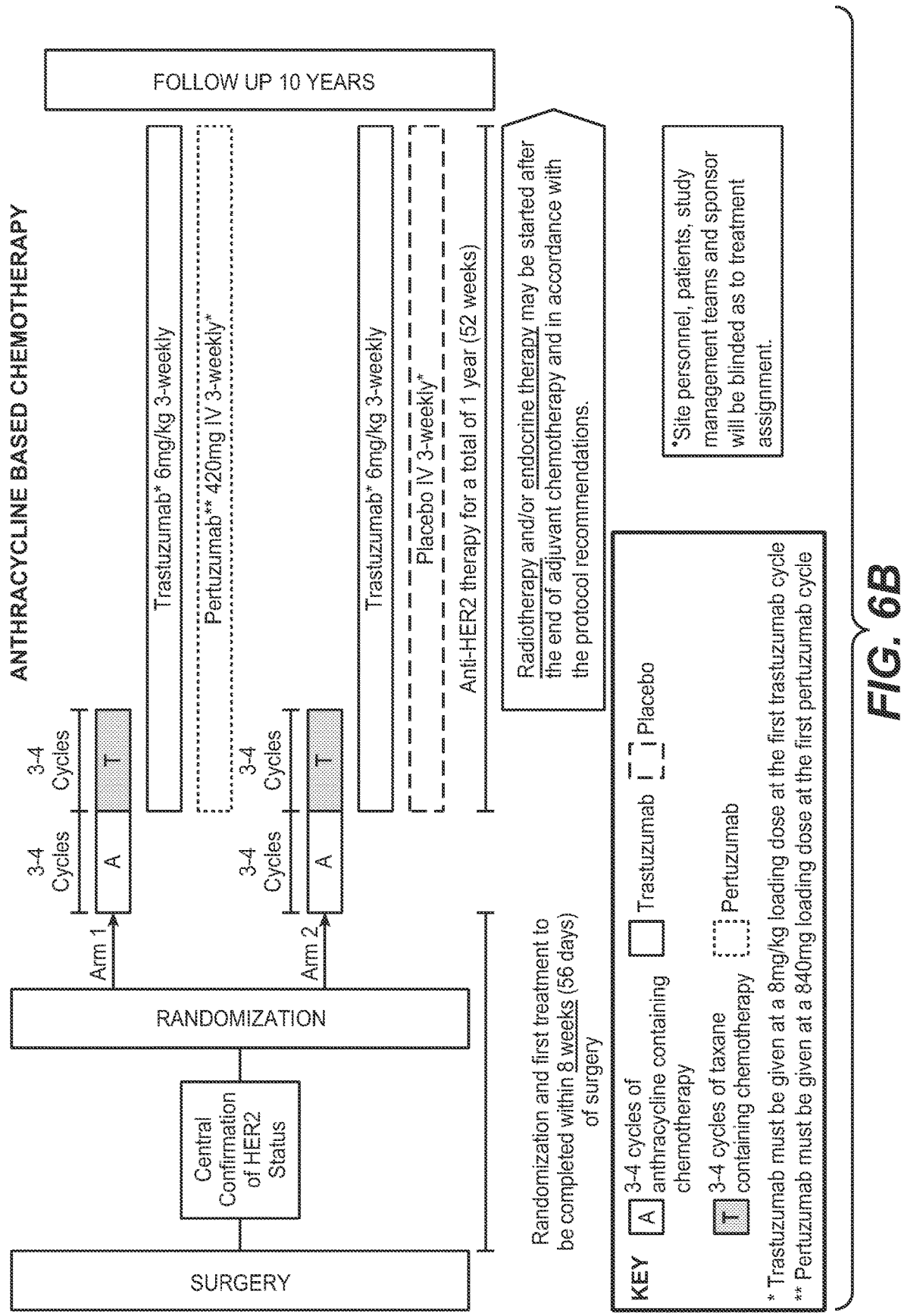
FIG. 6B shows the study design of the APHINITY clinical trial, using anthracycline based chemotherapy
Figure 6C:
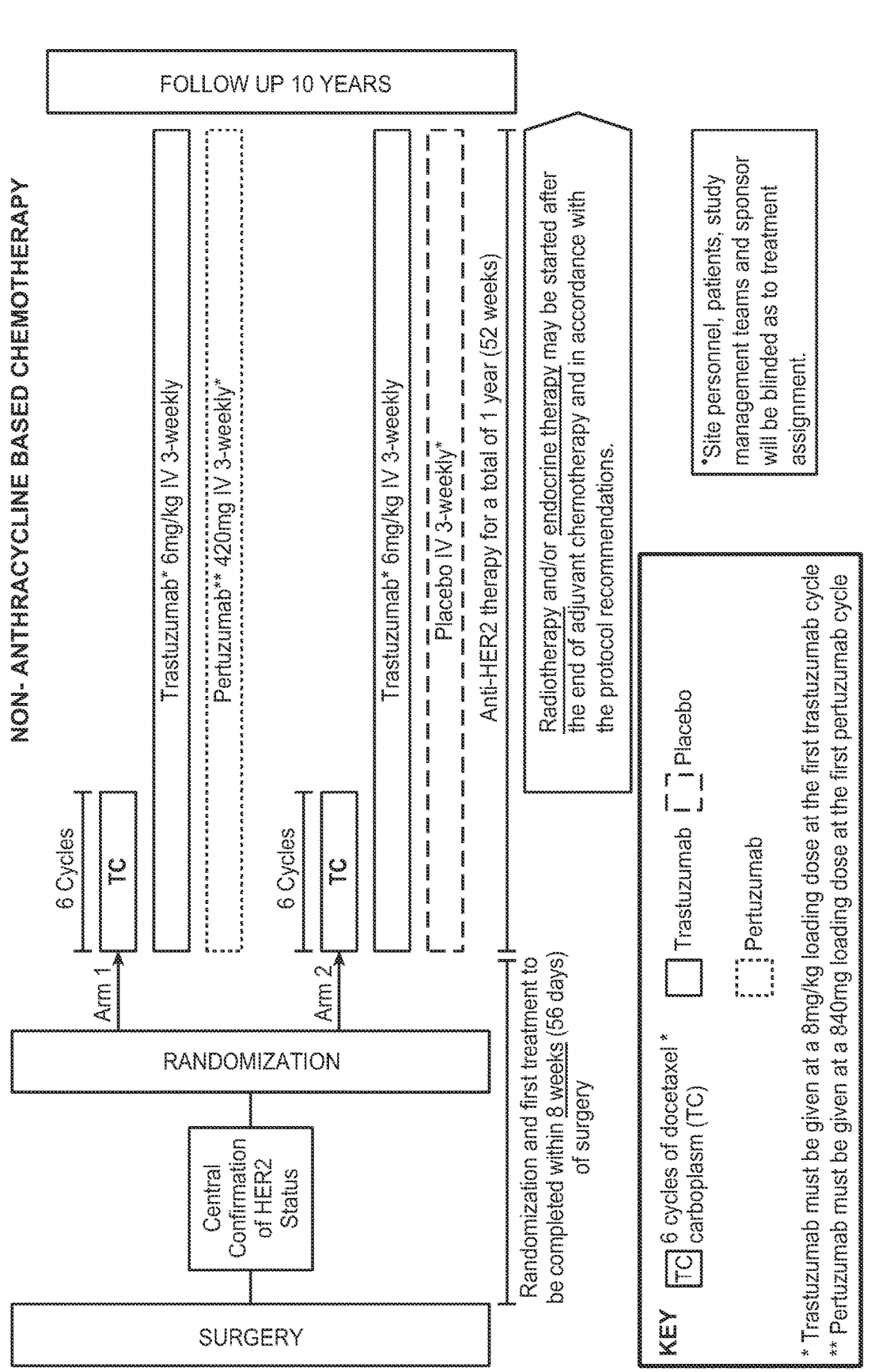
FIG. 6C shows the study design of the APHINITY clinical trial, using non-anthracycline based chemotherapy.

A schematic representation of the study design is shown in FIG. 6A, FIG. 6B, and FIG. 6C. Patients enrolled in the study underwent surgery and were randomized to one of two treatment groups (1:1) to receive either:

PERJETA® and HERCEPTIN® with six to eight cycles of chemotherapy (anthracycline or non-anthracycline containing regimen), followed by PERJETA® and HERCEPTIN® every three weeks for a total of one year (52 weeks) of treatment. In particular, in this experimental arm, participants receive pertuzumab IV and trastuzumab IV q3w for 1 year of treatment in combination with chemotherapy according to one of the following schedules (as per Investigator's discretion): 1) 3-4 cycles (q3w) of 5-fluorouracil+epirubicin or doxorubicin+cyclophosphamide followed by either 4 cycles (q3w) of docetaxel or 12 weekly cycles of paclitaxel. 2) 4 cycles (q3w) of doxorubicin or epirubicin+cyclophosphamide followed by either 4 cycles (q3w) of docetaxel or 12 weekly cycles of paclitaxel. 3) (Non-Anthracycline therapy) 6 cycles (q3w) of docetaxel+carboplatin.

Placebo and HERCEPTIN® with six to eight cycles of chemotherapy (anthracycline or non-anthracycline containing regimen), followed by placebo and HERCEPTIN® every three weeks for a total of one year (52 weeks) of treatment. In particular, in this placebo comparator arm participants receive placebo IV and trastuzumab IV q3w for 1 year of treatment in combination with chemotherapy according to one of the following schedules (as per Investigator's discretion): 1) 3-4 cycles (q3w) of 5-fluorouracil+epirubicin or doxorubicin+cyclophosphamide followed by either 4 cycles (q3w) of docetaxel or 12 weekly cycles of paclitaxel. 2) 4 cycles (q3w) of doxorubicin or epirubicin+cyclophosphamide followed by either 4 cycles (q3w) of docetaxel or 12 weekly cycles of paclitaxel. 3) (Non-Anthracycline therapy) 6 cycles (q3w) of docetaxel+carboplatin.

Drug Pertuzumab: Participants received pertuzumab loading dose of 840 mg IV in Cycle 1, followed by 420 mg IV q3w.

Drug Trastuzumab: Participants received trastuzumab at a loading dose of 8 milligrams per kilogram (mg/kg) followed by 6 mg/kg IV q3w.

Drug: 5-Fluorouracil: Participants may receive 5-fluorouracil 500-600 milligrams per square meter (mg/m$^2$) IV q3w.

Drug: Carboplatin: Participants may receive carboplatin dose of 6 times Area Under the Concentration Time Curve (AUC) (maximum dose of 900 mg) IV q3w.

Drug: Cyclophosphamide: Participants may receive cyclophosphamide 500-600 mg/m$^2$ IV q3w.

Drug: Docetaxel: Participants may receive docetaxel either 75 mg/m$^2$ IV q3w, or 100 mg/m$^2$ IV q3w, or 75 mg/m$^2$ IV q3w for first cycle followed by 100 mg/m$^2$ IV q3w.

Drug: Doxorubicin: Participants may receive doxorubicin 50 mg/m$^2$ IV q3w.

Drug: Epirubicin: Participants may receive epirubicin 90-120 mg/m$^2$ IV q3w.

Drug: Paclitaxel: Participants may receive paclitaxel 80 mg/m$^2$ IV once weekly.

Radiotherapy and/or endocrine therapy could be initiated at the end of adjuvant therapy. The APHINITY study allowed for standard adjuvant chemotherapy regimens to be used. Both lymph node-positive and lymph node-negative participants were eligible for enrolment (see below).

Eligibility
　Ages eligible for study: 18 year and older (adult, senior)
　Sexes eligible for study: All
　Accepts healthy volunteers: No
Inclusion Criteria
　Non-metastatic operable primary invasive HER2-positive carcinoma of the breast that is histologically confirmed, and adequately excised
　Lymph node positive disease, or node negative disease (pN0) and a tumor size of >1.0 cm. Patients with pN0 tumors and a tumor size between 0.5-1.0 cm were initially eligible if at least one of the following features was present: grade 3, both hormone receptors negative, or age <35 years. Patients with pN0 were no longer eligible under a protocol amendment after 3655 patients were randomized.
　Eastern Cooperative Oncology Group (ECOG) performance status less than or equal to (</=) 1
　The interval between definitive surgery for breast cancer and the first dose of chemotherapy must be no more than 8 weeks (56 days). The first cycle of chemotherapy must be administered within 7 days of randomization or on Day 56, whichever occurs first
　Known hormone receptor status (estrogen receptor and progesterone receptor)
　Baseline LVEF greater than or equal to (>/=) 55 percent (%) measured by echocardiogram (ECHO) or Multiple-Gated Acquisition (MUGA) Scan
　Confirmed HER2 positive status, which requires confirmation that the patient's breast cancer has an immunohistochemistry score 3+ in >10% immunoreactive cells or c-erbB2 gene amplification by in situ hybridization (ratio of c-erbB2 gene signals to centromere 17 signals ≥2).
　Women of childbearing potential and male participants with partners of childbearing potential must agree to use effective contraception (as defined by the protocol) by the participant and/or partner for the duration of the study treatment and for at least 7 months after the last dose of study drug.
Exclusion Criteria
　History of any prior (ipsi- and/or contralateral) invasive breast cancer
　History of non-breast malignancies within the 5 years prior to study entry, except for carcinoma in situ of the cervix, carcinoma in situ of the colon, melanoma in situ, and basal cell and squamous cell carcinomas of the skin
　Any "clinical" T4 tumor as defined by Primary tumor/regional lymph nodes/distant metastasis (TNM), including inflammatory breast cancer
　Any previous systemic chemotherapy for cancer or radiotherapy for cancer
　Prior use of anti-HER2 therapy for any reason or other prior biologic or immunotherapy for cancer
　Concurrent anti-cancer treatment in another investigational trial
　Serious cardiac or cardiovascular disease or condition
　Other concurrent serious diseases that may interfere with planned treatment including severe pulmonary conditions/illness
　Abnormal laboratory tests immediately prior to randomization
　Pregnant or lactating women
　Sensitivity to any of the study medications or any of the ingredients or excipients of these medications
Outcome Measures
　A complete list of primary and secondary outcome measures of the study are listed below.
　One primary efficacy endpoint of the APHINITY study is IDFS, which is the time a patient lives without return of invasive breast cancer at any site or death from any cause after adjuvant treatment.
　The stratified log-rank test was used to compare IDFS between the two treatment groups. The Kaplan-Meier approach was used to estimate 3-year IDFS percentages for each treatment group. The stratified Cox proportional hazards model was used to estimate the hazard ratio (HR) between the two treatment groups and its 95% confidence interval (CI). The primary analysis was based on the intent-to-treat (ITT) population. The study was designed to have 80% power to detect a hazard ratio of 0.75 at a 5%, 2-sided significance level. A 3-year IDFS percentage of 89.2% was assumed for the placebo group on the basis of the findings of the BCIRG 006 study (NCT00021255). Under these assumptions approximately 379 IDFS events are required for the primary analysis of IDFS.

Secondary efficacy endpoints include cardiac and overall safety, overall survival, disease free survival and health-related quality of life.

Distant Recurrence-Free Interval (DRFI) is defined as the time between randomization and the date of distant breast cancer recurrence. Patients without distant disease recurrence at the time of analysis will be censored at the date of death or last known alive date. The definitive (final event-driven) OS analysis is planned when 640 deaths have occurred. The first interim analysis of OS is be made available at the time of the primary analysis of IDFS, with limited information compared to the definitive analysis. Two subsequent interim analysis will be performed. For regulatory purposes, the overall alpha-level will be controlled at 0.05 for the four OS analyses. The adjusted two-sided significance level at the first interim analysis of OS is <0.00001.

Patients who receive any amount of study treatment (chemotherapy or targeted therapy) were included in safety analyses by the treatment patients actually received. Patients who received adjuvant pertuzumab are in the pertuzumab safety analysis population arm. Patients who received study medication but no pertuzumab are in the placebo safety analysis population arm.

Primary cardiac endpoint was severe congestive heart failure (CHF), defined as: heart failure NYHA Class III or IV and a drop in LVEF of at least 10 EF points from baseline and to below 50% or cardiac death. Cardiac death was identified by the APHINITY Cardiac Advisory Board (CAB).

A secondary cardiac endpoint was defined as an asymptomatic or mildly symptomatic (NYHA Class II) significant drop in LVEF by MUGA scan or ECHO, confirmed by a second LVEF assessment within approximately 3 weeks showing also a significant drop OR as confirmed by the APHINITY CAB.

Primary Outcome Measures
  Invasive Disease-Free Survival (IDFS) Duration (Excluding Second Primary Non-Breast Cancers as IDFS Event), as Assessed Using Radiologic, Histologic Examinations or Laboratory Findings [Time Frame: Randomization until protocol defined IDFS event (excluding second primary non-breast cancers) (up to 12 years overall)]
  Percentage of Participants with Both a Heart Failure of New York Heart Association (NYHA) Class III or IV and a Drop in Left Ventricular Ejection Fraction (LVEF) of at least 10 Points from Baseline and to Below 50 Percent (%) [Time Frame: Baseline up to 12 years (assessed every 12 weeks up to first 12 months; months 18, 24, 30, 36, 48, 60 and every 12 months thereafter up to 12 years overall)]

Secondary Outcome Measures
  IDFS Duration (Including Second Primary Non-Breast Cancers as IDFS Event), as Assessed Using Radiologic, Histologic Examinations or Laboratory Findings [Time Frame: Randomization until protocol defined IDFS event (including second primary non-breast cancers) (up to 12 years overall)]
  Disease-Free Survival (DFS) Duration (Including Second Primary Non-Breast Cancers or Contralateral or Ipsilateral Ductal Carcinoma in-Situ as an Event), as Assessed Using Radiologic, Histologic Examinations or Laboratory Findings [Time Frame: Randomization until protocol defined DFS event (including second primary non-breast cancers or contralateral or ipsilateral ductal carcinoma in-situ) (up to 12 years overall)]
  Overall Survival (OS) [Time Frame: Randomization until death due to any cause (up to 12 years overall)]
  Recurrence-Free Interval (RFI), as Assessed Using Radiologic, Histologic Examinations or Laboratory Findings [Time Frame: Randomization until local, regional or distant breast cancer recurrence (up to 12 years overall)]
  Distant Recurrence-Free Interval (DRFI), as Assessed Using Radiologic, Histologic Examinations or Laboratory Findings [Time Frame: Randomization until distant breast cancer recurrence (up to 12 years overall)]
  Percentage of Participants with Adverse Events [Time Frame: Baseline up to 12 years]
  Percentage of Participants with Asymptomatic or Mildly Symptomatic (NYHA Class II) Drop in Left Ventricular Ejection Fraction (LVEF) of at least 10 Points from Baseline and to Below 50% [Time Frame: Baseline up to 12 years (assessed every 12 weeks up to first 12 months; months 18, 24, 30, 36, 48, 60 and every 12 months thereafter up to 12 years overall)]
  LVEF Measurements Over the Course of the Study [Time Frame: Baseline up to 12 years (assessed every 12 weeks up to first 12 months; months 18, 24, 30, 36, 48, 60 and every 12 months thereafter up to 12 years overall)]
  European Organization for Research and Treatment of Cancer Quality of Life Questionnaire—Core 30 (EORTC QLQ-C30) Score [Time Frame: Baseline, Weeks 10, 13, 19, and 25; 28-days after last dose of study medication (Week 56); and Months 18, 24, and 36]
  European Organization for Research and Treatment of Cancer Breast Cancer Module Quality of Life (EORTC QLQ BR23) Functional Scale Score [Time Frame: Baseline, Weeks 10, 13, 19, and 25; 28-days after last dose of study medication (Week 56); and Months 18, 24, and 36]
  European Quality of Life-5 Dimensions (EQ-5D) Questionnaire Score [Time Frame: Baseline, Weeks 10, 13, 19, and 25; 28-days after last dose of study medication (Week 56); and Months 18, 24, and 36.]

Formulation, Packaging, and Handling

PERJETA® is provided as a single-use formulation containing 30 mg/mL pertuzumab formulated in 20 mM L-histidine (pH 6.0), 120 mM sucrose, and 0.02% polysorbate-20. Each 20-cc vial contains approximately 420 mg of pertuzumab (14.0 mL/vial). For further details, refer to the PERJETA® IB or local prescribing information for PERJETA®.

Labeling of PERJETA®

PERJETA® will be labeled according to the regulatory requirements in each country, as well as in accordance with International Conference of Harmonisation (ICH) Good Clinical Practice. The study Sponsor will provide PERJETA® to all study sites labeled for investigational use only.

Storage of PERJETA®

Vials of PERJETA® are shipped at a temperature ranging from 2° C.-8° C. (36° F.-46° F.), and must be placed in a refrigerator (same temperature range) immediately upon receipt to ensure optimal retention of physical and biochemical integrity, and should remain refrigerated until immediately prior to use. Temperature logs must be maintained (in accordance with local pharmacy practice) on the refrigerator to ensure proper storage conditions. If a temperature deviation from the allowed 2° C.-8° C. is found either during shipment or storage, contact the Sponsor to determine if the drug is still appropriate for use.

The PERJETA® vials may not be shaken. All vials should be stored within the outer carton and protected from light. The medication must not be used beyond the use by date information provided on the IMP kit label.

Preparation of PERJETA®

Because the PERJETA® formulation does not contain a preservative, the vial seal may only be punctured once. Any remaining solution should be discarded.

The indicated volume of PERJETA® solution should be withdrawn from the vials and added to a 250-cc IV bag of 0.9% sodium chloride injection. The bag should be gently inverted to mix the solution, but should not be shaken vigorously. The solution should be visually inspected for particulates and discoloration prior to administration. The entire volume within the bag should be administered as a continuous IV infusion. The volume contained in the administration tubing should be completely flushed using a 0.9% sodium chloride injection.

The solution of PERJETA® for infusion, diluted in polyvinyl chloride (PVC) or non-PVC polyolefin bags containing 0.9% sodium chloride injection, may be stored at 2° C.-8° C. (36° F.-46° F.) for up to 24 hours prior to use. Diluted PERJETA® has been shown to be stable for up to 24 hours at room temperature (2° C.-25° C.). However, because diluted PERJETA®) contains no preservative, the aseptically diluted solution should be stored refrigerated (2° C.-8° C.) for no more than 24 hours.

A rate-regulating device may be used for all study-drug infusions. When the study drug IV bag is empty, 50 mL of 0.9% sodium chloride injection may be added to the IV bag or an additional bag may be hung, and the infusion may be continued for a volume equal to that of the tubing to ensure complete delivery of the study drug.

If extravasation of the study drug infusion occurs, the following steps should be taken:

Discontinue the infusion.

Treat the extravasation according to institutional guidelines for extravasation of a non-caustic agent.

If a significant volume of the study drug infusion remains, restart the infusion at a more proximal site in the same limb or on the other side.

Formulation of HERCEPTIN®

HERCEPTIN® (lyophilized formulation) for use in this study will be supplied by the Sponsor, as a freeze-dried preparation. All HERCEPTIN® is supplied for parenteral IV administration; subcutaneous HERCEPTIN® is not permitted in this study. HERCEPTIN® is formulated in histidine, trehalose, and polysorbate 20. HERCEPTIN® for use in this study will be supplied by the Sponsor in vials containing a freeze-dried preparation for parenteral administration. For IV administration, each vial of HERCEPTIN® is reconstituted with Sterile Water for Injection (SWFI) dependent on the vial size, as follows:

HERCEPTIN® 440-mg vial is mixed with 20.0 mL of SWFI (not supplied)

HERCEPTIN® 150-mg vial is mixed with 7.2 mL of SWFI (not supplied)

Use of other reconstitution solvents is not allowed. The reconstituted solution contains 21 mg/mL trastuzumab and will be added to 250 mL of 0.9% sodium chloride injection for administration to the patient. None of the HERCEPTIN® formulations contains a preservative. The product is not intended to be stored after reconstitution and dilution unless this has taken place under aseptic conditions. Therefore, once the infusion is prepared, it is for single use only and should be administered promptly. The dose must be infused within 8 hours after reconstitution unless aseptically prepared and stored at 2° C.-8° C. (maximum refrigerated storage time is 24 hours). Each HERCEPTIN® vial provided for this study is to be used as a SINGLE DOSE VIAL ONLY. Each vial should not be used for more than one administration of Herceptin and not for more than 1 patient at a time. DO NOT FREEZE HERCEPTIN THAT HAS BEEN RECONSTITUTED.

Labeling of HERCEPTIN®

HERCEPTIN® will be labeled according to the regulatory requirements in each country, as well as in accordance with ICH Good Clinical Practice. The study Sponsor will provide HERCEPTIN® to all study sites labeled for investigational use only.

Storage of HERCEPTIN®

Vials of HERCEPTIN® are shipped with cool packs at a temperature ranging from 2° C. to 8° C. (36° F. to 46° F.) and must be placed in a refrigerator (same temperature range) immediately upon receipt to ensure optimal retention of physical and biochemical integrity. Temperature logs must be maintained (in accordance with local pharmacy practice) on the refrigerator to ensure proper storage conditions. Do not use beyond the use by date stamped on the vial. DO NOT FREEZE.

HERCEPTIN® may be sensitive to shear-induced stress (e.g., agitation or rapid expulsion from a syringe). DO NOT SHAKE. Vigorous handling of solutions of HERCEPTIN® results in aggregation of the protein and may create cloudy solutions. HERCEPTIN® should be carefully handled during reconstitution. Causing excessive foaming during reconstitution or shaking the reconstituted HERCEPTIN® may result in problems with the amount of HERCEPTIN® that can be withdrawn from the vial.

Preparation of HERCEPTIN®

Appropriate aseptic technique should be used when preparing the study drug. Each vial of HERCEPTIN® is reconstituted with SWFI as described above. HERCEPTIN® should be carefully handled during reconstitution. Causing excessive foaming during reconstitution or shaking the reconstituted HERCEPTIN® may result in problems with the amount of HERCEPTIN® that can be withdrawn from the vial.

The following instructions have to be followed:

1. Using a sterile syringe, slowly inject the sterile water for injection in the vial containing the lyophilized HERCEPTIN®, directing the stream into the lyophilized cake.

2. Swirl vial gently to aid reconstitution. DO NOT SHAKE!

Slight foaming of the product upon reconstitution is not unusual. Allow the vial to stand undisturbed for approximately 5 minutes. The reconstituted HERCEPTIN® results in a colorless to pale yellow transparent solution and should be essentially free of visible particulates.

Do not refrigerate or freeze HERCEPTIN® that has been reconstituted.

Drug Preparation: Dilution

The reconstituted solution will be added to an infusion bag containing 250 mL of 0.9% Sodium Chloride Injection, United States Pharmacopeia. Once the infusion is prepared, it should be administered immediately. If diluted aseptically, it may be stored for a maximum of 24 hours from reconstitution (do not store above 30° C.).

Results

The study met its primary endpoint and showed that adjuvant (after surgery) treatment with the PERJETA®-HERCEPTIN® combination significantly reduced the risk of recurrence of invasive disease or death (invasive Disease Free Survival; IDFS) in people with HER2-positive eBC compared to HERCEPTIN® and chemotherapy alone. The results presented in 7 A&B, 8 A-C, 9 A-C discussed below represent the results of the study's primary analysis of IDFS (based on data collected on the electronic Case Report Form "eCRF").

Figure 7B:
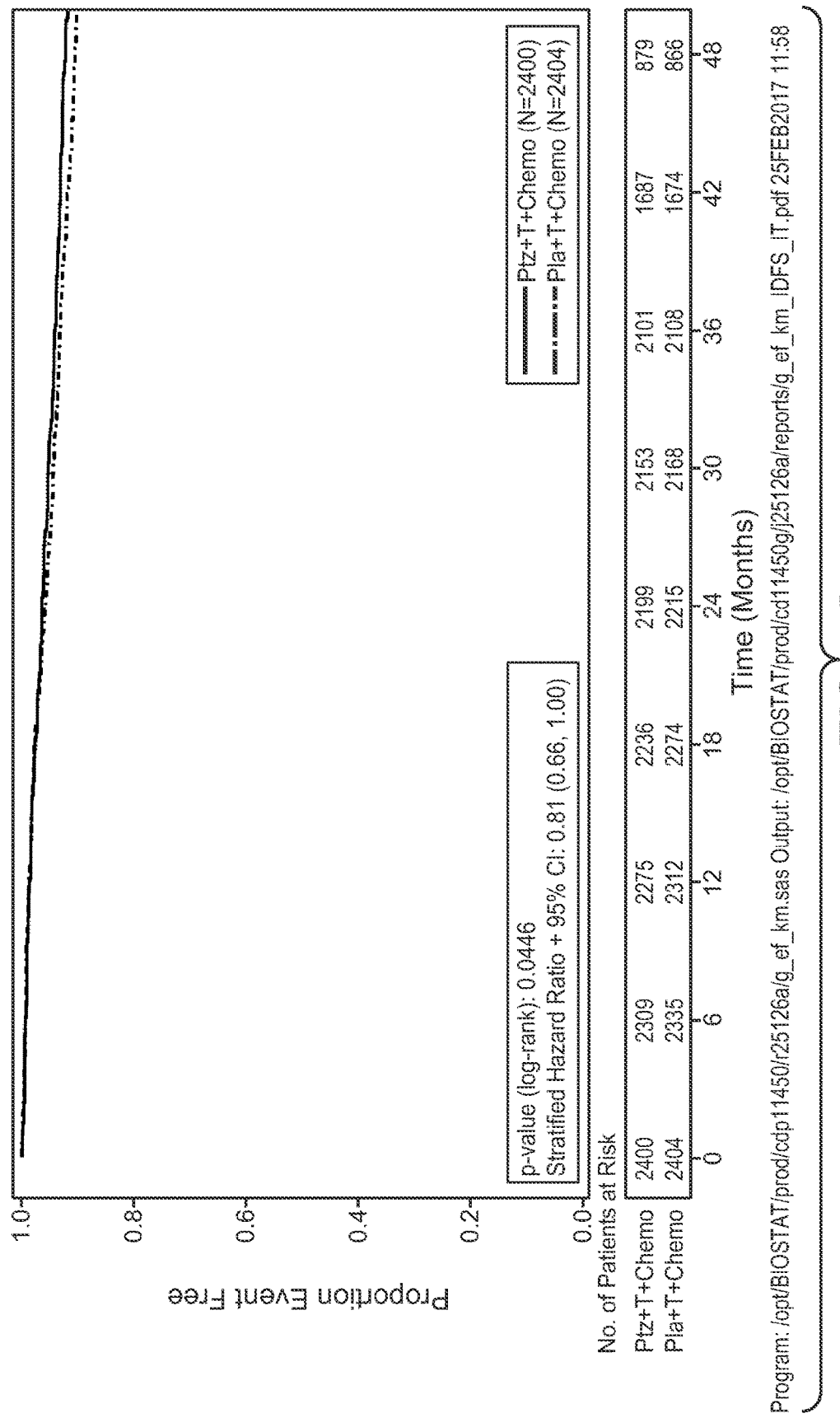
FIG. 7B shows a Kaplan-Meier plot of Distant Recurrence-Free Interval (months) in patients treated with pertuzumab+trastuzumab (n=2400) and placebo+trastuzumab (n=2404), respectively, as described in Example 1.

Primary Endpoint:
As shown in FIG. 7A, Hazard Ratio (HR) for IDFS was 0.81; [95% CI 0.66-1.00; p=0.0446], representing a 19% reduction in the risk of recurrence of invasive breast cancer or death for patients in the PERJETA®-HERCEPTIN® arm compared with the HERCEPTIN® control arm. See also the Kaplan-Meier plot shown in FIG. 7B.

The corresponding estimates of three-year IDFS rates were:
PERJETA®, HERCEPTIN® and chemotherapy arm=94.06%
Placebo, HERCEPTIN® and chemotherapy (control) arm=93.24%

Efficacy

The study met its primary study endpoint with a statistically significant improvement of invasive disease free survival (IDFS) with a hazard ration of 0.81 (95% CI, 0.66 to 1.00; P=0.0446) in favor of the pertuzumab group. After a median follow-up of 45.4 months, 171 (7.1%) IDFS events were reported in patients randomized to the pertuzumab group, and 210 (8.7%) events in patients randomized to the control group. The estimate of IDFS at 3-years was 94.1% in the pertuzumab group and 93.2% in the placebo group. Distant recurrence occurred as first IDFS even in 112 (4.7%) patients and 139 (5.8%) patients, in the pertuzumab and control group, respectively, whereas the numbers of patients with local recurrences were 16 (1.1%) and 34 (1.4%), respectively. Central nervous system (CNS) metastases occurred as the first IDFS event in 1.9% and 1.8% of patients in the pertuzumab and control group, respectively. A visceral or CNS site of first distant recurrence was more common than bone.

In a secondary analysis, second primary non-breast cancer events were also considered as IDFS events. The number of events increased to 189 and 230 in the pertuzumab and control group, respectively, resulting in a statistically significant hazard ratio of 0.82 (95% CI, 0.68 to 0.99; P=0.043).

The cardiac and overall safety profile of the PERJETA®-HERCEPTIN® combination was consistent with previous studies of PERJETA® and no new safety signals were identified.

Figure 8B:
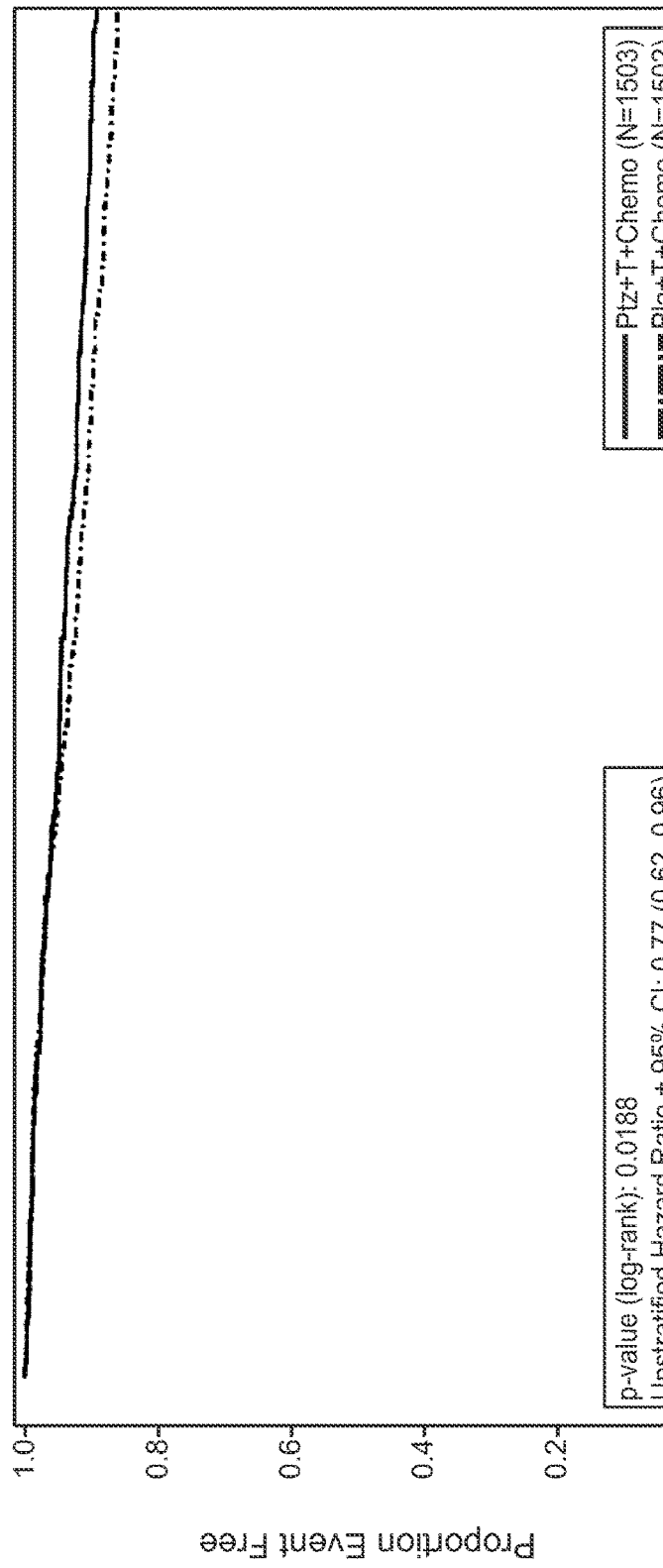
FIG. 8B shows a Kaplan-Meier plot of Time to First IDFS event (months) by treatment regimen in node positive cohort of breast cancer patients treated with pertuzumab+trastuzumab (n=1503) and placebo+trastuzumab (n=1502), respectively, as described in Example 1.
Figure 8C:
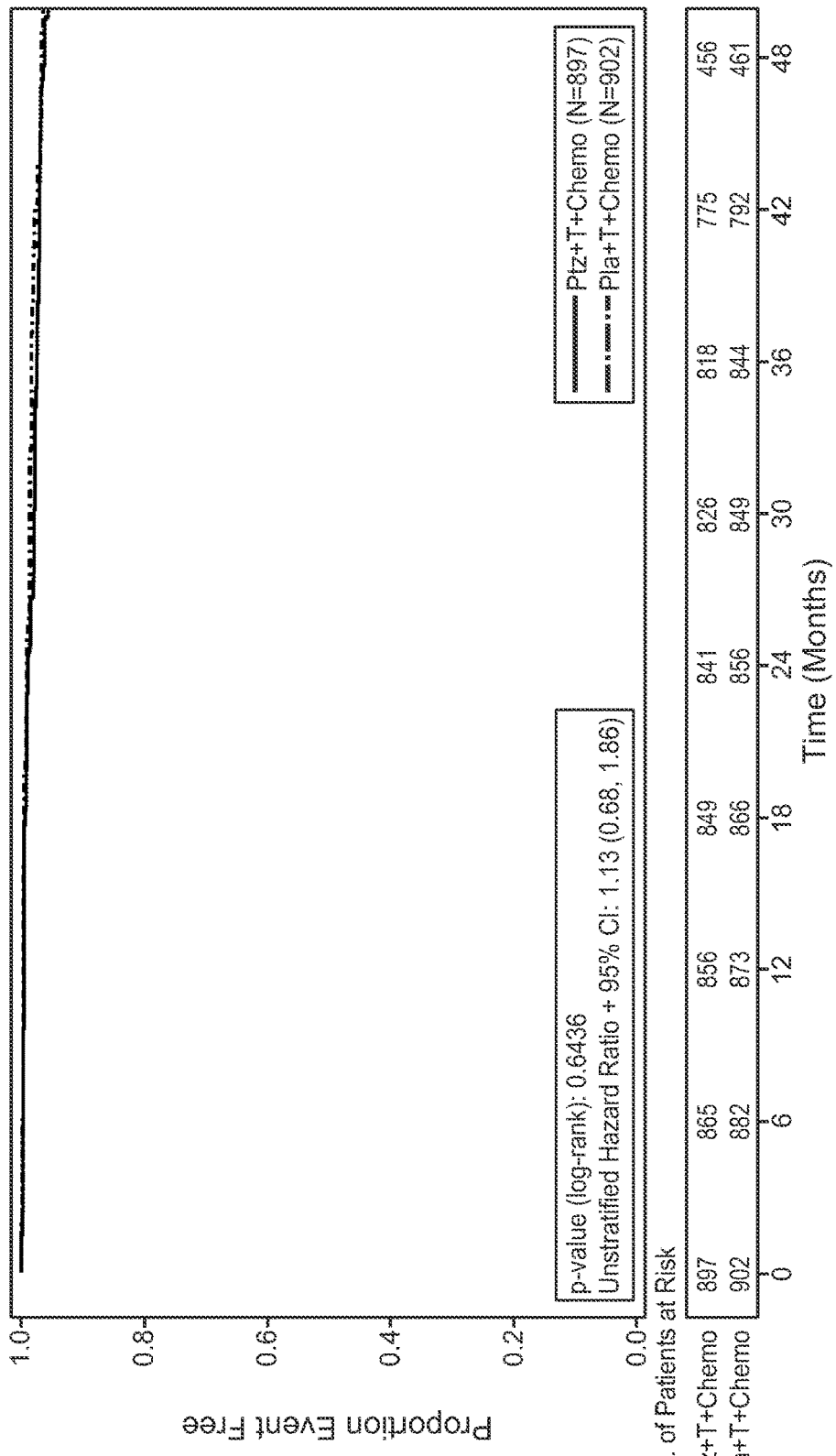
FIG. 8C shows a Kaplan-Meier plot of Time to First IDFS event (months) by treatment regimen in node negative cohort of breast cancer patients treated with pertuzumab+trastuzumab (n=987) and placebo+trastuzumab (n=902), respectively, as described in Example 1.
Figure 9B:
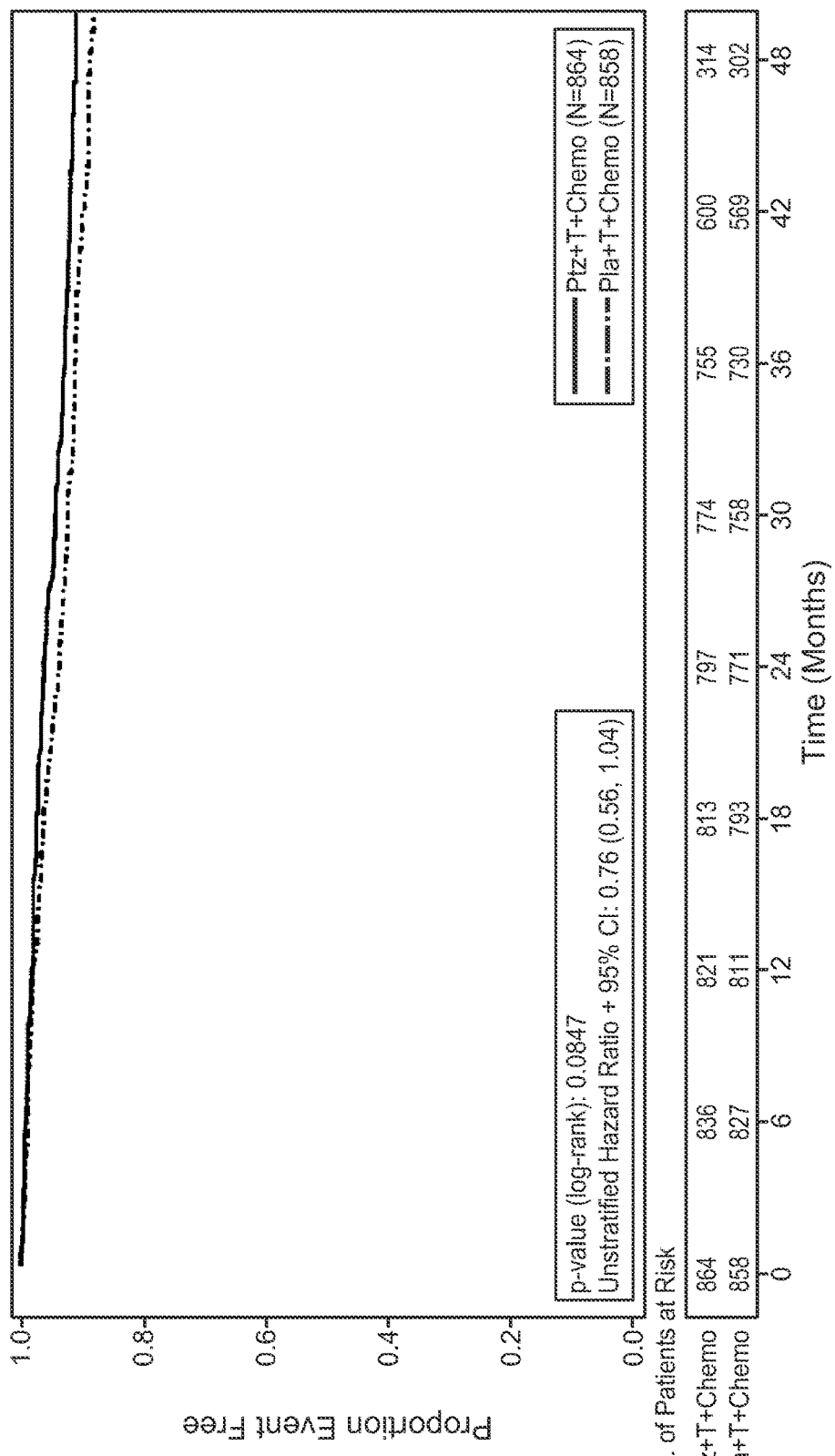
FIG. 9B shows a Kaplan-Meier plot of Time to First IDFS event (months) by treatment regimen in central hormone receptor negative patients treated with pertuzumab+trastuzumab (n=864) and placebo+trastuzumab (n=858), respectively, as described in Example 1.

Although the positive effects of including pertuzumab in the treatment regimen were homogenously observed in various subgroups of patients, subgroup analyses for IDFS revealed that the treatment effect was the most pronounced in the lymph node positive (FIG. 8A and FIG. 8B) and hormone receptor (HR) negative patients (FIG. 9A and FIG. 9B). As shown in FIG. 8A, in patients with node-positive disease, there were 139 (9.2%) IDFS events in the pertuzumab group and 181 (12.1%) IDFS events in the placebo group. The 3-year IDFS percentages were 92.0% in the pertuzumab group and 90.2% in the placebo group. The hazard ratio was 0.77 (95% CI 0.62-0.96; P=0.0188). The curves of the Kaplan-Meier plot started to separate 2 years after randomization (FIG. 8B). In contrast, patients with node-negative disease showed a very low number of IDFS events (32 [3.6%] with pertuzumab and 29 [3.2%] with placebo) and no treatment effect was detectable (hazard ratio 1.13 (95% CI 0.68-1.86; P=0.6436) (FIG. 8C).

Figure 9C:
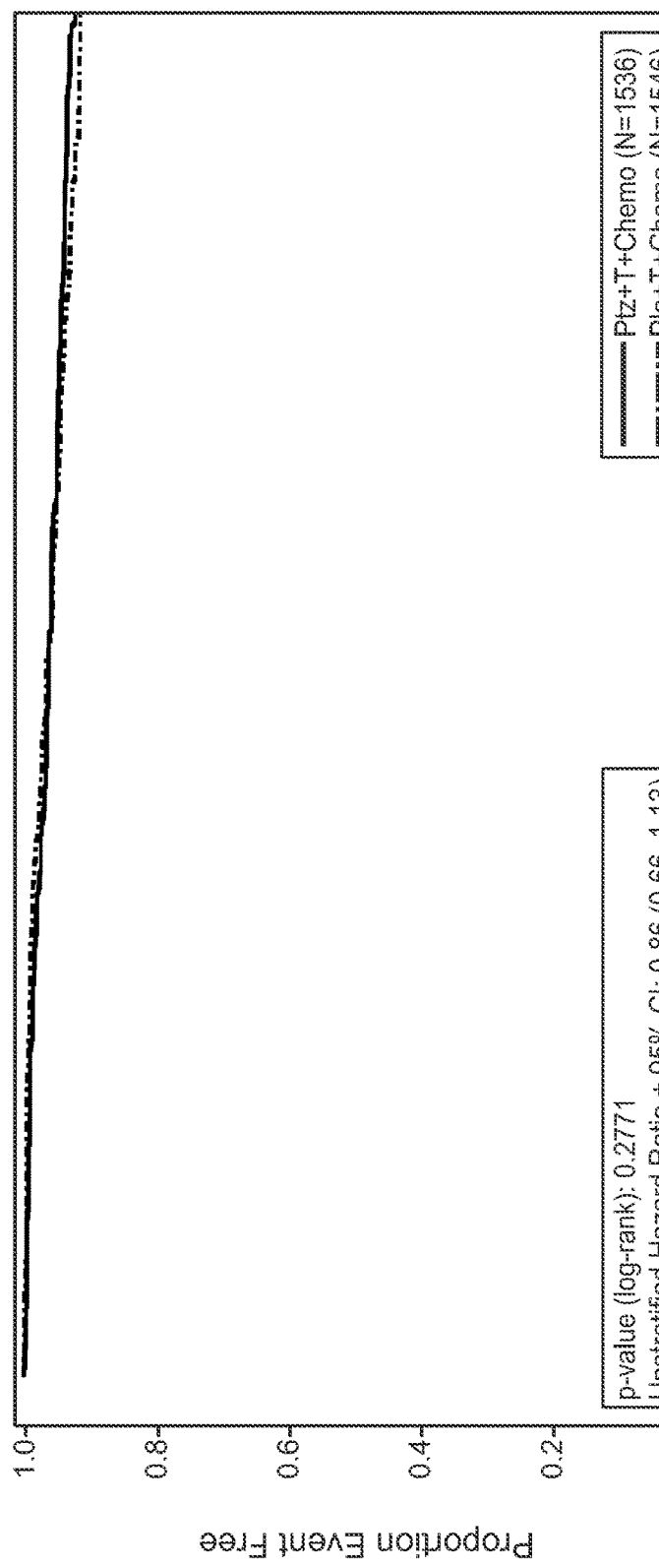
FIG. 9C shows a Kaplan-Meier plot of Time to First IDFS event (months) by treatment regimen in central hormone receptor positive patients treated with pertuzumab+trastuzumab (n=1536) and placebo+trastuzumab (n=1546), respectively, as described in Example 1.

In patients with hormone-receptor-negative tumors, there were 71 (8.2%) IDFS events in the for pertuzumab group 91 (10.6) in the for placebo group, leading to a hazard ratio of 0.76 (0.56-1.04; P=0.0847). The 3 year IDFS percentages were 92.8% in the pertuzumab group and 91.2% in the placebo group (FIG. 9A and FIG. 9B). The number of events was very low in patients with hormone-receptor-positive tumors (100 [6.5%] in the pertuzumab group and 119 [7.7%] in the placebo group), resulting in a hazard ratio of 0.86 (0.66-1.13) (P=0.2771). The 3 year IDFS percentages were 94.8% in the pertuzumab group and 94.4% in the placebo group (FIG. 9C).

At the time of this primary endpoint analysis a first interim analysis for overall survival was performed, with 80 deaths in the pertuzumab arm and 89 deaths in the placebo arm. There was no significant treatment effect at this early point of time (hazard ratio 0.89; 95% CI 0.66-1.21; P=0.4673).

Figure 10:
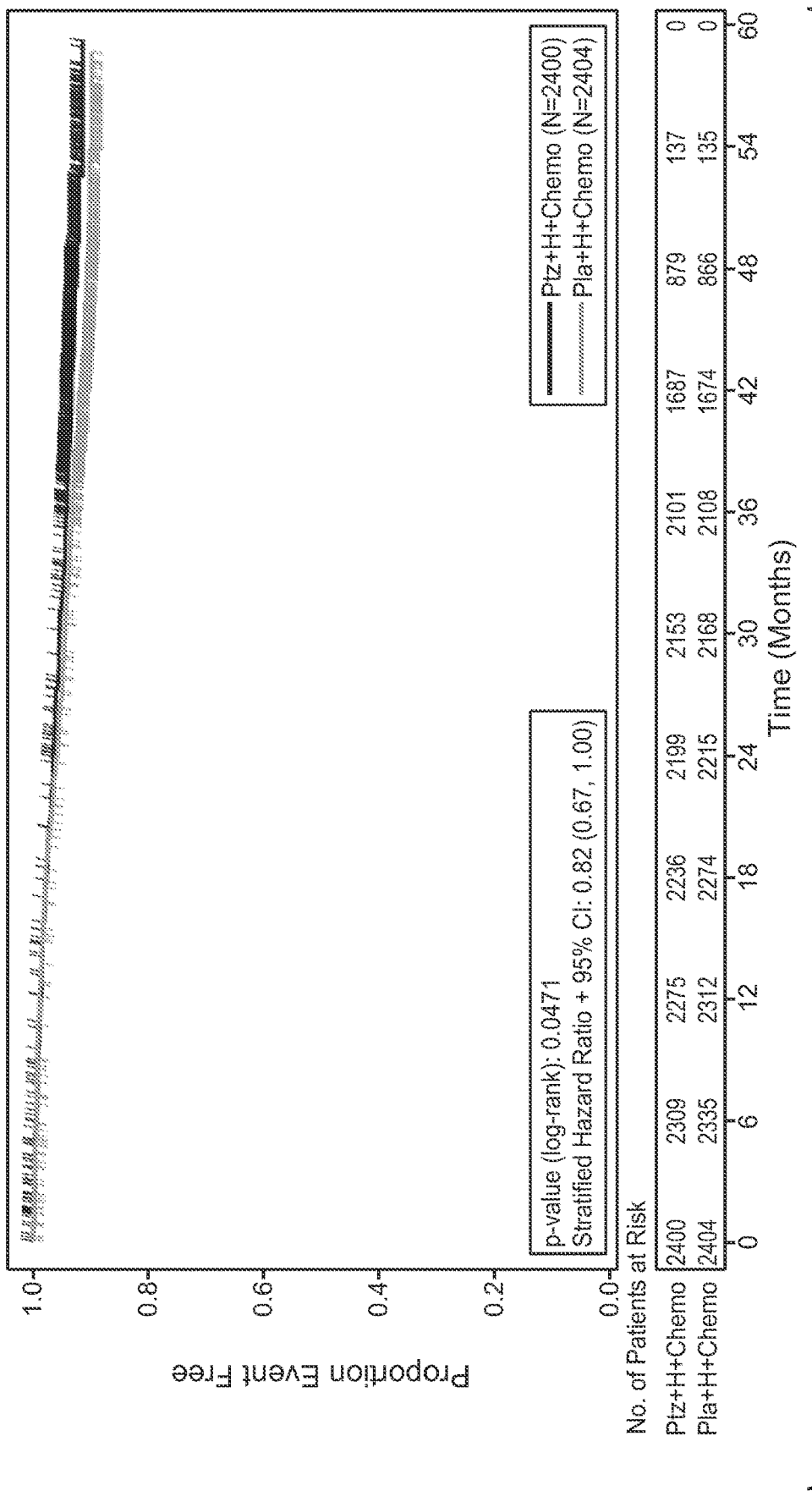
FIG. 10 shows a Kaplan-Meier plot of Time to First IDFS event (months), showing censored patients, by Treatment Regimen (patients treated with pertuzumab (Ptz)+trastuzumab (H)+chemo (n=2400) and placebo (Pla)+trastuzumab+chemo (n=2404), respectively), ITT population, as described in Example 1.

FIG. 10 and Tables 3 and 4 below present the results of the APHINTY study's pre-specified sensitivity analysis of the primary IDFS endpoint, based on the stratification factors data collected by the Interactive web/voice Response System "IxRS".

TABLE 3

Efficacy Results from APHINITY Clinical Study

|  | PERJETA + trastuzumab + chemotherapy N = 2400 | Placebo + trastuzumab + chemotherapy N = 2404 |
|---|---|---|
| Invasive Disease Free Survival (IDFS) | | |
| Number (%) of patients with event | 171 (7.1%) | 210 (8.7%) |
| HR [95% CI][1] | 0.82 [0.67, 1.00] | |
| p-value (Log-Rank test, stratified[1]) | 0.047 | |
| 3 year event-free rate[2], % [95% CI] | 94.1 [93.1, 95.0] | 93.2 [92.2, 94.3] |
| IDFS including second primary non-breast cancer | | |
| Number (%) of patients with event | 189 (7.9%) | 230 (9.6%) |
| HR [95% CI][1] | 0.83 [0.68, 1.00] | |
| 3 year event-free rate[2], % [95% CI] | 93.5 [92.5, 94.5] | 92.5 [91.4, 93.6] |
| Disease Free Survival (DFS) | | |
| Number (%) of patients with event | 192 (8.0%) | 236 (9.8%) |
| HR [95% CI][1] | 0.82 [0.68, 0.99] | |
| 3 year event-free rate[2], % [95% CI] | 93.4 [92.4, 94.4] | 92.3 [91.2, 93.4] |

TABLE 3-continued

Efficacy Results from APHINITY Clinical Study

|  | PERJETA + trastuzumab + chemotherapy N = 2400 | Placebo + trastuzumab + chemotherapy N = 2404 |
|---|---|---|
| Overall Survival (OS)[3] | | |
| Number (%) of patients with event | 80 (3.3%) | 89 (3.7%) |
| HR [95% CI][1] | 0.89 [0.66, 1.21] | |
| 3 year event-free rate[2], % [95% CI] | 97.7 [97.0, 98.3] | 97.7 [97.1, 98.3] |

HR = Hazard Ratio, CI = Confidence Interval
[1] All analyses stratified by nodal status, protocol version, central hormone receptor status, and adjuvant chemotherapy regimen. Stratification factors are defined according to the randomization data for IDFS.
[2] 3-year event-free rate derived from Kaplan-Meier estimates
[3] Data from first interim analysis

TABLE 4

Efficacy Results by Baseline Disease Characteristics and Adjuvant Chemotherapy from APHINITY Clinical Study[1]

| | Number of events/Total N (%) | | IDFS at 3 year (%, 95% CI) | | |
|---|---|---|---|---|---|
| Population | PERJETA + trastuzumab + chemotherapy | Placebo + trastuzumab + chemotherapy | PERJETA + trastuzumab + chemotherapy | Placebo + trastuzumab + chemotherapy | Unstratified HR (95% CI) |
| Hormone Receptor Status | | | | | |
| Negative | 71/864 (8.2%) | 91/858 (10.6%) | 92.8 (90.8, 94.3) | 91.2 (89.0, 92.9) | 0.76 (0.56, 1.04) |
| Positive | 100/1536 (6.5%) | 119/1546 (7.7%) | 94.8 (93.5, 95.8) | 94.4 (93.1, 95.4) | 0.86 (0.66, 1.13) |
| Nodal Status | | | | | |
| Negative | 32/897 (3.6%) | 29/902 (3.2%) | 97.5 (96.3, 98.4) | 98.4 (97.3, 99.0) | 1.13 (0.68, 1.86) |
| Positive | 139/1503 (9.2%) | 181/1502 (12.1%) | 92.0 (90.5, 93.3) | 90.2 (88.5, 91.6) | 0.77 (0.62, 0.96) |
| Adjuvant Chemotherapy Regimen | | | | | |
| Anthracycline | 139/1865 (7.4%) | 171/1877 (9.1%) | 93.8 (92.6, 94.8) | 93.0 (91.8, 94.1) | 0.82 (0.66, 1.03) |
| Non-Anthracycline | 32/535 (6.0%) | 39/527 (7.4%) | 94.9 (92.6, 96.6) | 94.0 (91.5, 95.8) | 0.82 (0.51, 1.31) |

[1] Exploratory analyses without adjusting multiple comparisons, therefore, results are considered descriptive.

Safety

In patients with hormone-receptor-negative tumors, there were 71 (8.2%) IDFS events in the for pertuzumab arm 91 (10.6%) in the for placebo arm, leading to a hazard ratio of 0.76 (0.56-1.04; P=0.0847). The 3 year IDFS percentages were 92.8% in the pertuzumab arm and 91.2% in the placebo arm. The number of events was very low in patients with hormone-receptor-positive tumors (100 [6.5%] in the pertuzumab arm and 119 [7.7%] in the placebo arm), resulting in a hazard ratio of 0.86 (0.66-1.13) (P=0.2771). The 3 year IDFS percentages were 94.8% in the pertuzumab arm and 94.4% in the placebo arm.

At the time of this primary endpoint analysis a first interim analysis for overall survival was performed, with 80 deaths in the pertuzumab arm and 89 deaths in the placebo arm. There was no significant treatment effect at this early point of time (hazard ratio 0.89; 95% CI 0.66-1.21; P=0.4673).

Cardiac Safety

Patients who received at least one dose of study treatment (chemotherapy or targeted therapy) were included in safety analyses by the treatment patients actually received. Patients who received pertuzumab for adjuvant treatment are in the pertuzumab safety analysis population group. Patients who received study medication but no pertuzumab are in the control safety analysis population group.

Primary cardiac endpoint was severe congestive heart failure (CHF), defined as: heart failure NYHA Class III or IV and a drop in LVEF of at least 10 EF points from baseline and to below 50% or cardiac death. Cardiac death was prospectively defined by the APHINITY Cardiac Advisory Board (CAB).

A secondary cardiac endpoint was defined as an asymptomatic or mildly symptomatic (NYHA Class II) significant drop in LVEF by MUGA scan or ECHO, confirmed by a second LVEF assessment within approximately 3 weeks showing also a significant drop OR as confirmed by the APHINITY CAB.

Discussion

The APHINITY study is a large, adequately powered, placebo-controlled, phase III clinical study. Treatment effect was homogenous throughout all subgroups; however, at this early time point of analysis it appeared best detectable in patient at higher risk of relapse due to lymph node involvement or negative hormone-receptor status. The safety profile of pertuzumab given for one year in this combination was favorable and no new safety signal was observed when compared to the safety reported in in the metastatic or neoadjuvant settings.

Evaluation of patient benefit always has to relate the effect size with potential risks from side effects. A grade ≥3 diarrhea occurred in an excess of 6.2% with the addition of pertuzumab and might be not sufficiently treatable with anti-diarrheic medication and lead therefore to treatment discontinuation. Nevertheless the overall treatment discontinuation rate was only 2.9% higher with pertuzumab compared to placebo. Most importantly no statistical difference could be detected with regard to cardiac toxicity despite the large number of patients. Assuming that type of cardiac toxicity of pertuzumab is comparable to the type induced by trastuzumab, most cardiac events will be observed already at the current time of analysis and late cardiac events will be infrequent. The cardiac safety of pertuzumab was already demonstrated in previous trials in the metastatic setting (Swain et al., Oncologist. 2013; 18(3):257-64) and even for simultaneous application with trastuzumab and epirubicin in the neoadjuvant setting (Schneeweiss et al., Ann. Oncol. 2013 24(9); 278-84).

The importance of the finding of the APHINITY study goes beyond the application of pertuzumab as adjuvant treatment. This adjuvant study was also considered as a proof-of-concept for the surrogacy of pathological complete response (pCR) observed in neoadjuvant studies for long-term outcome. The NeoSphere study reported an increase of pCR rate from 29.0% after a 12 weeks treatment of docetaxel and trastuzumab to 45.8% after the same treatment but with the addition of pertuzumab (Gianni et al., Lancet Oncol. 2012 13(1):25-32). Corresponding 5-year progression-free survival rates were 81%(95% CI 71%-87%) without and 86% (95% CI 77%-91%) with pertuzumab; but the trial was not sufficiently powered to show statistical significant differences. Taking into account the stronger chemotherapy including a taxane and an anthracycline (or carboplatin), the effect size observed in the APHINITY study corresponds well to the reported neoadjuvant effect on reaching a pCR.

In conclusion, the APHINITY trial demonstrates that pertuzumab significantly improves IDFS in patients with operable HER2-positive breast cancer when added to chemotherapy and trastuzumab and no new safety signals were identified. Although further aspects, such as the efficacy or longer or shorter durations of treatment, will need to be further explored, this trial represents a landmark for the treatment of patients with HER2 positive EBC.

While certain embodiments of the present invention have been shown and described herein, it will be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
Sequence total quantity: 22
SEQ ID NO: 1            moltype = AA  length = 195
FEATURE                 Location/Qualifiers
source                  1..195
                        mol_type = protein
                        organism = Homo sapiens
SEQUENCE: 1
TQVCTGTDMK LRLPASPETH LDMLRHLYQG CQVVQGNLEL TYLPTNASLS FLQDIQEVQG   60
YVLIAHNQVR QVPLQRLRIV RGTQLFEDNY ALAVLDNGDP LNNTTPVTGA SPGGLRELQL  120
RSLTEILKGG VLIQRNPQLC YQDTILWKDI FHKNNQLALT LIDTNRSRAC HPCSPMCKGS  180
RCWGESSEDC QSLTR                                                  195

SEQ ID NO: 2            moltype = AA  length = 124
FEATURE                 Location/Qualifiers
source                  1..124
                        mol_type = protein
                        organism = Homo sapiens
SEQUENCE: 2
TVCAGGCARC KGPLPTDCCH EQCAAGCTGP KHSDCLACLH FNHSGICELH CPALVTYNTD   60
TFESMPNPEG RYTFGASCVT ACPYNYLSTD VGSCTLVCPL HNQEVTAEDG TQRCEKCSKP  120
CARV                                                              124

SEQ ID NO: 3            moltype = AA  length = 169
FEATURE                 Location/Qualifiers
source                  1..169
                        mol_type = protein
                        organism = Homo sapiens
SEQUENCE: 3
CYGLGMEHLR EVRAVTSANI QEFAGCKKIF GSLAFLPESF DGDPASNTAP LQPEQLQVFE   60
TLEEITGYLY ISAWPDSLPD LSVFQNLQVI RGRILHNGAY SLTLQGLGIS WLGLRSLREL  120
GSGLALIHHN THLCFVHTVP WDQLFRNPHQ ALLHTANRPE DECVGEGLA             169

SEQ ID NO: 4            moltype = AA  length = 142
FEATURE                 Location/Qualifiers
source                  1..142
                        mol_type = protein
                        organism = Homo sapiens
SEQUENCE: 4
CHQLCARGHC WGPGPTQCVN CSQFLRGQEC VEECRVLQGL PREYVNARHC LPCHPECQPQ   60
NGSVTCFGPE ADQCVACAHY KDPPFCVARC PSGVKPDLSY MPIWKFPDEE GACQPCPINC  120
THSCVDLDDK GCPAEQRASP LT                                          142

SEQ ID NO: 5            moltype = AA  length = 107
FEATURE                 Location/Qualifiers
source                  1..107
                        mol_type = protein
                        organism = Mus musculus
```

```
SEQUENCE: 5
DTVMTQSHKI MSTSVGDRVS ITCKASQDVS IGVAWYQQRP GQSPKLLIYS ASYRYTGVPD    60
RFTGSGSGTD FTFTISSVQA EDLAVYYCQQ YYIYPYTFGG GTKLEIK                 107

SEQ ID NO: 6            moltype = AA  length = 119
FEATURE                 Location/Qualifiers
source                  1..119
                        mol_type = protein
                        organism = Mus musculus
SEQUENCE: 6
EVQLQQSGPE LVKPGTSVKI SCKASGFTFT DYTMDWVKQS HGKSLEWIGD VNPNSGGSIY    60
NQRFKGKASL TVDRSSRIVY MELRSLTFED TAVYYCARNL GPSFYFDYWG QGTTLTVSS    119

SEQ ID NO: 7            moltype = AA  length = 107
FEATURE                 Location/Qualifiers
REGION                  1..107
                        note = Description of Artificial Sequence:
                        Syntheticpolypeptide
source                  1..107
                        mol_type = protein
                        organism = synthetic construct
SEQUENCE: 7
DIQMTQSPSS LSASVGDRVT ITCKASQDVS IGVAWYQQKP GKAPKLLIYS ASYRYTGVPS    60
RFSGSGSGTD FTLTISSLQP EDFATYYCQQ YYIYPYTFGQ GTKVEIK                 107

SEQ ID NO: 8            moltype = AA  length = 119
FEATURE                 Location/Qualifiers
REGION                  1..119
                        note = Description of Artificial Sequence:
                        Syntheticpolypeptide
source                  1..119
                        mol_type = protein
                        organism = synthetic construct
SEQUENCE: 8
EVQLVESGGG LVQPGGSLRL SCAASGFTFT DYTMDWVRQA PGKGLEWVAD VNPNSGGSIY    60
NQRFKGRFTL SVDRSKNTLY LQMNSLRAED TAVYYCARNL GPSFYFDYWG QGTLVTVSS    119

SEQ ID NO: 9            moltype = AA  length = 107
FEATURE                 Location/Qualifiers
REGION                  1..107
                        note = Description of Artificial Sequence:
                        Syntheticpolypeptide
source                  1..107
                        mol_type = protein
                        organism = synthetic construct
SEQUENCE: 9
DIQMTQSPSS LSASVGDRVT ITCRASQSIS NYLAWYQQKP GKAPKLLIYA ASSLESGVPS    60
RFSGSGSGTD FTLTISSLQP EDFATYYCQQ YNSLPWTFGQ GTKVEIK                 107

SEQ ID NO: 10           moltype = AA  length = 119
FEATURE                 Location/Qualifiers
REGION                  1..119
                        note = Description of Artificial Sequence:
                        Syntheticpolypeptide
source                  1..119
                        mol_type = protein
                        organism = synthetic construct
SEQUENCE: 10
EVQLVESGGG LVQPGGSLRL SCAASGFTFS SYAMSWVRQA PGKGLEWVAV ISGDGGSTYY    60
ADSVKGRFTI SRDNSKNTLY LQMNSLRAED TAVYYCARGR VGYSLYDYWG QGTLVTVSS    119

SEQ ID NO: 11           moltype = AA  length = 214
FEATURE                 Location/Qualifiers
REGION                  1..214
                        note = Description of Artificial Sequence:
                        Syntheticpolypeptide
source                  1..214
                        mol_type = protein
                        organism = synthetic construct
SEQUENCE: 11
DIQMTQSPSS LSASVGDRVT ITCKASQDVS IGVAWYQQKP GKAPKLLIYS ASYRYTGVPS    60
RFSGSGSGTD FTLTISSLQP EDFATYYCQQ YYIYPYTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 12           moltype = AA  length = 448
FEATURE                 Location/Qualifiers
REGION                  1..448
                        note = Description of Artificial Sequence:
```

```
                        Syntheticpolypeptide
source                  1..448
                        mol_type = protein
                        organism = synthetic construct
SEQUENCE: 12
EVQLVESGGG LVQPGGSLRL SCAASGFTFT DYTMDWVRQA PGKGLEWVAD VNPNSGGSIY    60
NQRFKGRFTL SVDRSKNTLY LQMNSLRAED TAVYYCARNL GPSFYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 13           moltype = AA  length = 214
FEATURE                 Location/Qualifiers
REGION                  1..214
                        note = Description of Artificial Sequence:
                        Syntheticpolypeptide
source                  1..214
                        mol_type = protein
                        organism = synthetic construct
SEQUENCE: 13
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 14           moltype = AA  length = 449
FEATURE                 Location/Qualifiers
REGION                  1..449
                        note = Description of Artificial Sequence:
                        Syntheticpolypeptide
source                  1..449
                        mol_type = protein
                        organism = synthetic construct
SEQUENCE: 14
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 15           moltype = AA  length = 217
FEATURE                 Location/Qualifiers
REGION                  1..217
                        note = Description of Artificial Sequence:
                        Syntheticpolypeptide
source                  1..217
                        mol_type = protein
                        organism = synthetic construct
SEQUENCE: 15
VHSDIQMTQS PSSLSASVGD RVTITCKASQ DVSIGVAWYQ QKPGKAPKLL IYSASYRYTG    60
VPSRFSGSGS GTDFTLTISS LQPEDFATYY CQQYYIYPYT FGQGTKVEIK RTVAAPSVFI   120
FPPSDEQLKS GTASVVCLLN NFYPREAKVQ WKVDNALQSG NSQESVTEQD SKDSTYSLSS   180
TLTLSKADYE KHKVYACEVT HQGLSSPVTK SFNRGEC                           217

SEQ ID NO: 16           moltype = AA  length = 449
FEATURE                 Location/Qualifiers
REGION                  1..449
                        note = Description of Artificial Sequence:
                        Syntheticpolypeptide
source                  1..449
                        mol_type = protein
                        organism = synthetic construct
SEQUENCE: 16
EVQLVESGGG LVQPGGSLRL SCAASGFTFT DYTMDWVRQA PGKGLEWVAD VNPNSGGSIY    60
NQRFKGRFTL SVDRSKNTLY LQMNSLRAED TAVYYCARNL GPSFYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 17           moltype = AA  length = 10
```

```
                              -continued

FEATURE                 Location/Qualifiers
REGION                  1..10
                        note = Description of Artificial Sequence: Syntheticpeptide
VARIANT                 10
                        note = D or S
source                  1..10
                        mol_type = protein
                        organism = synthetic construct
SEQUENCE: 17
GFTFTDYTMX                                                                          10

SEQ ID NO: 18           moltype = AA   length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 18
DVNPNSGGSI YNQRFKG                                                                  17

SEQ ID NO: 19           moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 19
NLGPSFYFDY                                                                          10

SEQ ID NO: 20           moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 20
KASQDVSIGV A                                                                        11

SEQ ID NO: 21           moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
VARIANT                 5
                        note = R or L
VARIANT                 6
                        note = Y or E
VARIANT                 7
                        note = T or S
SEQUENCE: 21
SASYXXX                                                                             7

SEQ ID NO: 22           moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 22
QQYYIYPYT                                                                           9
```

What is claimed is:

1. A method of adjuvant treatment for increasing invasive disease free survival (IDFS) at 3 years in patients with HER2-positive, node positive or hormone receptor negative, early breast cancer, said method comprising administering to said patients:

(a) pertuzumab intravenously every three weeks for 52 weeks, comprising an 840 mg loading dose of pertuzumab followed by 420 mg doses of mg pertuzumab;

(b) trastuzumab intravenously every three weeks for 52 weeks, comprising an 8 mg/kg loading dose of trastuzumab followed by 6 mg/kg doses of trastuzumab;

(c) taxane-based chemotherapy, comprising 3 or 4 cycles of 75 mg/m$^2$ and/or 100 mg/m$^2$ docetaxel every 3 weeks or 12 cycles of 80 mg/m$^2$ paclitaxel every week, wherein pertuzumab and trastuzumab are each administered intravenously starting on Day 1 of a first taxane-containing cycle;

(d) anthracycline-based chemotherapy administered before pertuzumab and trastuzumab administrations comprising 3 or 4 cycles of 5-fluorouracil+epirubicin+cyclophosphamide (FEC) or 5-fluorouracil+doxorubicin+cyclophosphamide (FAC) or 4 cycles of doxorubicin+cyclophosphamide (AC) or epirubicin+cyclophosphamide (EC); and wherein said IDFS at 3 years from initial administration in said patients is increased compared to patients to whom trastuzumab, taxane-based chemotherapy, and anthracycline-based chemotherapy without pertuzumab are administered.

2. The method of claim 1, wherein said patients are node positive.

3. The method of claim 2, wherein said node positive patients have 4 or more involved lymph nodes.

4. The method of claim 3, wherein said node positive patients have 4 to 9 involved lymph nodes.

5. The method of claim 1, wherein said patients are hormone receptor negative.

6. The method of claim 1, wherein said patients have a tumor >2 cm.

7. The method of claim 1, wherein said patients are node positive and hormone receptor negative.

8. The method of claim 1, wherein cardiac toxicity in said patients is not increased compared to patients to whom trastuzumab, taxane-based chemotherapy, and anthracycline-based chemotherapy without pertuzumab are administered, wherein said cardiac toxicity comprises drop in left ventricular ejection fraction (LVEF) of at least 10 points from baseline and to below 50%.

9. The method of claim 8, wherein said cardiac toxicity comprises asymptomatic or mildly symptomatic decline in LVEF defined by NYHA as Class II toxicity.

10. The method of claim 8, wherein said cardiac toxicity comprises symptomatic heart failure defined by NYHA as Class III/IV toxicity.

11. The method of claim 8, wherein said patients have a baseline left ventricular ejection fraction (LVEF) ≥55%.

12. The method of claim 1, wherein said anthracyline-based chemotherapy comprises 4 cycles of doxorubicin+cyclophosphamide (AC).

13. The method of claim 12, wherein said taxane-based chemotherapy comprises 4 cycles of 75 mg/m² docetaxel every 3 weeks.

14. A method of adjuvant treatment for increasing invasive disease free survival (IDFS) at 3 years in patients with HER2-positive, node positive or hormone receptor negative, early breast cancer, and with a baseline left ventricular ejection fraction (LVEF) ≥ 55%, said method comprising administering to said patients:

(a) pertuzumab intravenously every 3 weeks for 52 weeks, comprising a loading dose of 840 mg pertuzumab followed by 420 mg doses of pertuzumab;

(b) trastuzumab intravenously every 3 weeks for 52 weeks, comprising a loading dose of 8 mg/kg trastuzumab followed by 6 mg/kg doses of trastuzumab;

(c) taxane-based chemotherapy, comprising 3 or 4 cycles of 75 mg/m² or 100 mg/m² docetaxel every 3 weeks or 12 cycles of 80 mg/m² paclitaxel every week, wherein pertuzumab and trastuzumab are each administered intravenously starting on Day 1 of a first taxane-containing cycle;

(d) anthracycline-based chemotherapy administered before pertuzumab and trastuzumab administrations comprising 3 or 4 cycles of 5-fluorouracil+epirubicin+cyclophosphamide (FEC) or 5-fluorouracil+doxorubicin+cyclophosphamide (FAC) or 4 cycles of doxorubicin+cyclophosphamide (AC) or epirubicin+cyclophosphamide (EC); and wherein said IDFS at 3 years from initial administration in said patients is increased compared to patients to whom trastuzumab, taxane-based chemotherapy, and anthracycline-based chemotherapy without pertuzumab are administered.

15. The method of claim 14, wherein said patients are node positive.

16. The method of claim 15, wherein said node positive patients have 4 or more involved lymph nodes.

17. The method of claim 16, wherein said node positive patients have 4 to 9 involved lymph nodes.

18. The method of claim 14, wherein said patients are hormone receptor negative.

19. The method of claim 18, wherein said patients have a tumor >2 cm.

20. The method of claim 14, wherein said patients are node positive and hormone receptor negative.

21. The method of claim 14, wherein cardiac toxicity in said patients is not increased compared to patients to whom trastuzumab, taxane-based chemotherapy, and anthracycline-based chemotherapy without pertuzumab are administered, wherein said cardiac toxicity comprises drop in left ventricular ejection fraction (LVEF) of at least 10 points from baseline and to below 50%.

22. The method of claim 21, wherein said cardiac toxicity comprises asymptomatic or mildly symptomatic decline in LVEF defined by NYHA as Class II toxicity.

23. The method of claim 21, wherein said cardiac toxicity comprises symptomatic heart failure defined by NYHA as Class III/IV toxicity.

24. The method of claim 14, wherein said anthracyline-based chemotherapy comprises 4 cycles of doxorubicin+cyclophosphamide (AC).

25. The method of claim 24, wherein said taxane-based chemotherapy comprises 4 cycles of 75 mg/m² docetaxel every 3 weeks.

\* \* \* \* \*

UNITED STATES PATENT AND TRADEMARK OFFICE
CERTIFICATE OF CORRECTION

PATENT NO. : 12,128,103 B2
APPLICATION NO. : 18/637283
DATED : October 29, 2024
INVENTOR(S) : Mark C. Benyunes et al.

Page 1 of 1

It is certified that error appears in the above-identified patent and that said Letters Patent is hereby corrected as shown below:

In the Claims

In Column 49, Claim 1, Line 67, delete "of mg" and insert --of--

In Column 50, Claim 1, Line 63, delete "and/or" and insert --or--

In Column 51, Claim 6, Line 21, delete "claim 1," and insert --claim 5,--

In Column 51, Claim 12, Line 40, delete "anthracyline-" and insert --anthracycline--

In Column 52, Claim 24, Line 48, delete "anthracyline-" and insert --anthracycline--

Signed and Sealed this
Tenth Day of December, 2024

Katherine Kelly Vidal
*Director of the United States Patent and Trademark Office*